(12) United States Patent
Pulito et al.

(10) Patent No.: US 8,366,266 B2
(45) Date of Patent: Feb. 5, 2013

(54) SAFETY EYEWEAR

(75) Inventors: Brett Pulito, Blackstone, MA (US); Jason Gleason, West Greenwich, RI (US); Ray Curci, Smithfield, RI (US); Ricardo Silveira, Bridgewater, MA (US)

(73) Assignee: Sperian Eye & Face Protection, Inc., Smithfield, RI (US)

( * ) Notice: Subject to any disclaimer, the term of this patent is extended or adjusted under 35 U.S.C. 154(b) by 399 days.

(21) Appl. No.: 12/716,105

(22) Filed: Mar. 2, 2010

(65) Prior Publication Data

US 2010/0220283 A1 Sep. 2, 2010

Related U.S. Application Data

(63) Continuation-in-part of application No. 29/344,346, filed on Sep. 28, 2009, now Pat. No. Des. 614,359, and a continuation-in-part of application No. 29/344,351, filed on Sep. 28, 2009, now Pat. No. Des. 614,226, and a continuation-in-part of application No. 29/344,352, (Continued)

(51) Int. Cl.
*G02C 11/08* (2006.01)
(52) U.S. Cl. .......................................................... 351/62
(58) Field of Classification Search .................... 351/62, 351/47, 57, 158, 41; 2/435, 436, 437
See application file for complete search history.

(56) References Cited

U.S. PATENT DOCUMENTS

| | | | |
|---|---|---|---|
| 2,174,304 A | 9/1939 | Anderson et al. | |
| 2,354,772 A | 8/1944 | Prange | |
| 4,704,015 A | 11/1987 | Grendol et al. | |
| 4,783,163 A | 11/1988 | Breault | |
| 4,934,807 A | 6/1990 | Bolle et al. | |
| 5,015,087 A | 5/1991 | Baratelli | |
| 5,182,586 A | 1/1993 | Bennato | |
| 5,412,438 A | 5/1995 | Bolle | |
| 5,428,409 A | 6/1995 | Silverstein | |
| 5,428,410 A | 6/1995 | Lei | |
| 5,432,568 A | 7/1995 | Betz et al. | |
| 5,526,070 A | 6/1996 | Simioni | |
| 5,576,775 A | 11/1996 | Bolle | |
| 5,693,093 A | 12/1997 | Woffinden et al. | |
| 5,757,457 A | 5/1998 | Conway | |
| 5,768,716 A | 6/1998 | Porsche | |

(Continued)

OTHER PUBLICATIONS

"ESS Shooting Glasses", Eye Safety Systems, source Bing Internet search, http://www.gunnersalley.com/product/ESSGLASSES/ESS_Shooting_Glases.html.

(Continued)

*Primary Examiner* — Hung Dang
(74) *Attorney, Agent, or Firm* — Barlow, Josephs & Holmes, Ltd.

(57) ABSTRACT

The present invention relates generally to safety eyewear and more particularly to a safety eyewear including a wicking device attached to the safety eyewear to remove or absorb perspiration. The safety eyewear of the present invention includes the wicking device attached to a frame of the safety eyewear to remove or absorb perspiration. In one embodiment, the wicking device includes a brow-bar, sub-frame, and wicking material. The sub-frame removably or permanently attached to the frame of the safety eyewear using a variety of means for attachment to the eyewear frame. The brow bar removably or permanently attached using variety of means for attachment to the sub-frame. The wicking material removably or permanently attached using a variety of means for attachment to the brow bar.

21 Claims, 69 Drawing Sheets

Related U.S. Application Data filed on Sep. 28, 2009, now Pat. No. Des. 615,578, and a continuation-in-part of application No. 29/344,355, filed on Sep. 28, 2009, now Pat. No. Des. 651,641, and a continuation-in-part of application No. 29/344,356, filed on Sep. 28, 2009, now Pat. No. Des. 648,774.

(60) Provisional application No. 61/156,564, filed on Mar. 2, 2009, provisional application No. 61/246,781, filed on Sep. 29, 2009.

(56) References Cited

U.S. PATENT DOCUMENTS

| | | | |
|---|---|---|---|
| 6,045,577 A | 4/2000 | Woffinden et al. | |
| 6,106,117 A | 8/2000 | Huang Lin | |
| 6,159,397 A | 12/2000 | Friedman | |
| 6,257,719 B1 * | 7/2001 | Pavlak | 351/62 |
| 6,285,515 B1 | 9/2001 | Kitazawa et al. | |
| 6,386,705 B1 | 5/2002 | Chen | |
| 6,483,976 B2 | 11/2002 | Shie et al. | |
| 6,505,935 B2 | 1/2003 | Ayoub | |
| 6,641,263 B2 * | 11/2003 | Olney | 351/62 |
| 6,666,554 B2 | 12/2003 | Mulvey | |
| 6,857,739 B1 | 2/2005 | Watson | |
| 6,860,600 B2 | 3/2005 | Chen | |
| 6,991,333 B2 | 1/2006 | Van Atta et al. | |
| 7,014,316 B2 | 3/2006 | Asakura | |
| 7,086,734 B2 | 8/2006 | Chen | |
| 7,147,321 B2 | 12/2006 | Van Atta | |
| 7,172,281 B2 * | 2/2007 | Chen | 351/62 |
| 7,431,451 B1 | 10/2008 | Lin | |
| 7,452,068 B2 | 11/2008 | Collier et al. | |
| 2005/0105042 A1 | 5/2005 | Lin | |
| 2005/0225715 A1 | 10/2005 | Kopfer | |
| 2007/0252942 A1 | 11/2007 | Collier et al. | |
| 2008/0266515 A1 | 10/2008 | Hou | |
| 2009/0079931 A1 | 3/2009 | Yang | |
| 2009/0115962 A1 | 5/2009 | Bovet et al. | |
| 2009/0141236 A1 | 6/2009 | Chen et al. | |

OTHER PUBLICATIONS

Seegers, John, "Chapter 8: Lens Treatments", source Google search, URL?Accession No. "http://www.opticianworks.com/chapter8.html" Note: scroll down to section titled "Edge Coatings".

OMS Opto Chemicals, "EDGIT A full Polycarbonate edge treatment system", source: Google search, URL/Accession No. "http://optochemicals.com/poly_edgit.htm".

* cited by examiner

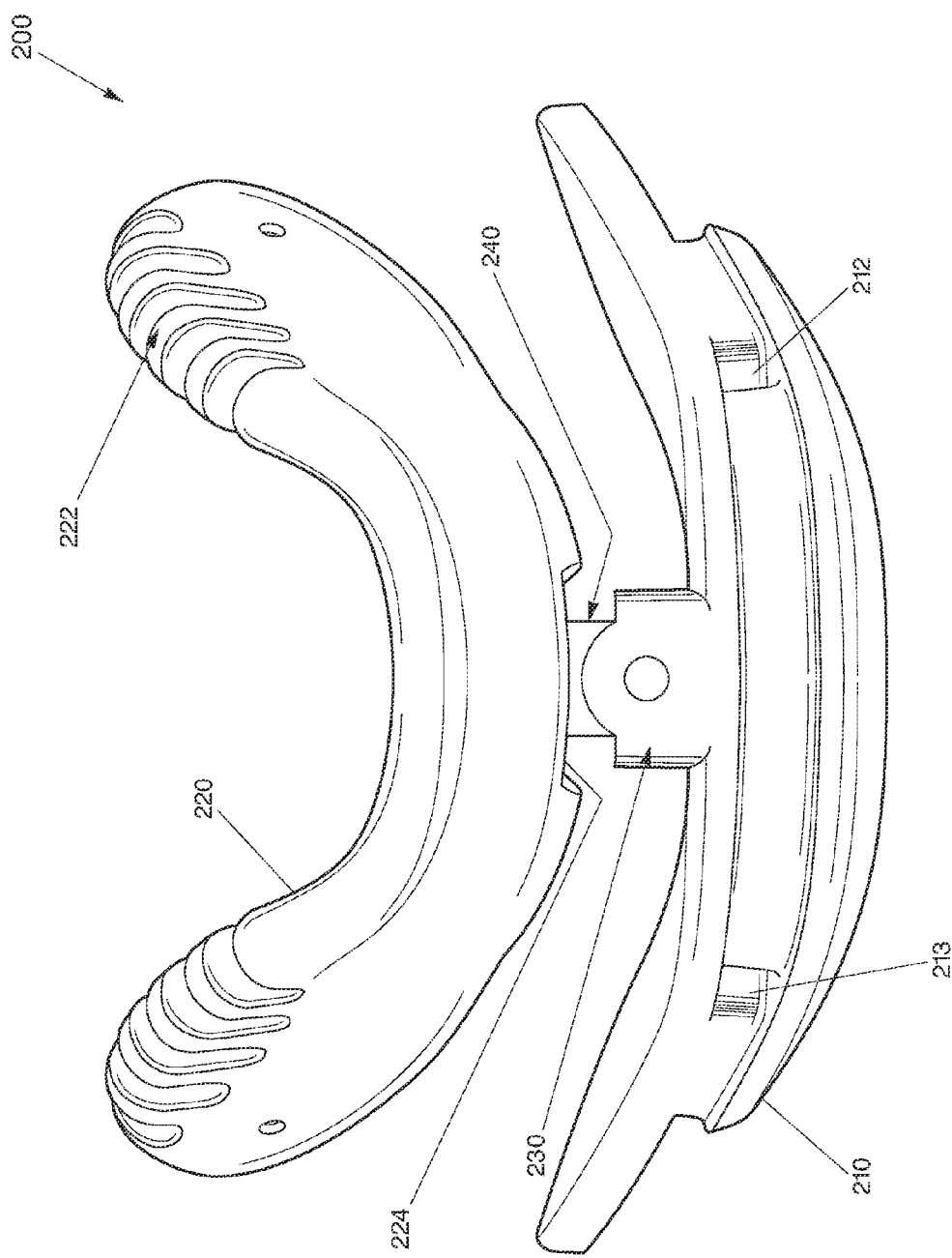

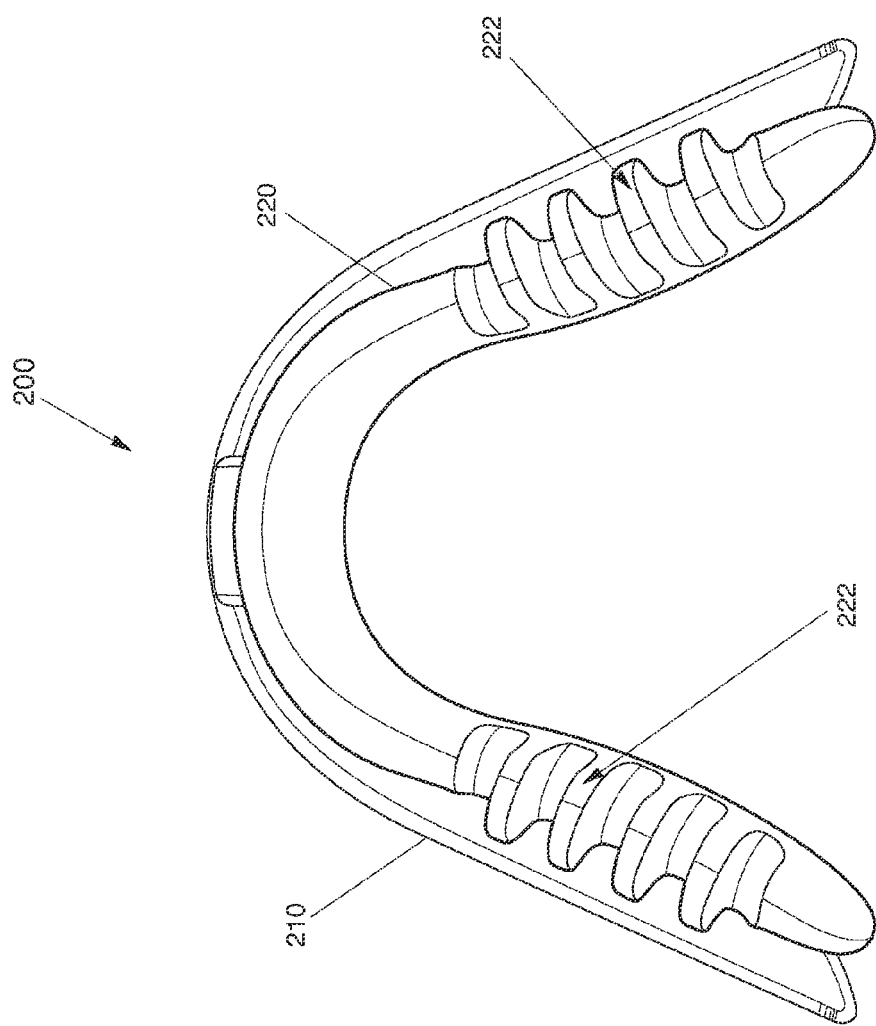

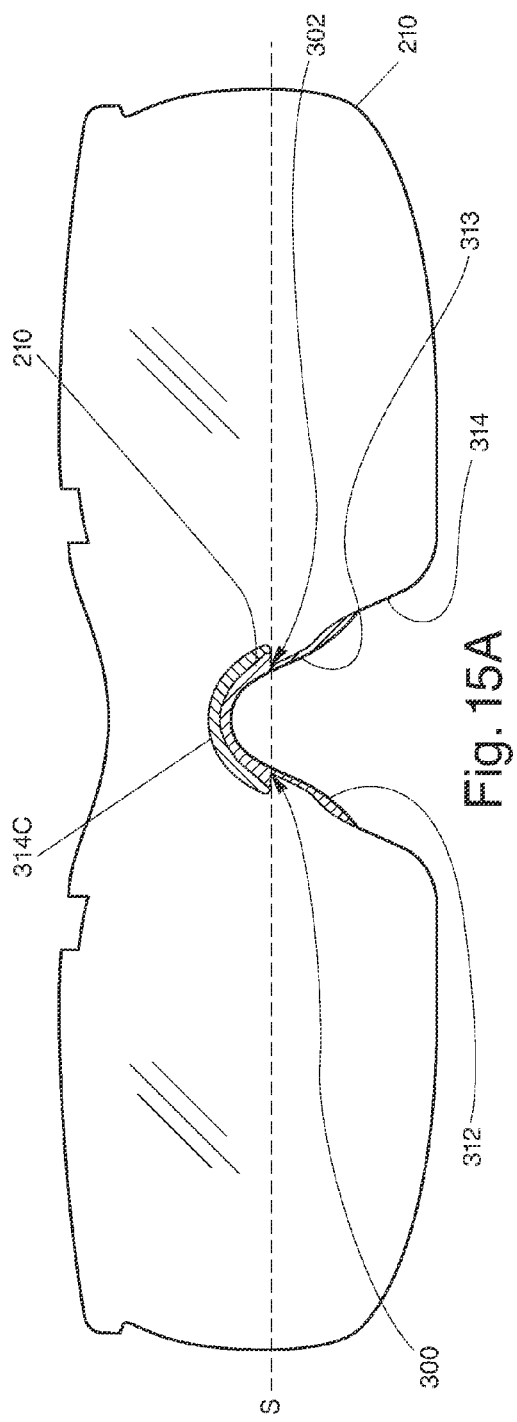
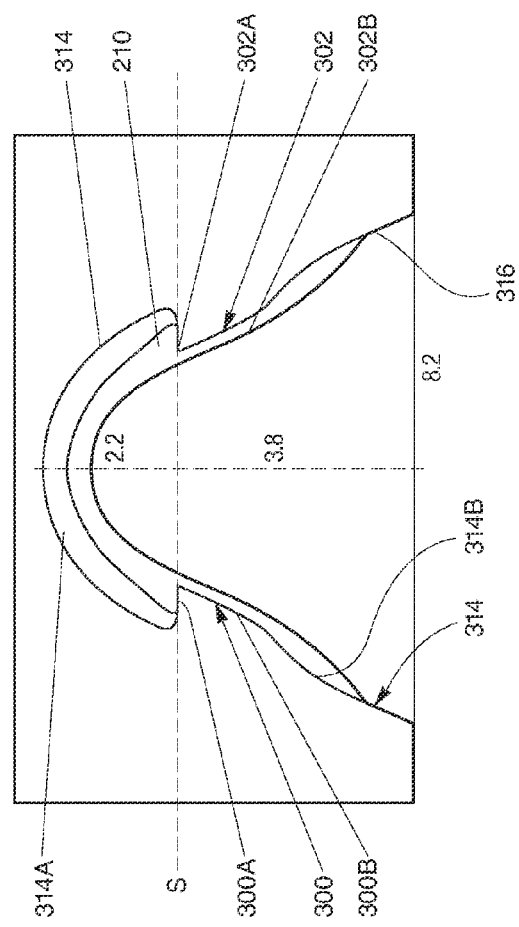
Fig. 15A
Fig. 15B

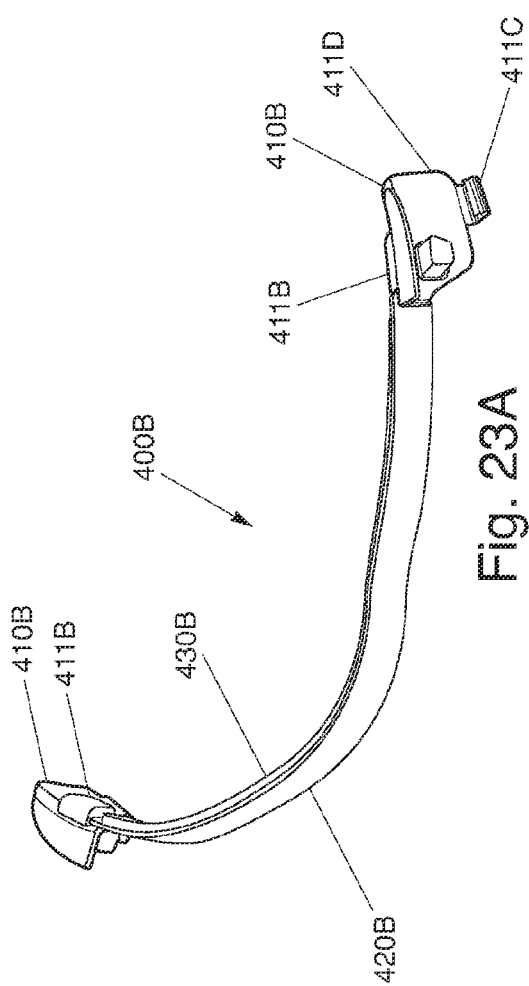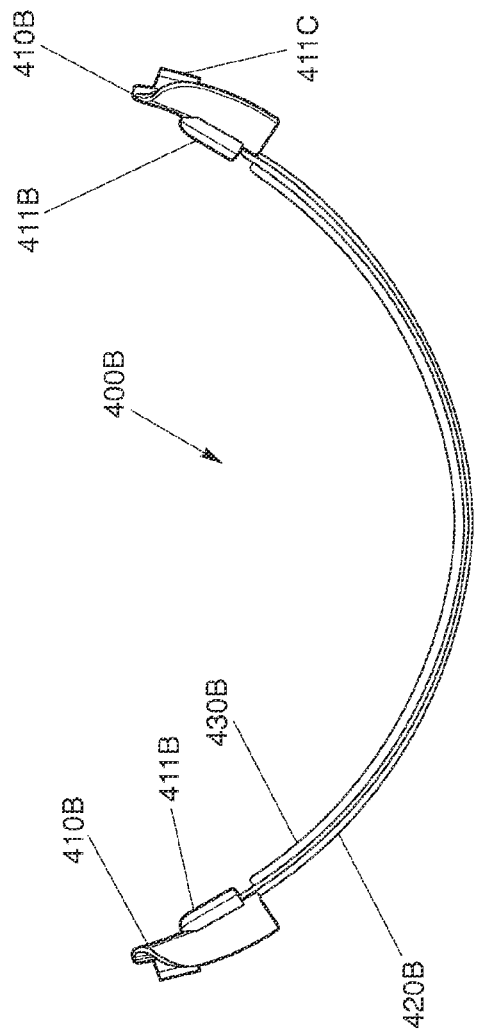

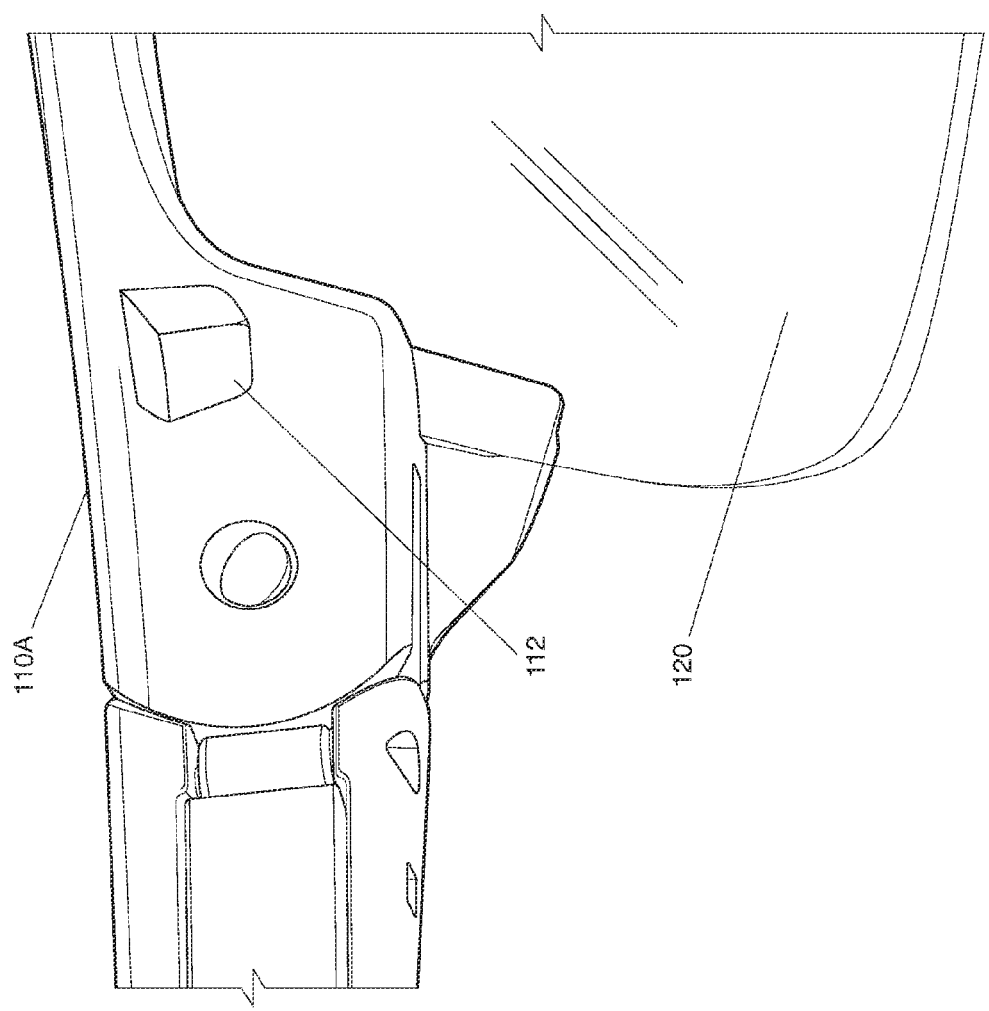

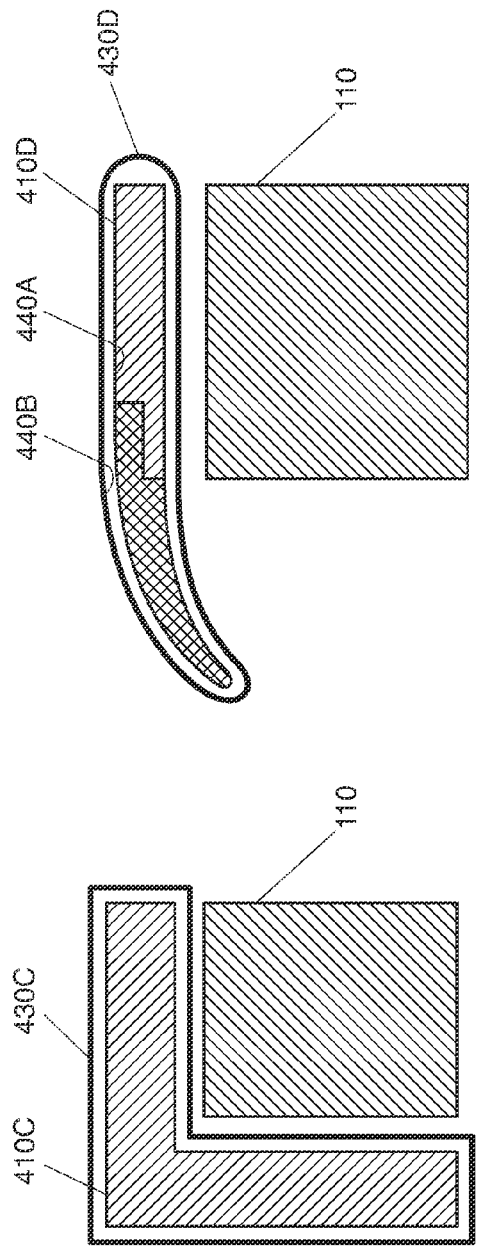
Fig. 26A
Fig. 26B
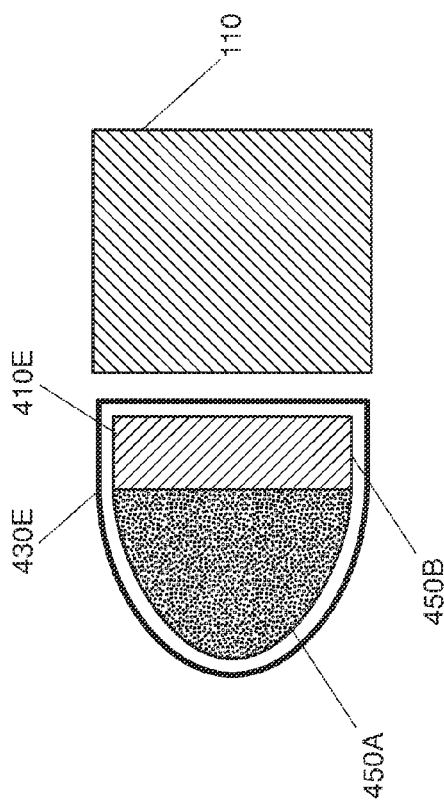
Fig. 26C

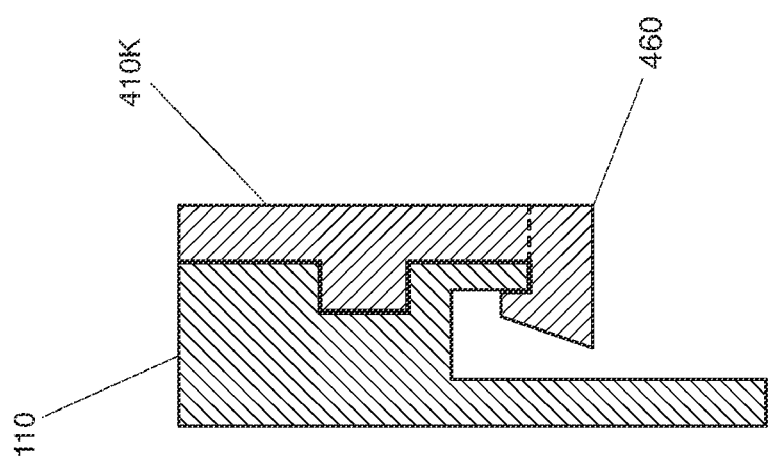

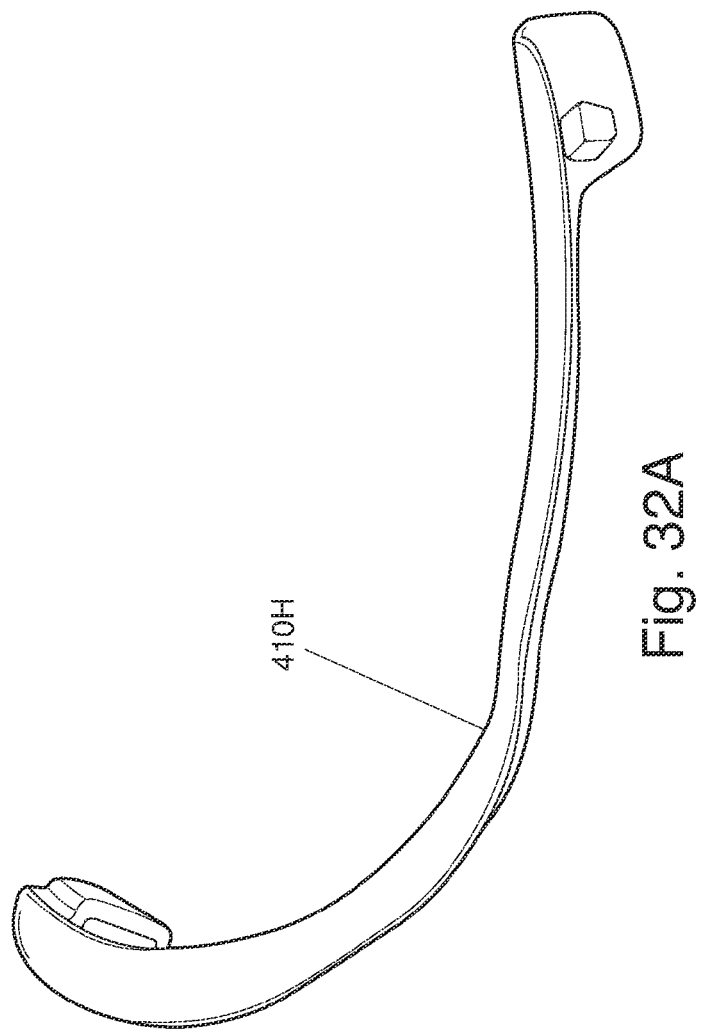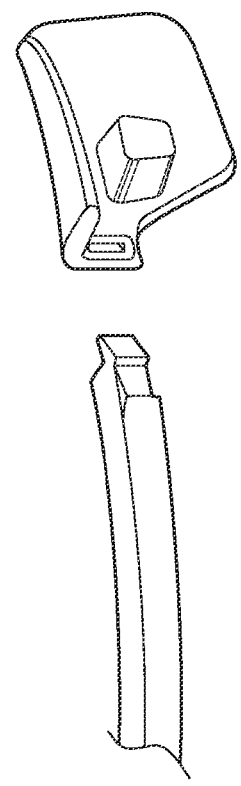
Fig. 32A
Fig. 32B

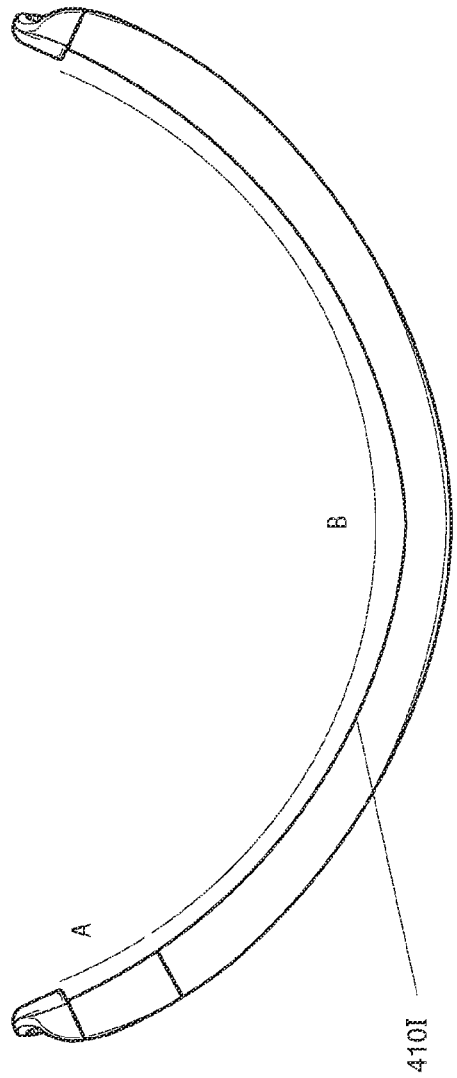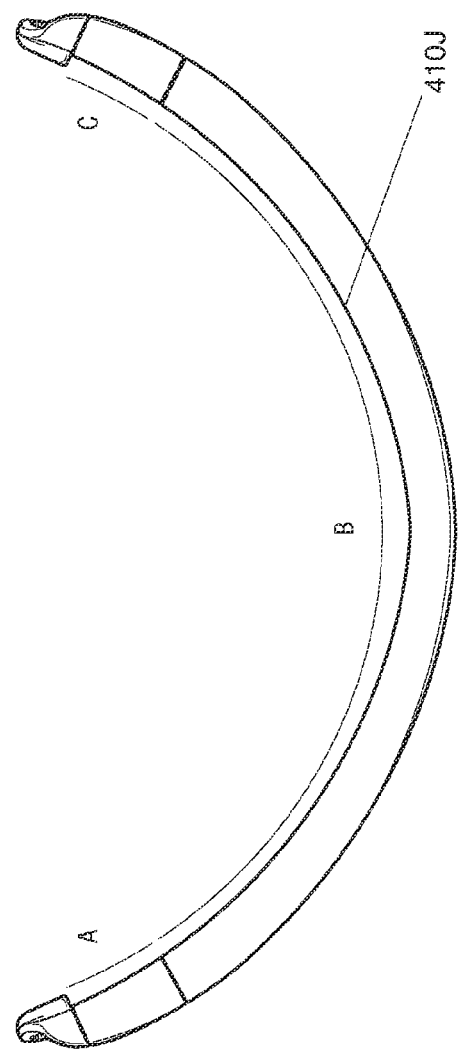
Fig. 32C
Fig. 32D

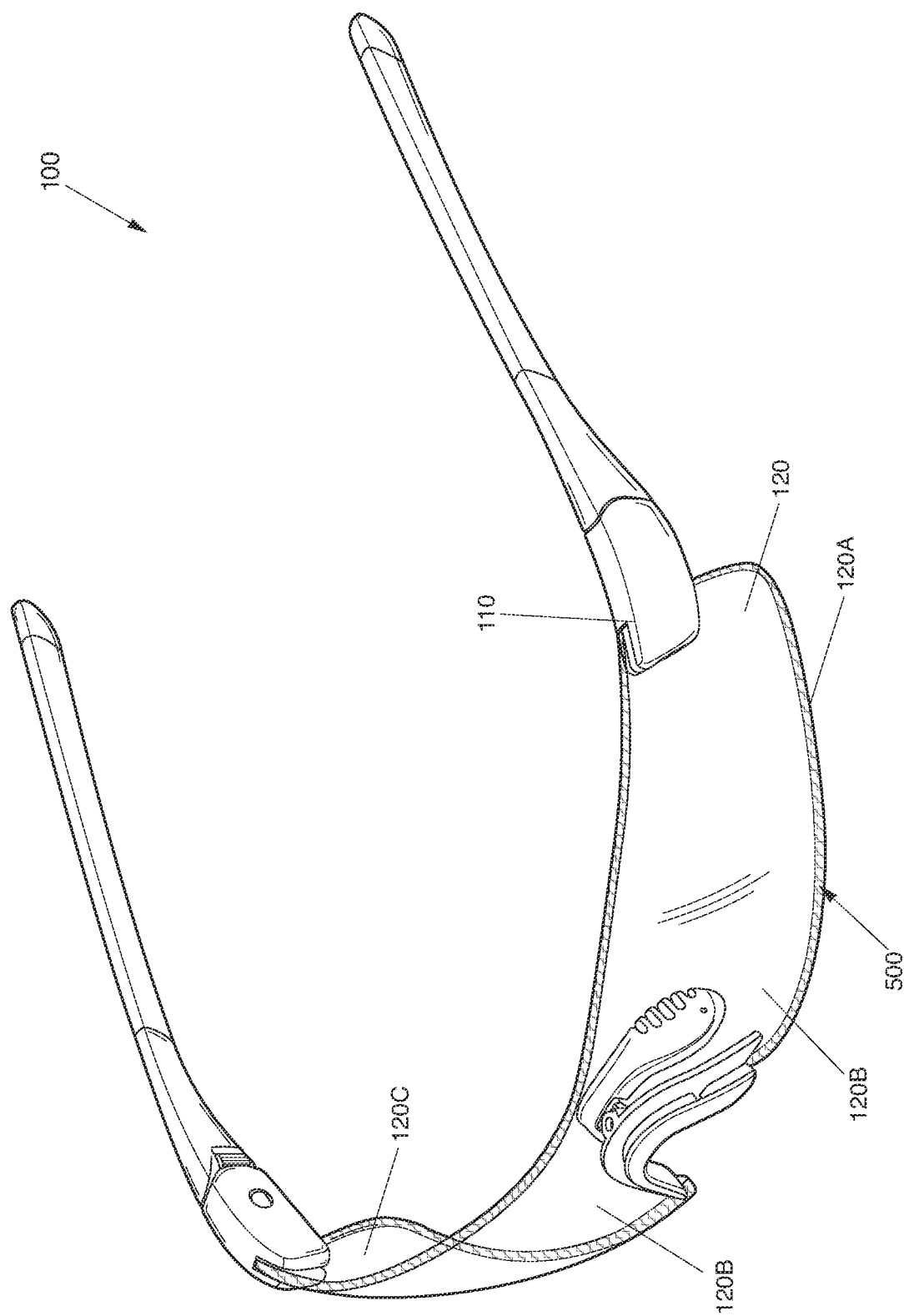

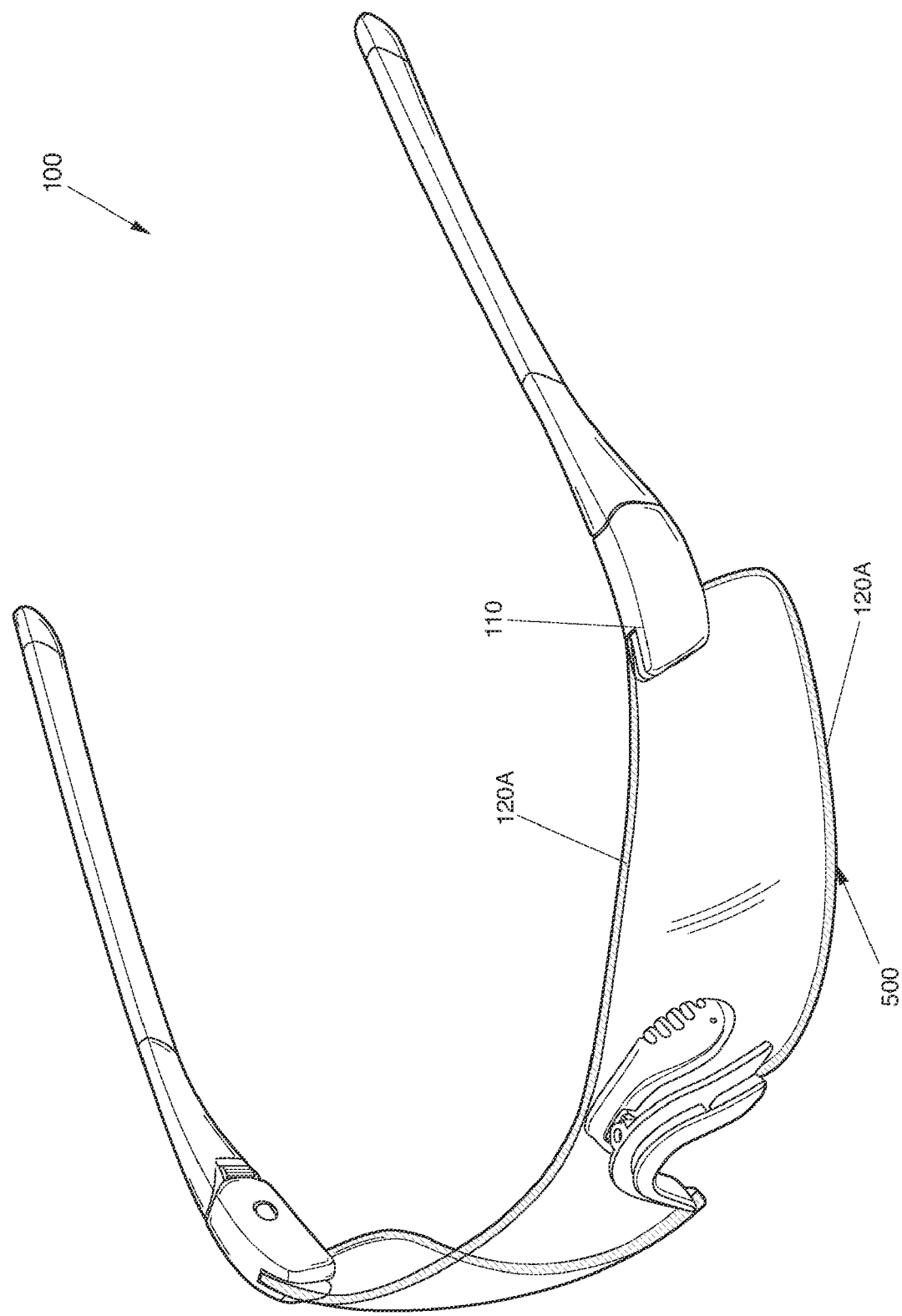

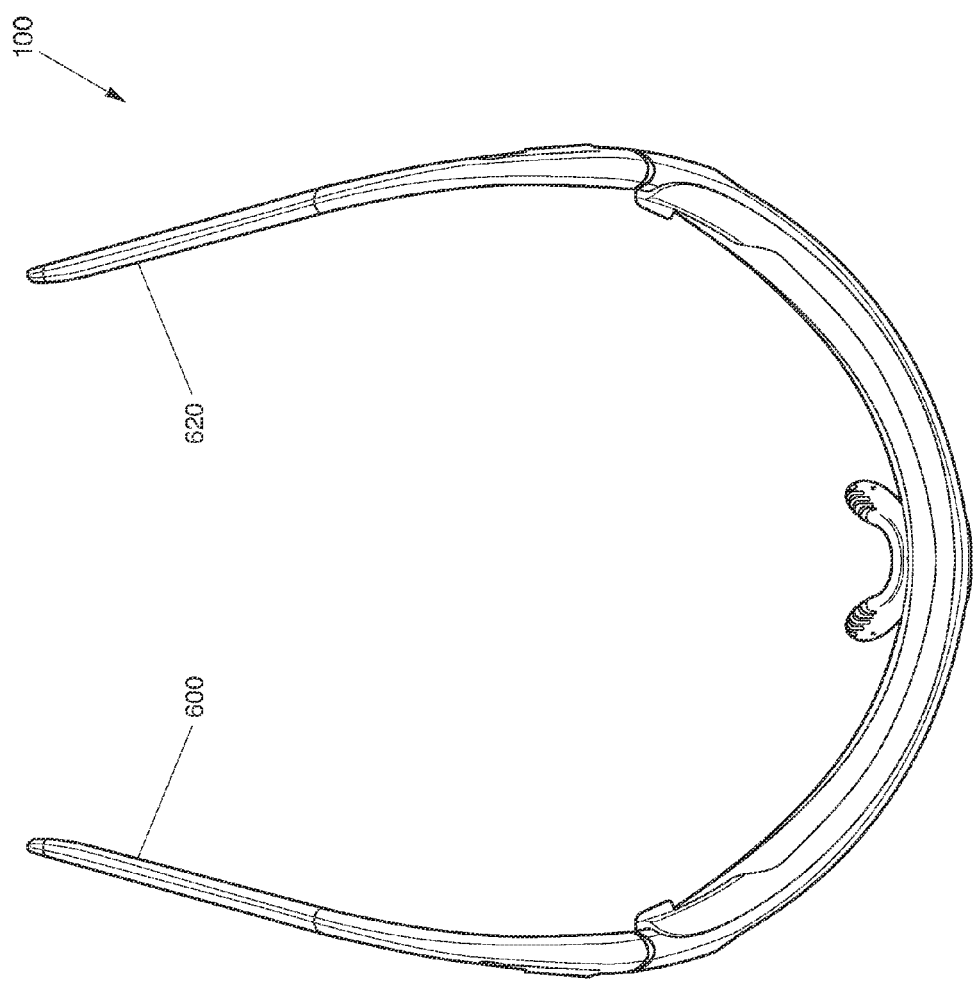

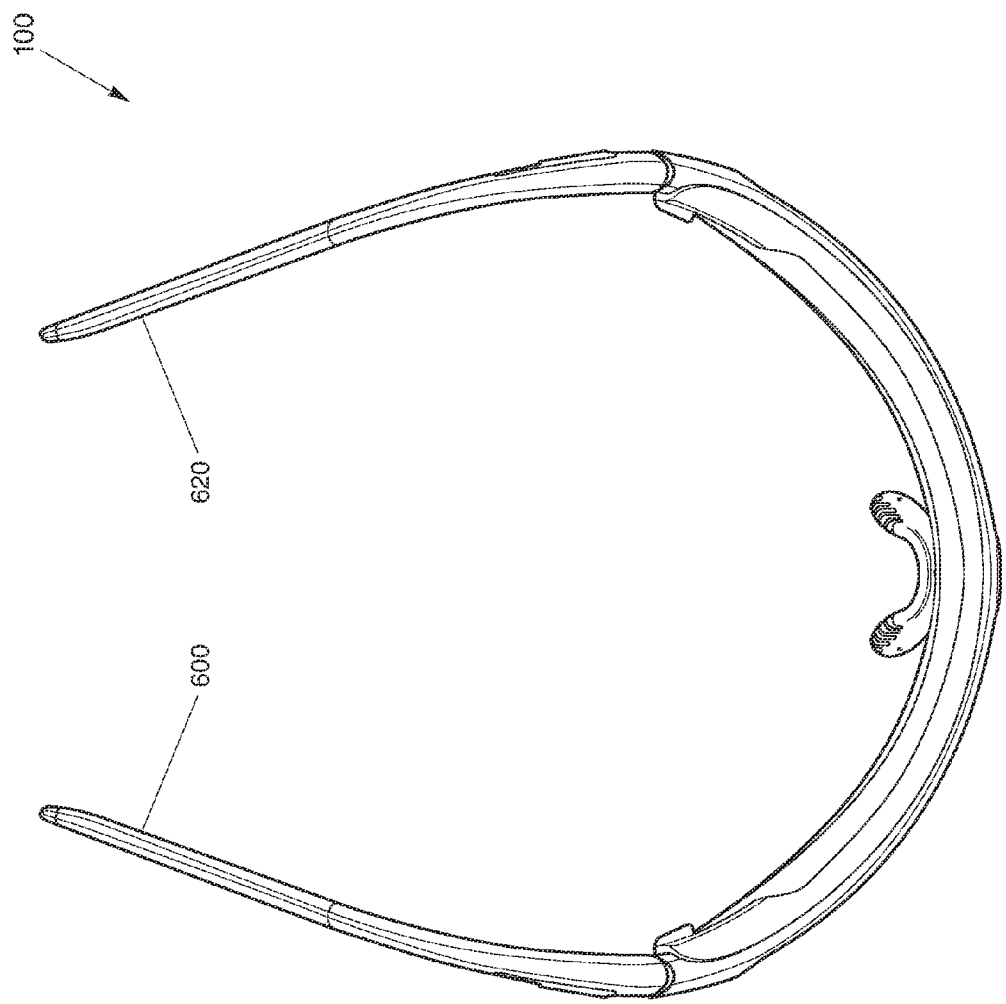

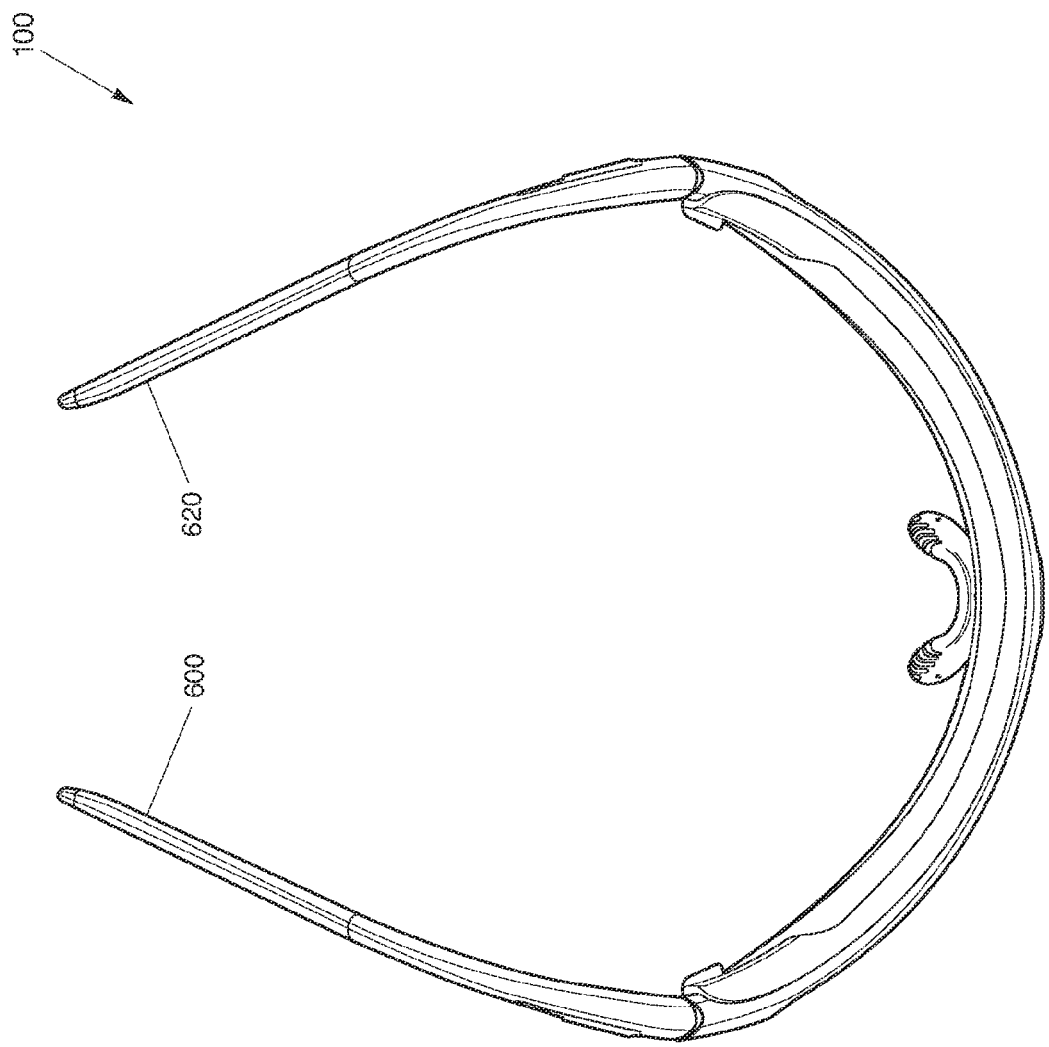

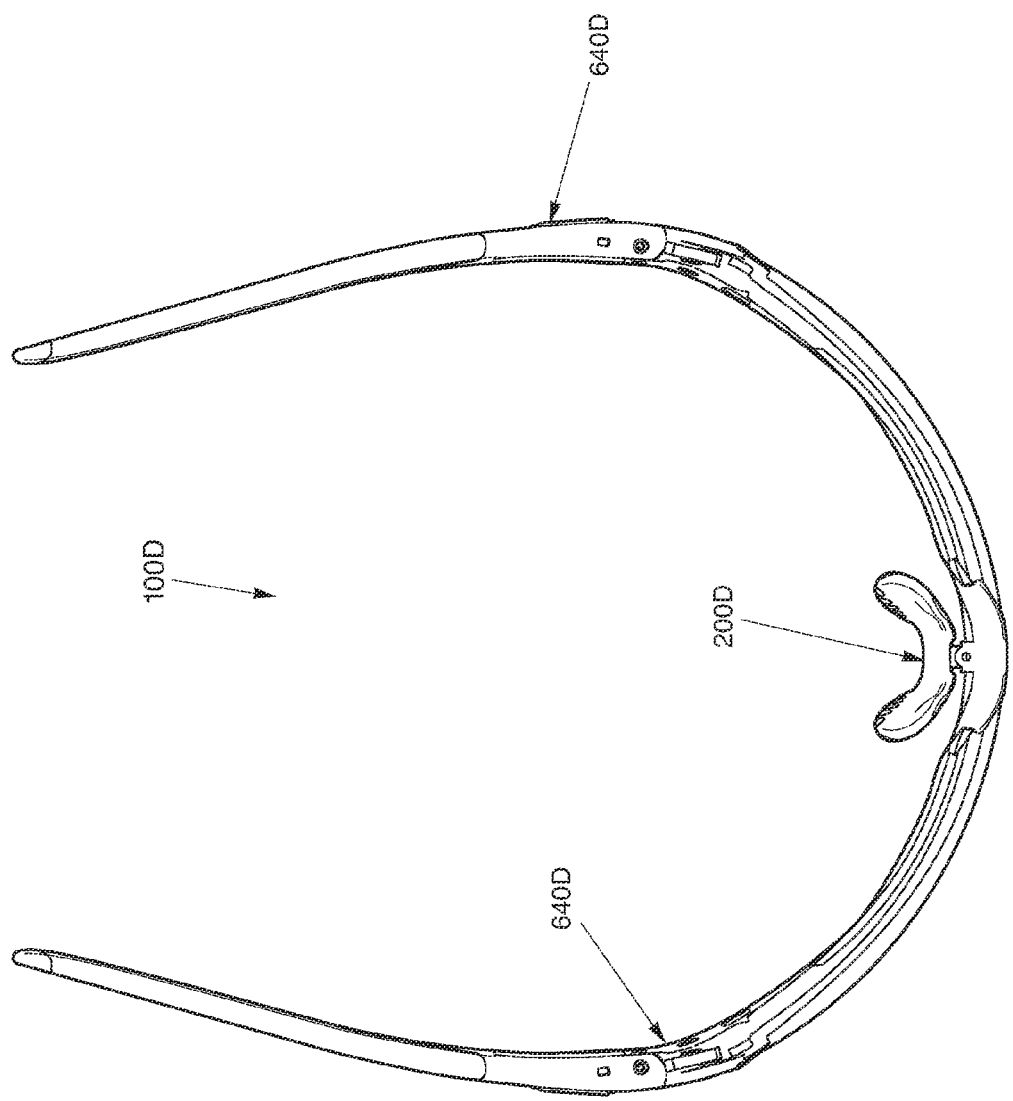

SAFETY EYEWEAR

CROSS REFERENCE TO RELATED APPLICATIONS

This application is related to and claims priority from earlier filed U.S. Provisional Patent Application Ser. No. 61/156,564 filed Mar. 2, 2009, continuation-in-part of earlier filed U.S. Design patent application Ser. No. 29/344,346 filed Sep. 28, 2009, now U.S. Design Pat. No. D,614,359 continuation-in-part of earlier filed U.S. Design patent application Ser. No. 29/344,351 filed Sep. 28, 2009, now U.S. Design Pat. No. D,614,226 continuation-in-part of earlier filed U.S. Design patent application Ser. No. 29/344,352 filed Sep. 28, 2009, now U.S. Design Pat. No. D,615,578 continuation-in-part of earlier filed U.S. Design patent application Ser. No. 29/344,355 filed Sep. 28, 2009, now U.S. Design Pat. No. D,651,641 continuation-in-part of earlier filed U.S. Design patent application Ser. No. 29/344,356, filed Sep. 28, 2009, now U.S. Design Pat. No. D,648,774 and earlier filed U.S. Provisional Patent Application Ser. No. 61/246,781 filed Sep. 29, 2009, the entire contents of all applications are incorporated herein by reference.

BACKGROUND OF THE INVENTION

The present invention relates generally to safety eyewear and more particularly to a safety eyewear including a wicking device attached to the safety eyewear to remove or absorb perspiration.

Wearing of eyeglasses and the like while engaged in vigorous activity can be difficult for various reasons. One reason is a fundamental inability of most eyeglass frames to remain properly attached to the wearer's face whenever the wearer is engaged in activity including rapid or extensive movements of the head and/or body. A conventional eyeglass having this disadvantage likely will become detached from the wearer's face in such instances, especially during activities which generate perspiration.

Another reason is a general discomfort associated with wearing eyeglasses in conjunction with a helmet, hat or other headgear, which is commonly worn when participating in vigorous activities, such as skiing, bike riding, rafting, climbing, motorcycling, etc. With many known eyeglass designs, nose pieces can be bulky or non-conforming to a user's nose such that when worn with a helmet, the nose can be uncomfortably and often painfully pressed against the nose piece structure. Further, some devices and mechanisms coupled to the nose piece structure and designed to keep the eyeglasses on the wearer's face act only to magnify this discomfort.

Another reason is the lack of adjustment features in many eyeglasses that prevent customization of the eyewear to the wearer's face. Such customization allows individual fitting of the eyewear to that wearer's individual facial profile for comfort and security when in use. Many eyeglasses today lack the customization necessary to adapt to various head shapes and ethnic profiles.

Many people wear eyeglasses for reasons other than, or in addition to, vision correction. Well-known examples are the large number of different types of "sunglasses" that reduce the intensity (and/or change the wavelength) of light reaching the wearer's eyes. Other well-known examples are so-called "safety glasses" usually used for eye protection against identified hazards in industrial, occupational and laboratory environments. Yet other well-known examples are various "goggles" and the like.

To address the concerns raised by the need for eyewear that will remain on the wearer's face during vigorous activity, various schemes have been adopted. For example, certain types of eyewear, notably goggles and certain types of eyeglasses, employ a strap, elastic band, cord, or analogous feature (usually adjustable) that extends fully around the rear of the wearer's head, rearwardly of the ears. Unfortunately, although these features are effective, they can be uncomfortable and are usually not favored for use when style is important. Also, eyewear with this feature is difficult to put on and take off, especially when the wearer is also wearing a hat or helmet. Other types of eyewear have temple pieces with metal-like, semicircular, "wrap-around" ear-engaging portions that curve downward fully behind the wearer's ears.

The prior art safety eyewear suffers from a couple of disadvantages. Specifically, the prior art does not allow for safety eyewear including a wicking device attached to the safety eyewear to remove or absorb perspiration. Accordingly, it would be desirable in the art to have a safety eyewear that includes a wicking device attached to the safety eyewear to remove or absorb perspiration.

BRIEF SUMMARY OF THE INVENTION

The invention preserves the advantages of prior safety eyewear. In addition, it provides new advantages not found in currently available safety eyewear and overcomes many disadvantages of such currently available safety eyewear.

The safety eyewear of the present invention includes a wicking device attached to the safety eyewear to remove or absorb perspiration.

The safety eyewear of the present invention includes the wicking device attached to a frame of the safety eyewear to remove or absorb perspiration. In one embodiment, the wicking device includes a brow-bar, sub-frame, and wicking material. The sub-frame removably or permanently attached to the frame of the safety eyewear using a variety of means for attachment to the eyewear frame. The brow bar removably or permanently attached using variety of means for attachment to the sub-frame. The wicking material removably or permanently attached using a variety of means for attachment to the brow bar. It is also contemplated that the wicking device may include additional combinations such as the brow-bar and the wicking material or sub-frame and wicking material using a variety of means for attachment to the eyewear.

An object of the present invention is to provide a wicking device attached to the safety eyewear to remove or absorb perspiration.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

FIG. 10 is top view of the nose piece structure of FIG. 7A;

FIG. 12A is a rear view of the nose piece structure of FIG. 7A showing an example of a first position of adjustment of the fins along an axis;

FIG. 15A is a front view of the horizontal ledge defined within the lens of the safety eyewear;

FIG. 15B is a partial view of the lens of FIG. 15A having the horizontal ledge;

FIG. 23A is a perspective view of an alternative embodiment of FIG. 16;

FIG. 23B is a top view of an alternative embodiment of FIG. 16;

FIG. 24 is a partial view of the inner surface of the frame connection portion;

FIG. 26A is a cross-sectional view of a wicking device including a wicking sub-frame and wicking material;

FIG. 26B is a cross-sectional view of another example of a wicking device including a wicking sub-frame and wicking material;

FIG. 26C is a cross-sectional view of another example of a wicking device including a wicking sub-frame and wicking material;

FIG. 27 is a cross-sectional view of a holding mechanism used for attaching the brow bar area to the wicking sub-frame;

FIG. 32A is perspective view of an alternative embodiment of the wicking sub-frame;

FIG. 32B is a perspective view of an alternative embodiment of the wicking sub-frame;

FIG. 32C is a top view of an alternative embodiment of the wicking sub-frame;

FIG. 32D is a top view of an alternative embodiment of the wicking sub-frame;

FIG. 33 is a perspective view of the colored tinting along the outer peripheral edge of the lens;

FIG. 34 is a perspective view of another embodiment of the colored tinting along the outer peripheral edge of the lens;

FIG. 40 is a top view of the safety eyewear of FIG. 36;

FIG. 41 is a top view of the safety eyewear of FIG. 36;

FIG. 42 is a top view of the safety eyewear of FIG. 36;

FIG. 63 is a bottom view thereof.

DETAILED DESCRIPTION OF THE PREFERRED EMBODIMENTS

Figure 1:
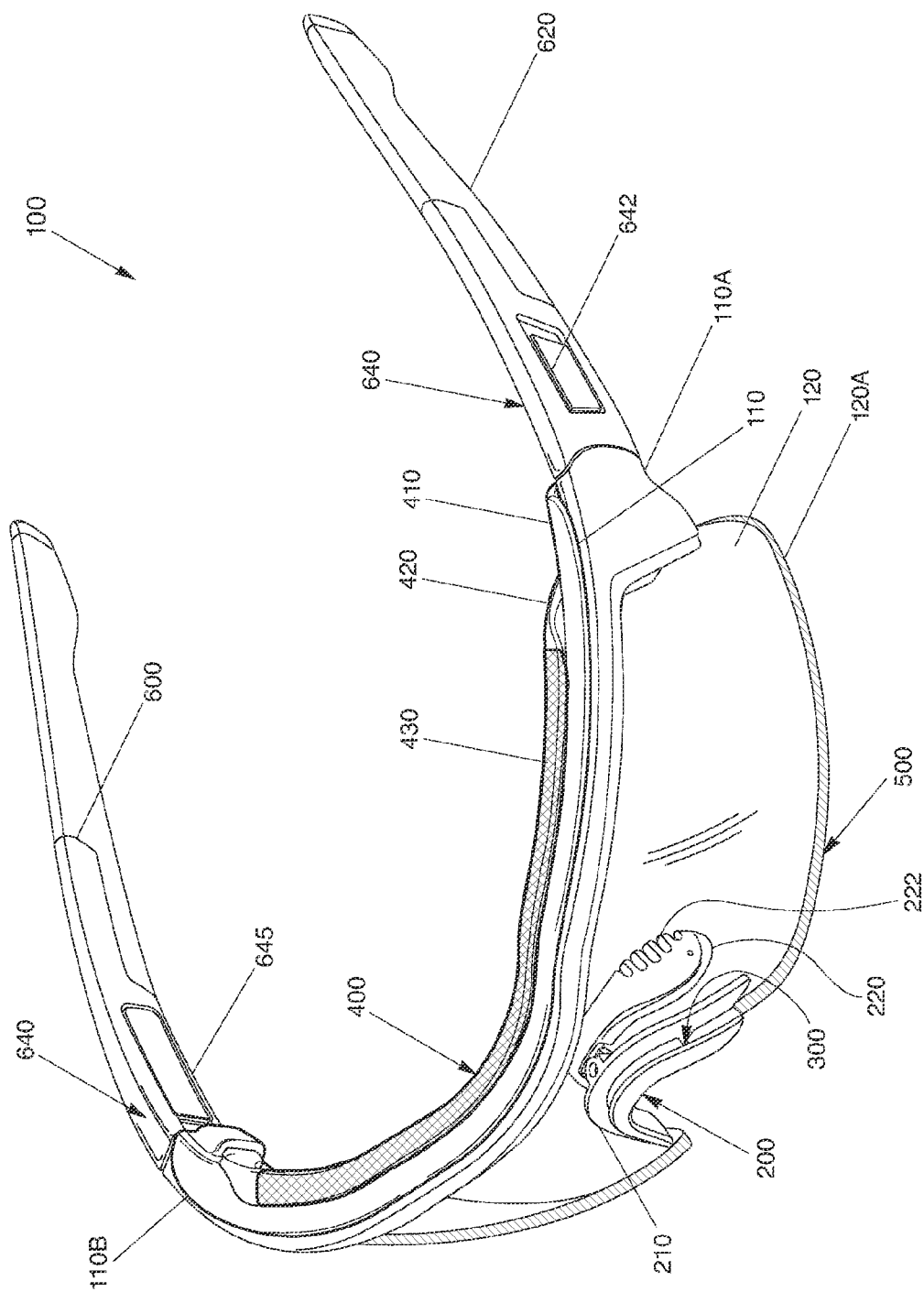
FIG. 1 is a perspective view of the safety eyewear in accordance with the present invention including a nose piece structure, a horizontal ledge defined within the lens, a wicking device, a coloration or tinting of an outer peripheral edge of the lens, and temple bars having adjustable width.
Figure 2:
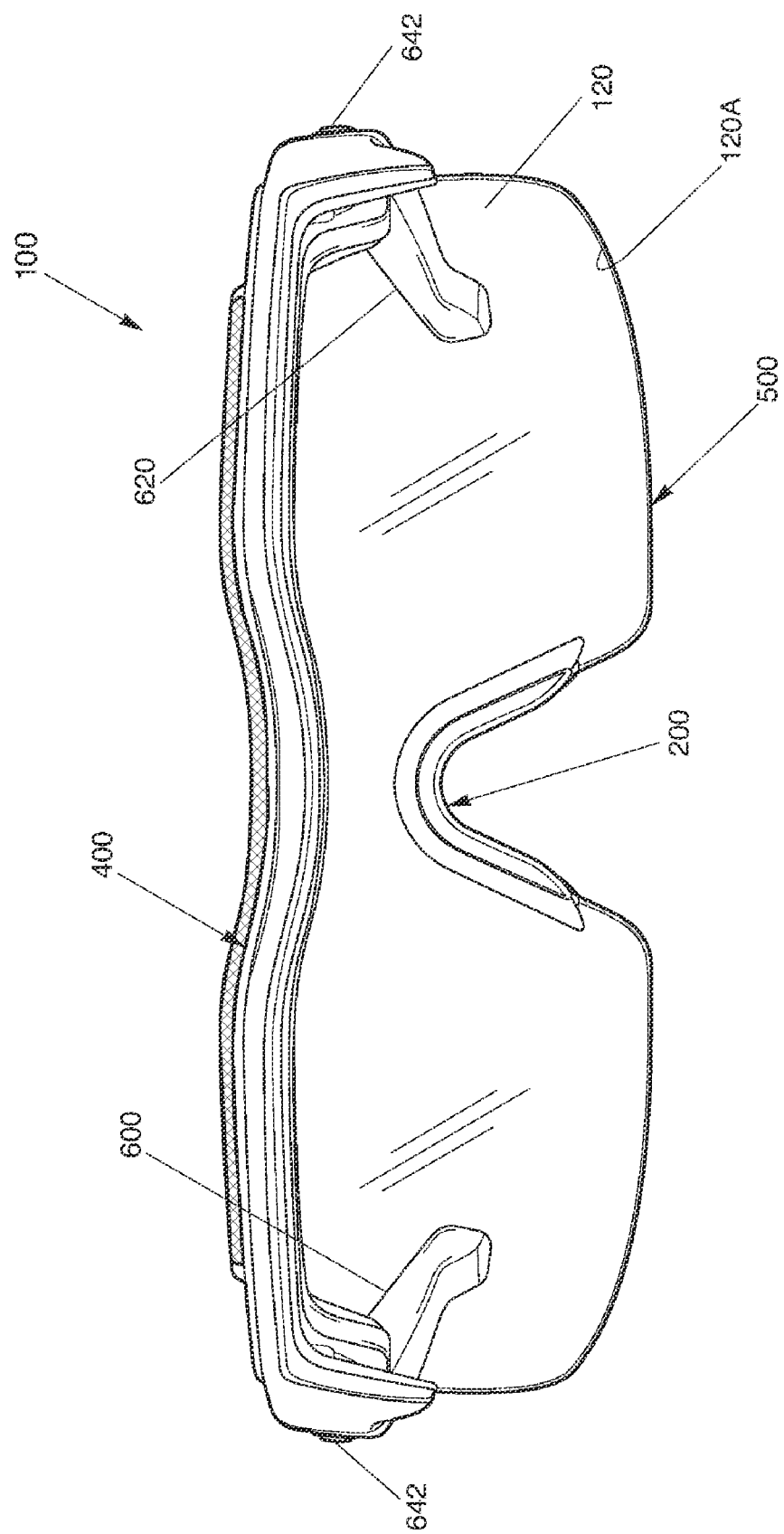
FIG. 2 is a front view thereof.
Figure 3:
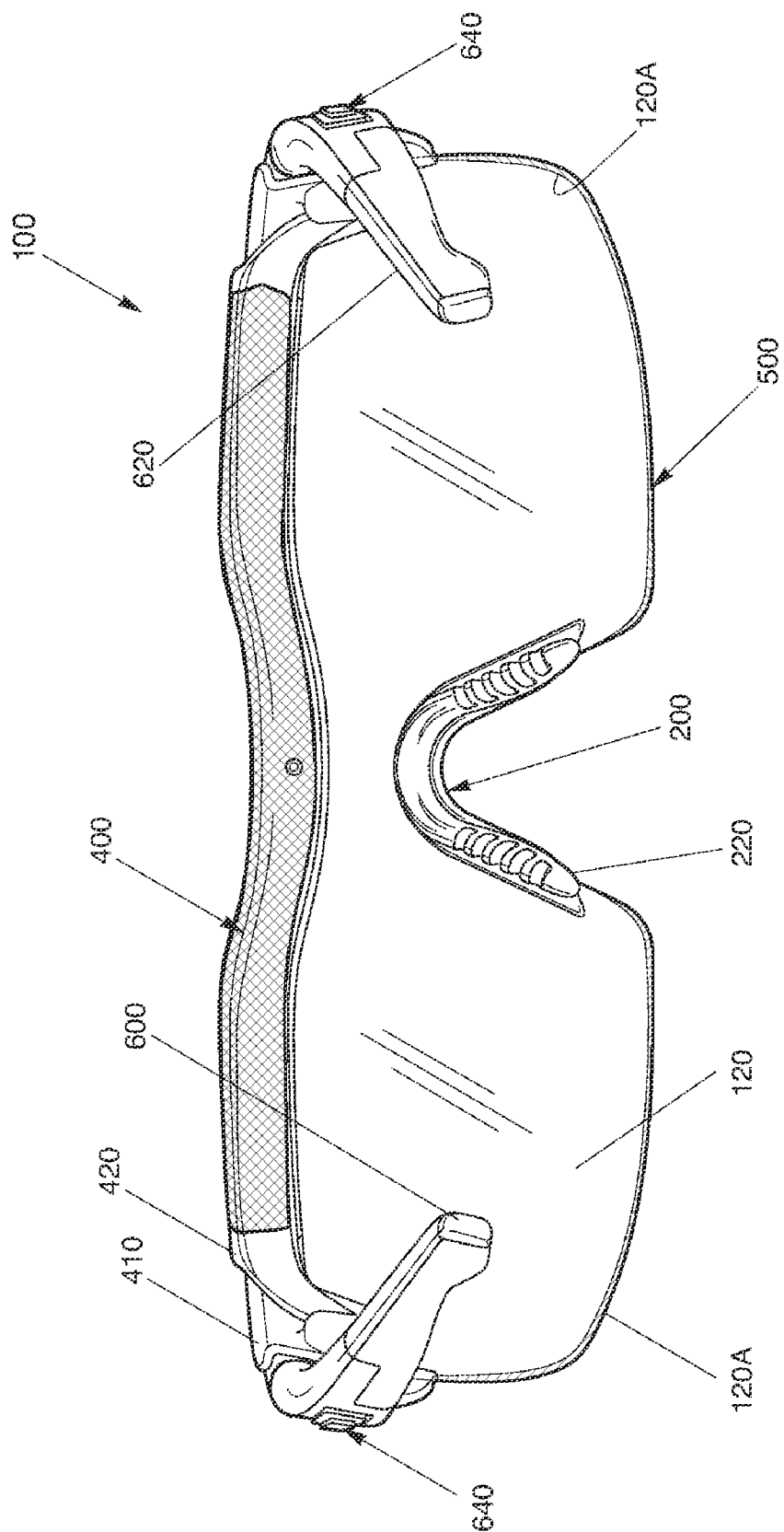
FIG. 3 is a rear view thereof.
Figure 4:
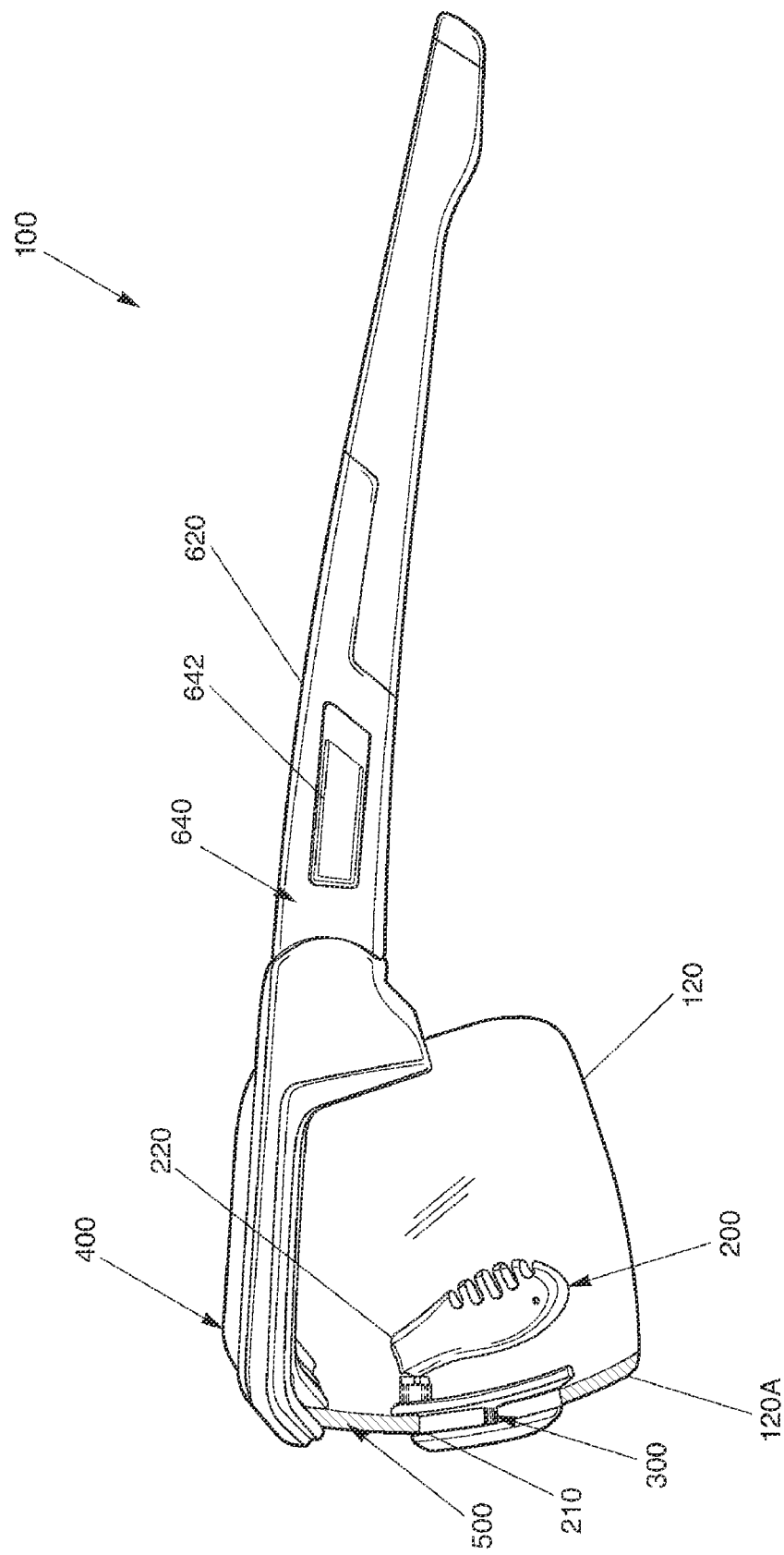
FIG. 4 is a right view thereof, the left view is a mirror image thereof.
Figure 5:
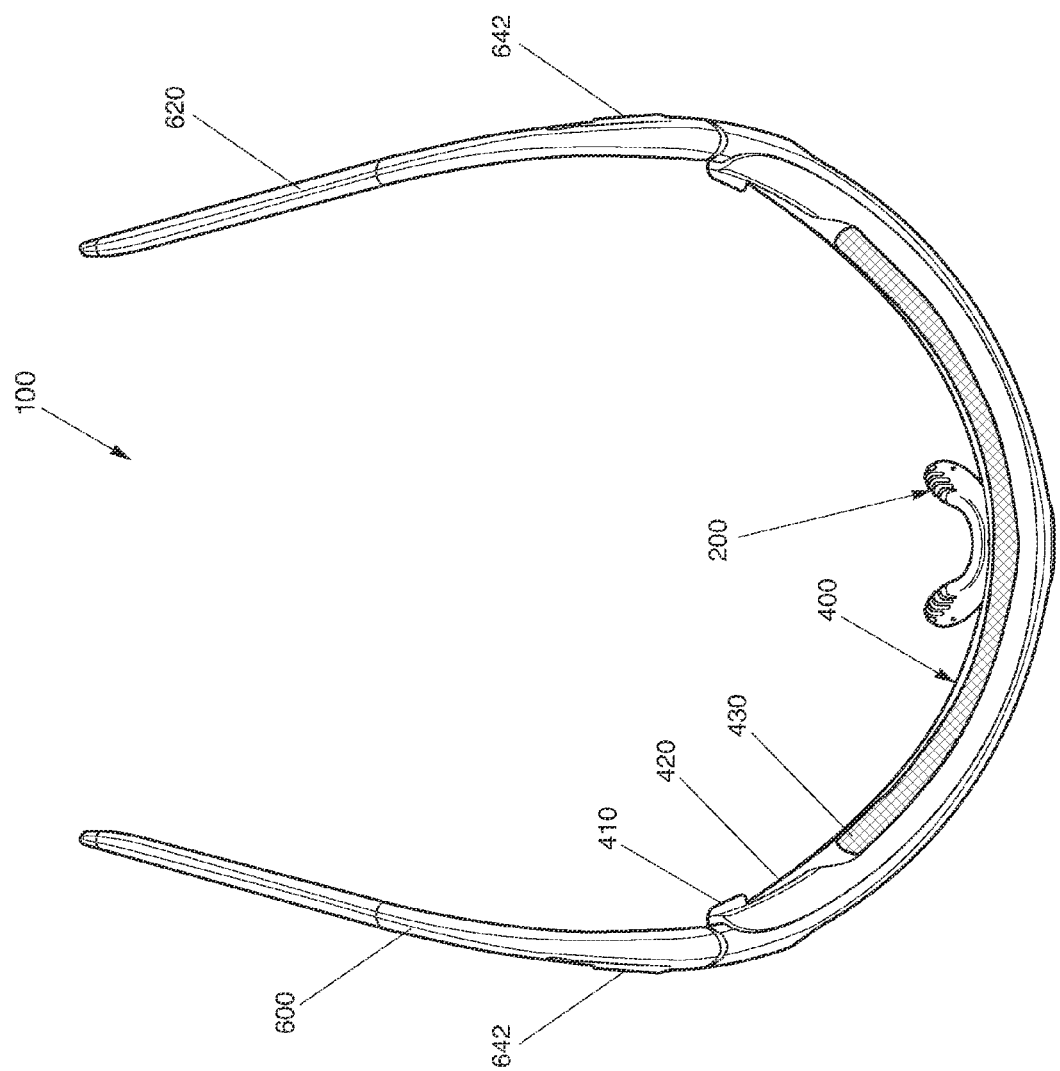
FIG. 5 is a top view thereof.
Figure 6:
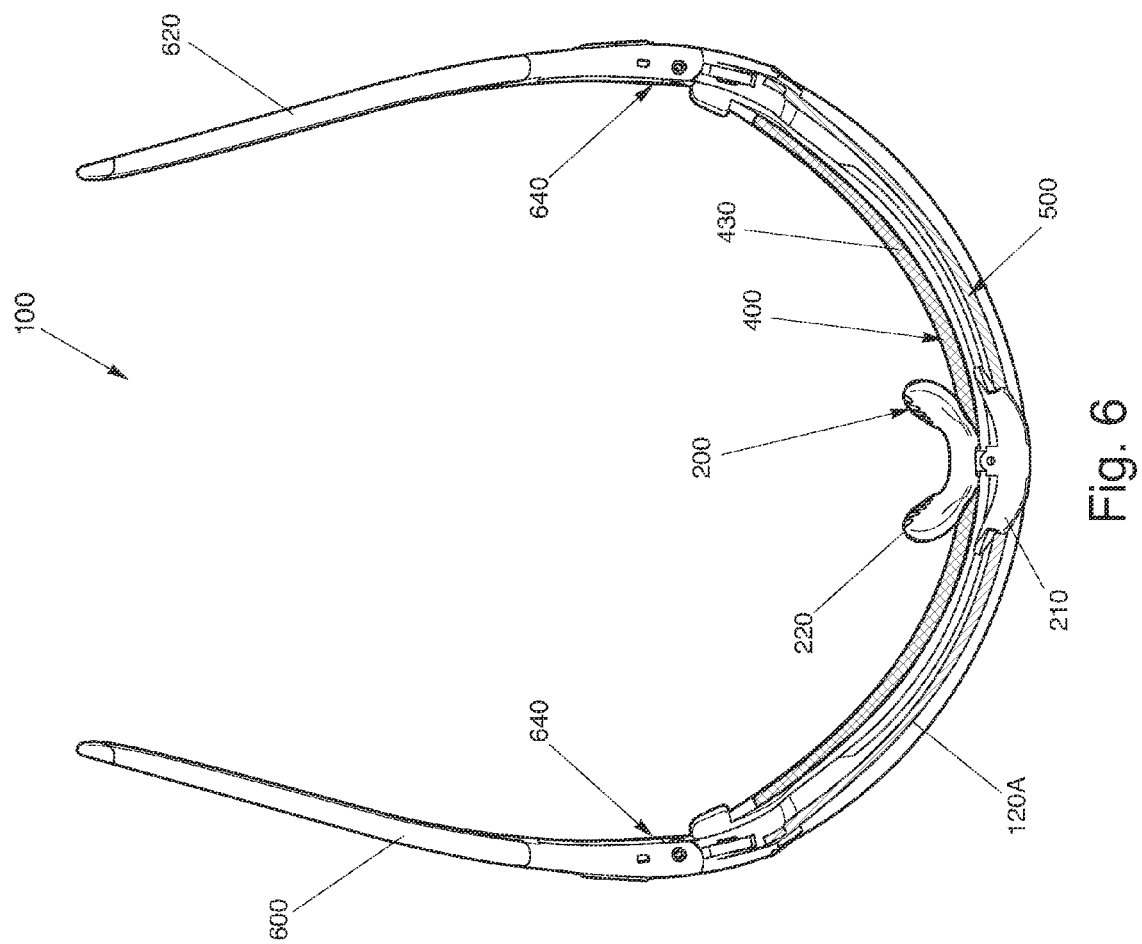
FIG. 6 is a bottom view thereof.

Now referring generally to FIGS. 1-6, the safety eyewear 100 of the instant invention is illustrated and generally indicated. As will hereinafter be more fully described, the safety eyewear 100 includes, either alone or in combination, a nose piece structure 200 with multiple axes of adjustment, a horizontal ledge 300 defined within a lens 120 of the safety eyewear 100 for attaching the nose piece structure 200, a wicking device 400 attached to the safety eyewear 100 to remove or absorb perspiration, a coloration or tinting 500 of an outer peripheral edge 120A of the lens 120 for indicating a performance characteristic of the safety eyewear 100 or the lens 120 and/or selected absorption of visible wavelengths of light, or temple bars 600, 620 of the safety eyewear 100 having adjustable width to accommodate a head of a user. By having one or more of these elements 200, 300, 400, 500, 600 of the safety eyewear 100 alone or in combination, the safety eyewear 100 provides a more versatile adjustment and better designed experience for the user, while reliably meeting national and international performance standards for impact resistance and other standards.

Referring to FIGS. 7A-14, the safety eyewear 100 of the present invention includes a nose piece structure 200 with at least one or more axes (P, Q, R) of adjustment. The nose piece structure 200 includes a nose support 210 and a nose pad 220 which are attached at a single point of attachment with a common axis. The nose support 210 generally has a substantial inverse V or U shape and is configured for attachment to a central portion of the lens 120 of the safety eyewear 10, preferably a lower central portion of the lens 120. The nose support 210 includes an inner wall 210A and an outer wall 210B to define a channel 211 between the inner 210A and outer wall 210B for seating within the central portion or a bridge area of the eyewear 10. A bottom end profile of each end of the channel generally defines an "L" shape. In one embodiment, the inner wall 210A has a height substantially greater than the height of the outer wall 210B.

The channel 211 defines one or more ledge indents 212, 213 for mating engagement with one or more horizontal ledge protrusions 312, 313 defined within the central portion of the eyewear 100. Of course, the configuration may be reversed with the channel 211 defining one or more ledge protrusions (not shown) for mating engagement with one or more horizontal ledge indents (not shown) defined within the central portion of the eyewear 100.

The inner wall 210A, closest to the nose pad 220, includes a receiving portion 230 defined on an inner surface of the inner wall 210A for receiving an insert portion 240 formed with the nose pad 220. The receiving portion 230 protrudes from the inner wall 210A along a substantially horizontal axis. The receiving portion 230 is formed near a middle area or apex of the nose support 210 adjacent a top upper edge of the nose support 210.

The receiving portion 230 having a central area 231 defining a semi-circle shape and adjacent opposing side areas 232, 233 defining generally rectangular shapes located on either side of the central area 231. In one embodiment, the height of the receiving portion 230 is approximately equal to a height of the inner wall 210A. A transverse slot 233 extends across a width of the central area 231 of the receiving portion 230 with dimensions suitable for engagement with the insert portion 240. A receiving portion aperture 234 is defined through a top area of the central area 231 and through a bottom area of the central area 231 along a vertical axis.

The nose pad 220 includes an insert portion 240. The nose pad 220 includes a wire or metal core insert (not shown) which is over molded with a soft molding or deformable material which is comfortable to a user's nose. The insert portion 240 of the metal core extends outside of the molding material along a substantially horizontal axis for insertion or engagement within the receiving portion 230 of the nose support 210. The insert portion 240 of the metal core made of material to provide adjustment along an axis of the nose piece structure 200. In one embodiment, the insert portion 240 is formed on an inner surface of the nose pad 220 and protruding from the inner surface along a substantially horizontal axis. The insert portion 240 formed near a middle area or apex of the nose pad 220 near a top edge of the nose pad 220. The insert portion 240 including a horizontal flange proportionally sized for engagement within the receiving portion 230. The insert portion aperture 244 defined through the insert portion 240 along a vertical axis. In one embodiment, the insert portion 240 generally defines a square shape but of course the invention is not limited to this particular shape.

It is important to point out the benefits of the nose pad 220 during the manufacturing process. The nose pad 220, due to its unique configuration, can facilitate the manufacturing process. In particular, the nose pad 220 includes a wire or metal core insert which is overmolded with a soft molding or deformable material. The flexibility of the nose pad 220 allows it to be molded in a flat configuration which greatly simplifies the manufacturing process.

The nose pad 220 and the nose support 210 are joined together by a variety of means with mainly a single point of attachment. The insert portion aperture 244 and the receiving portion aperture 234 are respectively positioned along a common axis when the insert portion 240 is inserted into the receiving portion 230. The receiving portion 230 and the insert portion 240 joined together by means for attachment to allow adjustment of said nose pad along an axis. For example, a fastener, such as a screw, may be vertically routed through the insert portion aperture 244 and the receiving portion aperture 234 to attach the insert portion 240 to the receiving portion 230 while permitting adjustment along one or axes. In another embodiment, a fastener is not required and the nose pad 220 and the nose support 210 are snapped together.

Figure 7A:
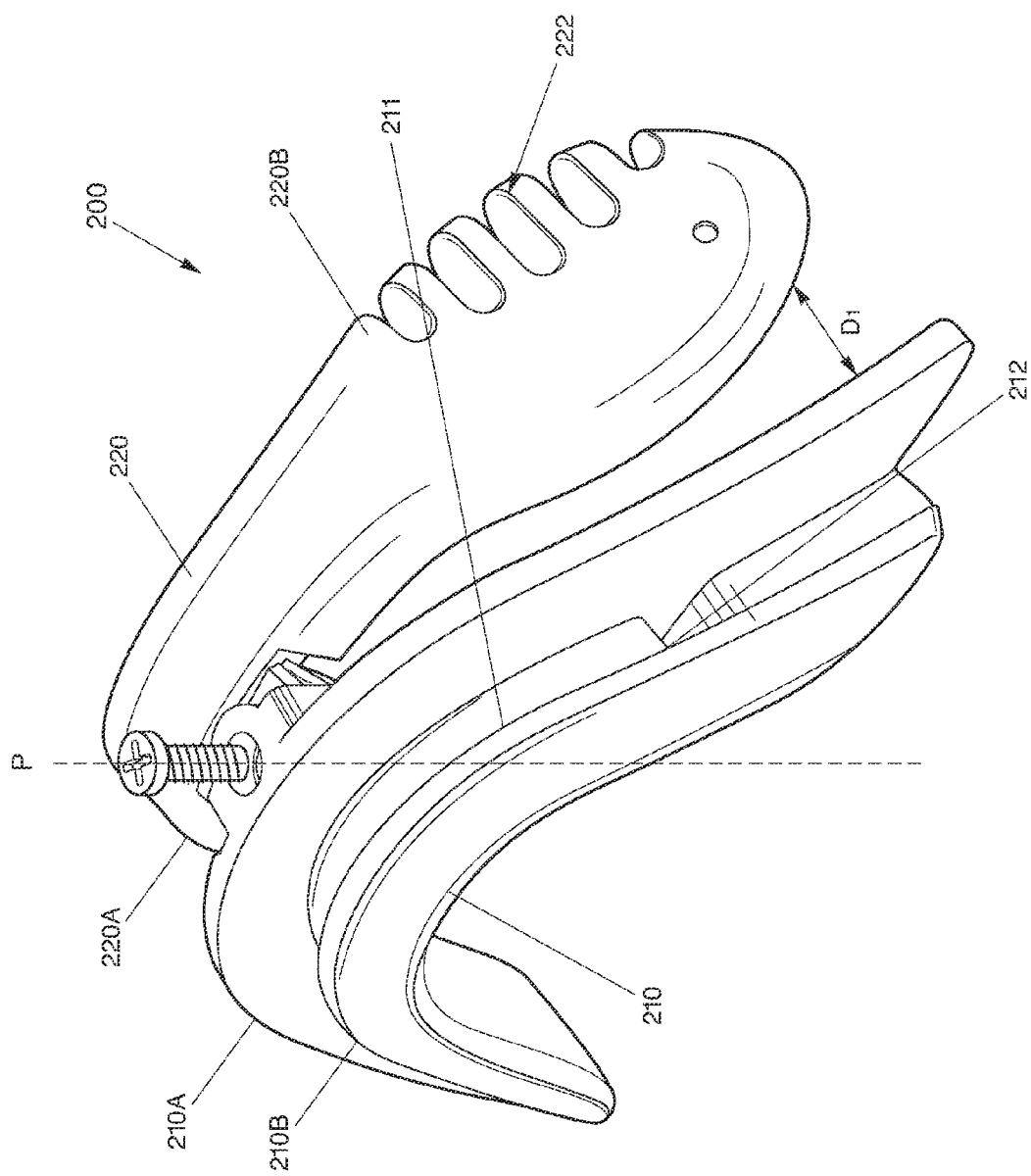
FIG. 7A is perspective view of the nose piece structure of the safety eyewear showing an example of a first position of adjustment of the nose pad relative to the nose pad mount.
Figure 7B:
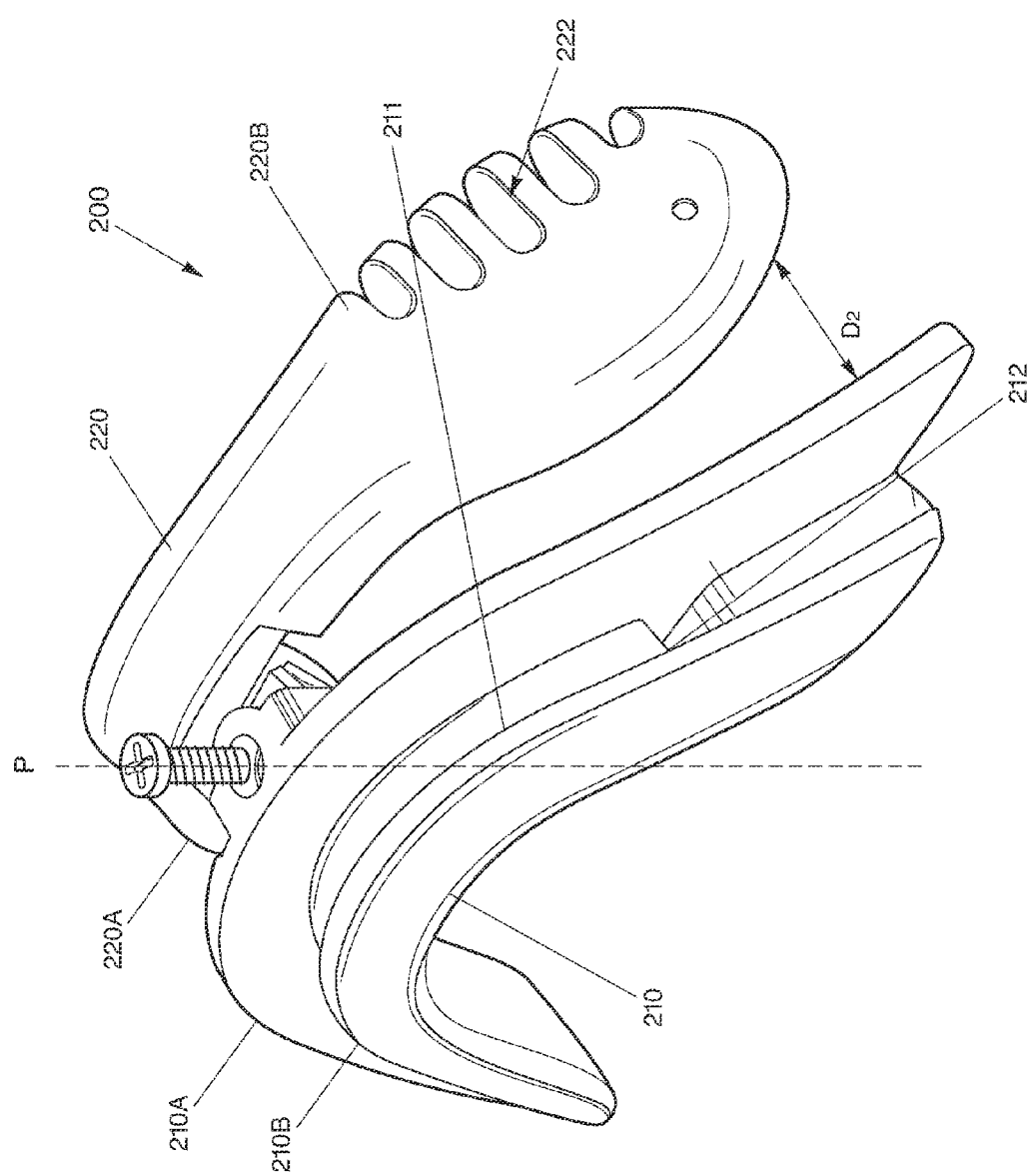
FIG. 7B is a perspective view of the nose piece structure of the safety eyewear showing an example of second position of adjustment of the nose pad relative to the nose pad mount.
Figure 8:
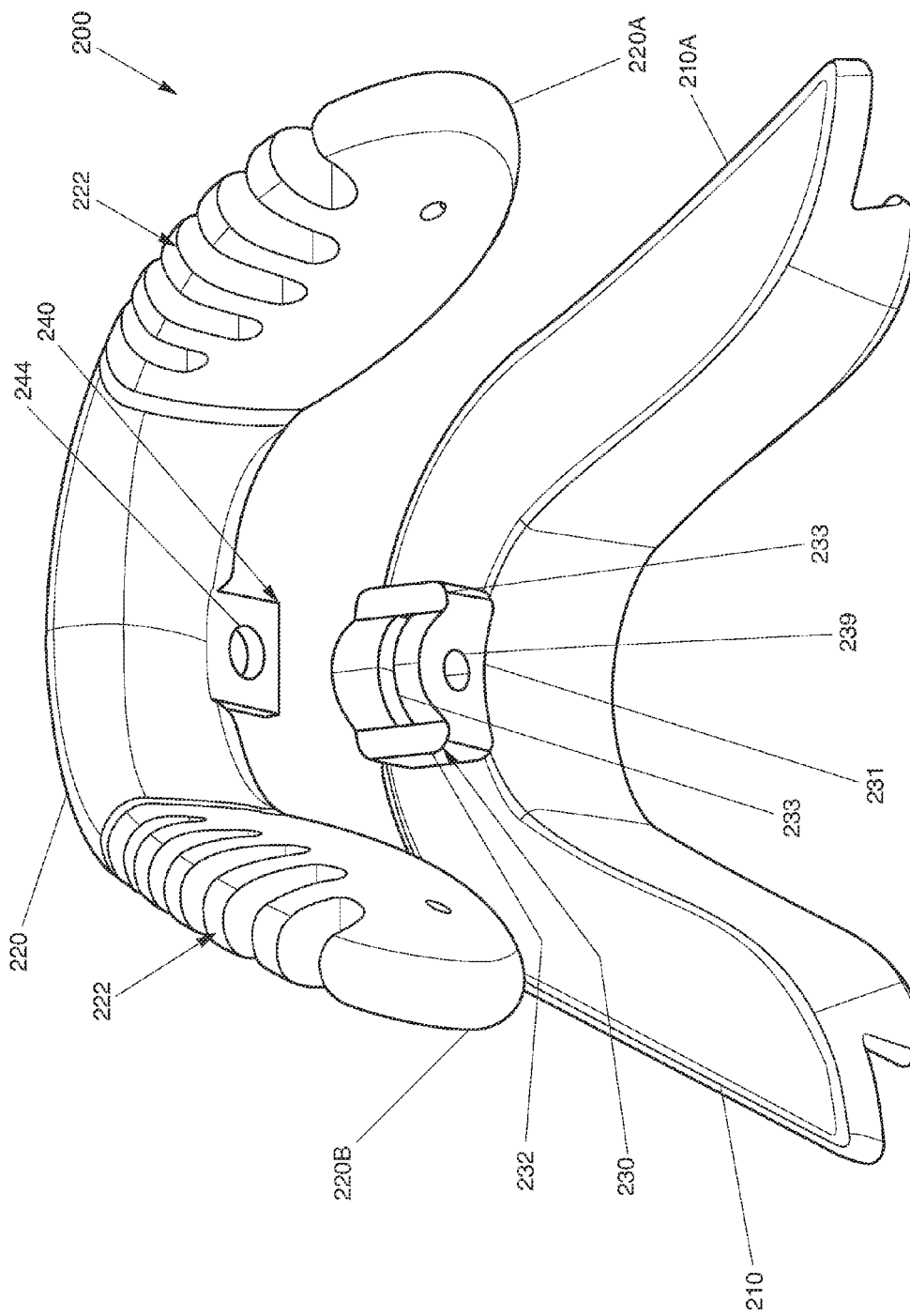
FIG. 8 is a bottom exploded view of the nose piece structure of FIG. 7A.
Figure 9:
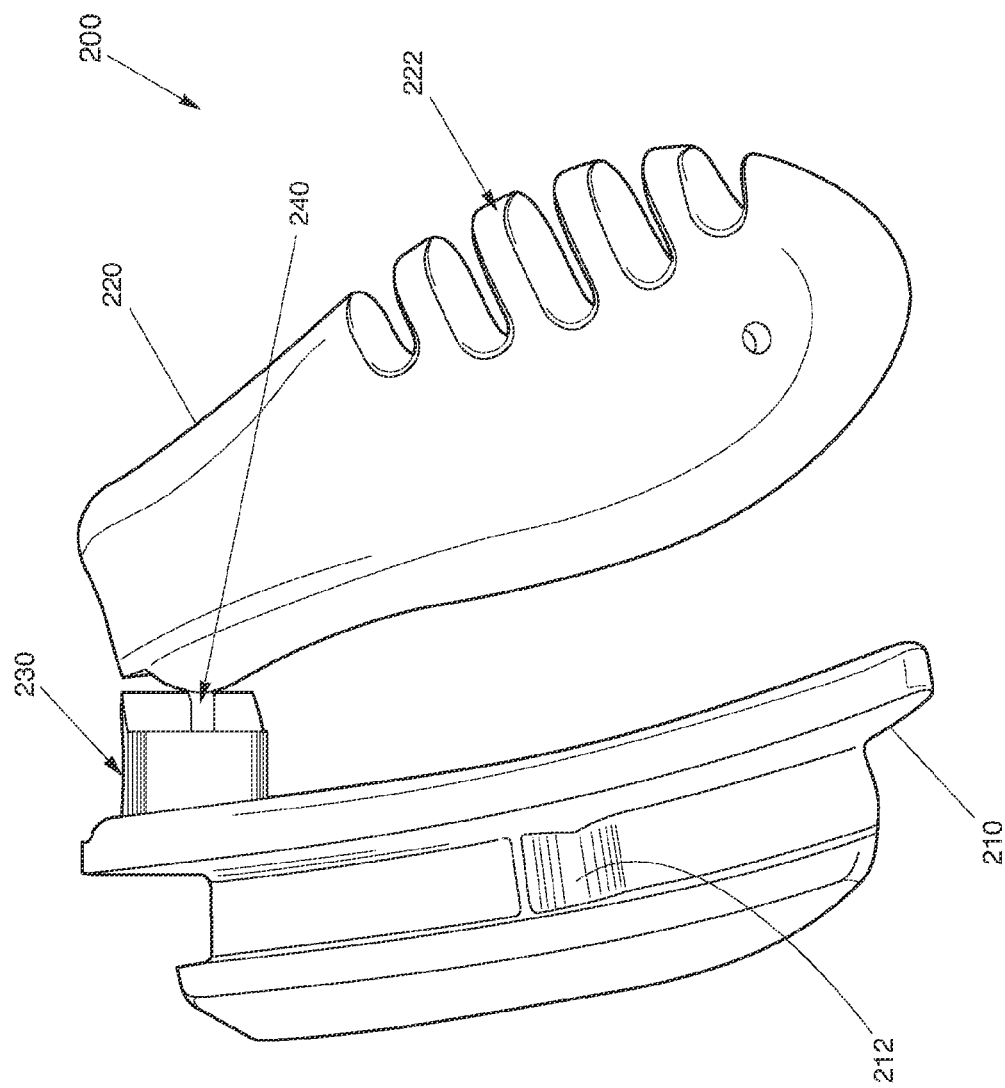
FIG. 9 is a side view of the nose piece structure of FIG. 7A.

Referring to FIGS. 7A and 7B, the nose pad 220 generally defines an inverted V or U shape with two sides 220A, 220B defining fins 222 therein along an outer surface. The nose pad 220 is movable relative to the nose support 210 along an axis P of adjustment. As illustrated in FIG. 7A, an example of a first position of the nose pad 220 relative to the nose support 210 is shown. As illustrated in FIG. 7B, an example of a first position of the nose pad 220 relative to the nose support 210 is shown. Of course, it is contemplated that nose pad 220 is movable relative to the nose support 210 to accommodate a range of user's noses having different dimensions and sizes.

The nose pad 220 has a recessed area 224 about the insert portion 240 to accommodate a range of axial movement of the nose pad 220 relative to the nose support 210. The width of the recessed area of the nose pad 220 is greater than or approximately equal to the width of the receiving portion 230. The receiving portion 230 has a recessed or cut-out area defining a semi-circle which facilitates the free movement of the nose pad 220.

Figure 11A:
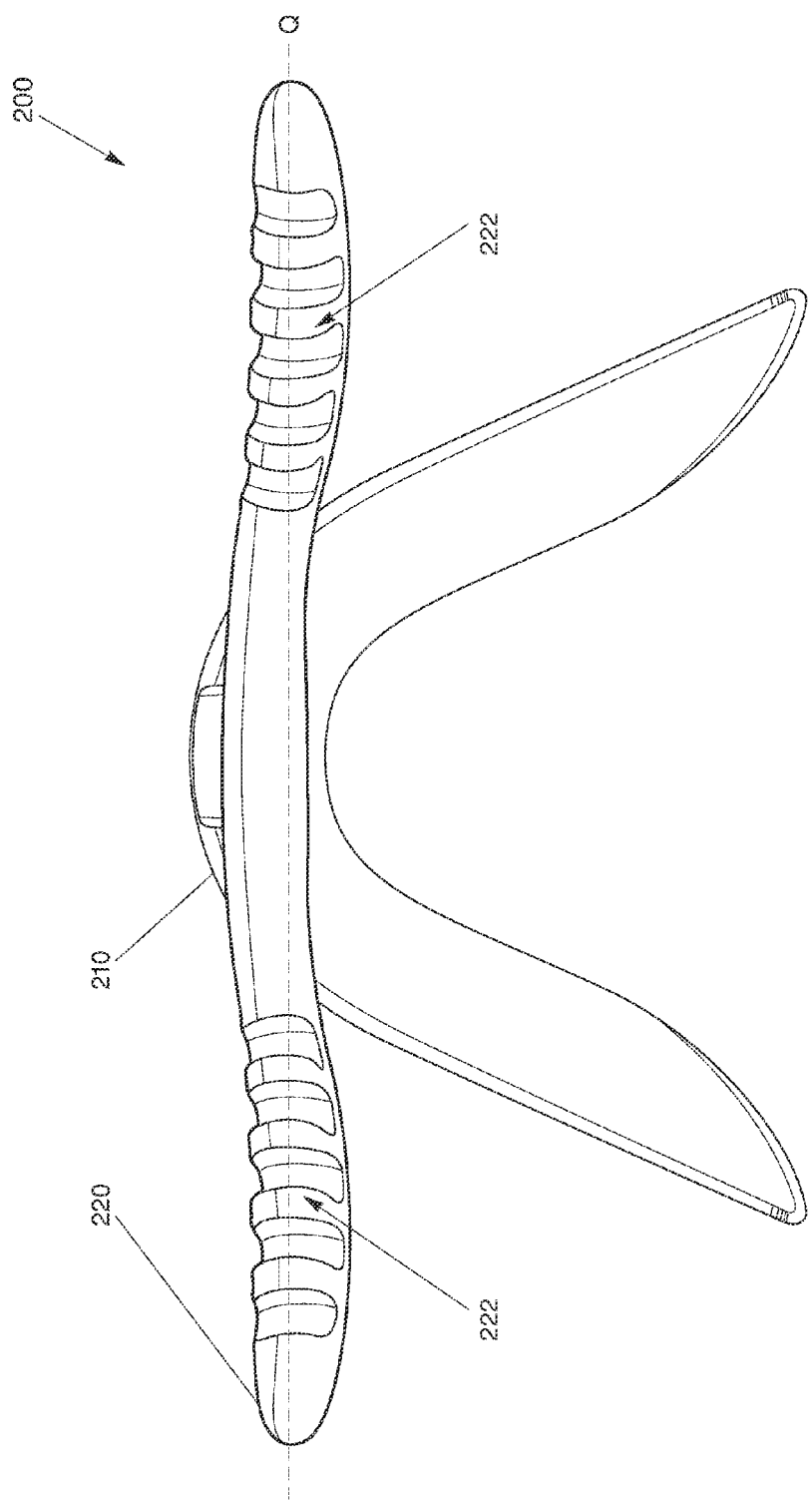
FIG. 11A is a rear view of the nose piece structure of FIG. 7A showing an example of a first position of adjustment of the nose pad along an axis.
Figure 11B:
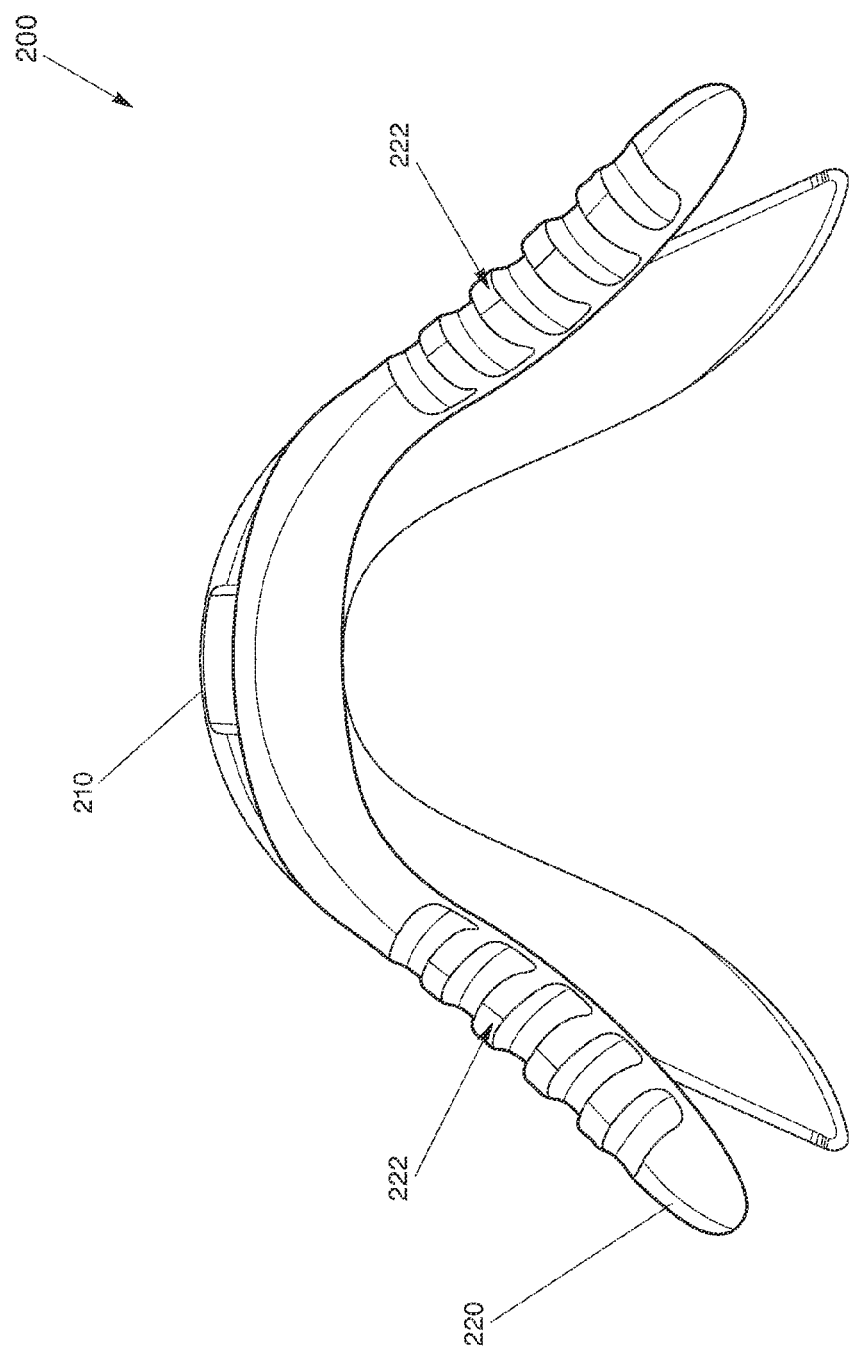
FIG. 11B is a rear view of the nose piece structure of FIG. 7A showing an example of a second position of adjustment of the nose pad along an axis.
Figure 11C:
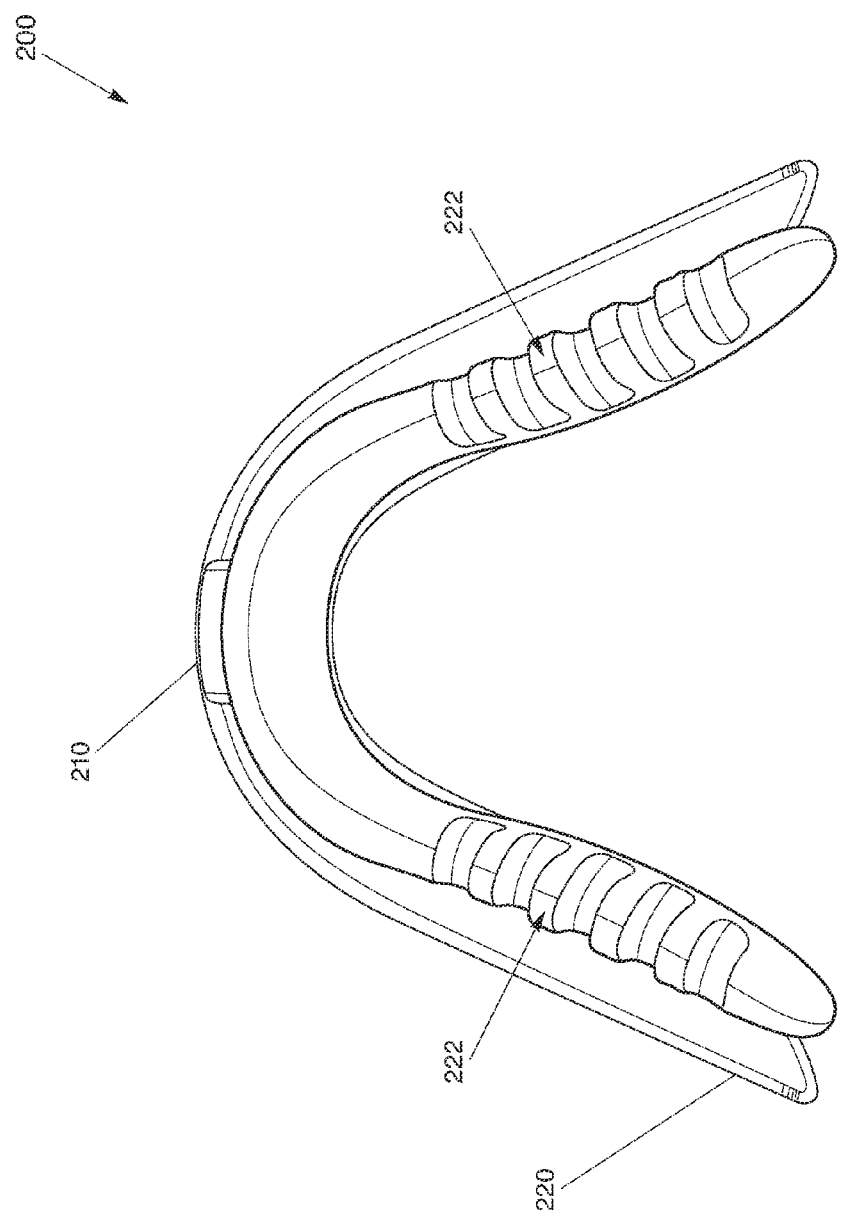
FIG. 11C is a rear view of the nose piece structure of FIG. 7A showing an example of a third position of adjustment of the nose pad along an axis.

Referring to FIGS. 11A-11C, the nose pad 220 having the two sides 220A, 220B is movable relative to one another along an axis Q of adjustment. The metal core insert (not shown) of the nose pad 220 is flexible to provide an adjustment along an axis wherein the two sides 220A, 22B are movable relative to one another. As illustrated in FIG. 11A, an example of a first position of the two sides 220A, 220B relative to one another is shown which generally defines approximately 90 degree angle. As illustrated in FIG. 11B, an example of a second position of the two sides 220A, 220B relative to one another is shown which generally defines approximately 60 degree angle. As illustrated in FIG. 11C, an example of a third position of the two sides 220A, 220B relative to one another is shown which generally defines approximately 45 degree angle. Of course, it is contemplated that the two sides 220A, 220B of the nose pad 220 are moved to an angle ranging from 0 to 360 degrees to accommodate a range of user's noses having different dimensions and sizes.

Figure 12B:
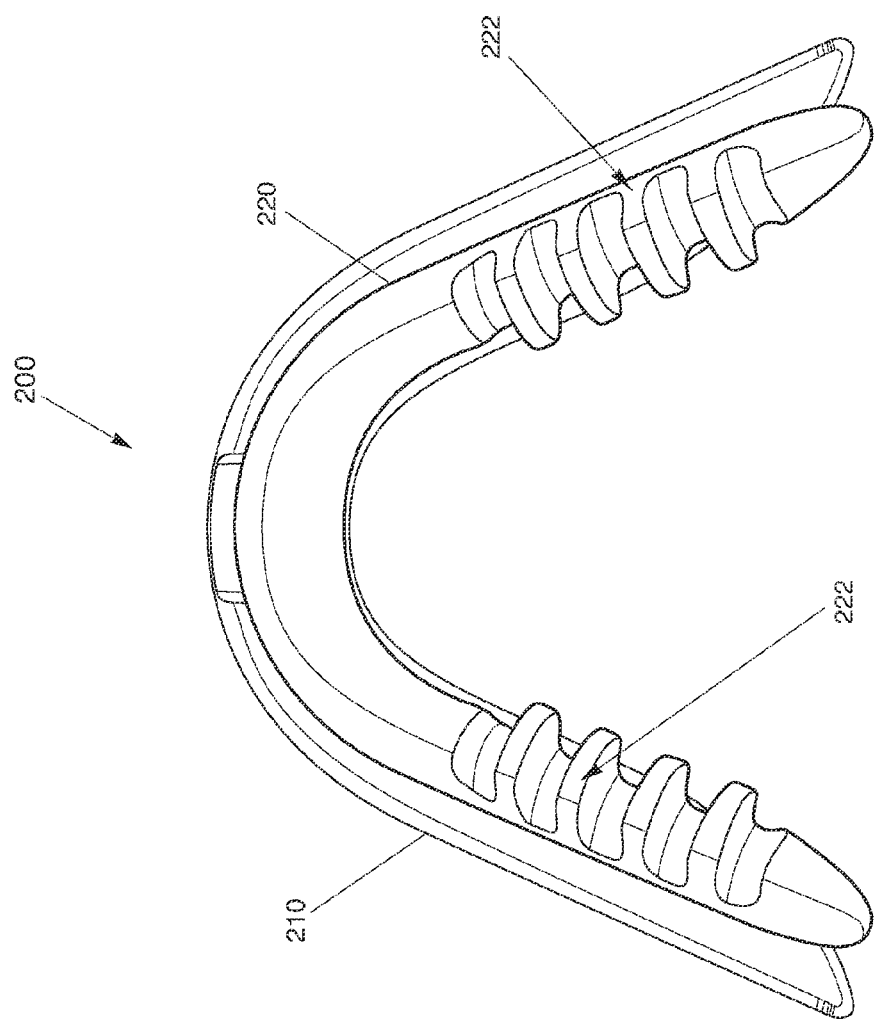
FIG. 12B is a rear view of the nose piece structure of FIG. 7A showing an example of a second position of adjustment of the fins along an axis.

Referring to FIGS. 12A and 12B, one or more fins 222 of the nose pad 220 are movable for another axis R of adjustment. In one embodiment, the fins 222 are non-uniform and defined within the outer surface of the nose pad 220. In another embodiment, the fins 222 are equally spaced apart with varying depths. For example, the fins 222 may include three fins with a similar, deeper thread and two fins with a shallow thread. The nose pad 220 defines uniform or non-uniform fins or fingers for adjustment of angle to nose to provide comfort and adjustment to the user, as well as to accommodate differing ethnic profiles. In one embodiment, at least three or more the fins 222 or fingers define a rectangular shape. Of course, it is understood that the fins 222 may define a shape other than rectangular, such as square, circular, triangular, or any other type of shape which can provide an adjustment of the angle to the nose to provide comfort and adjustment to the user. The fins 222 providing an adjustment along an axis of the nose piece 200 structure which enhances retention and slippage of nose piece structure from a user's nose. For example, as illustrated FIG. 12A, the fins 222 may be adjusted to a first position to accommodate a user's nose. In another example, as illustrated in FIG. 12B, the fins be adjusted to a second position to accommodate a user's nose. Of course, it is contemplated that an angle range different from those examples may be used to accommodate a range of user's noses having different dimensions and sizes.

Figure 13:
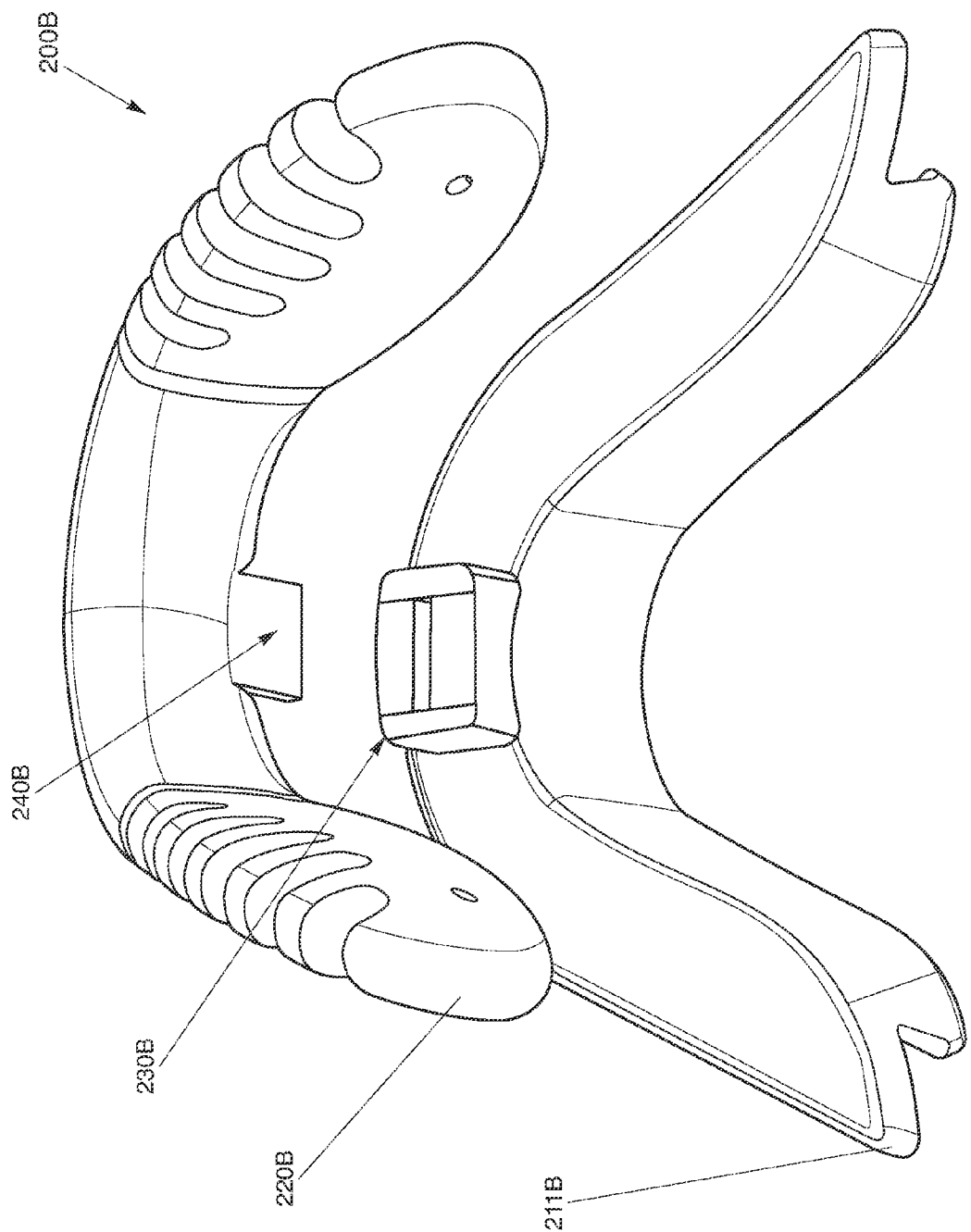
FIG. 13 is bottom exploded view of an alternative embodiment of FIG. 7A.

Referring to FIG. 13, an alternative embodiment 200B of the nose piece structure 200 is illustrated. The nose piece structure 200B generally includes a nose support 210B and a nose pad 220B similar to nose piece structure 200 except for the insert portion 240B and the receiving portion 230B. The insert portion 240B defines a tab or flange extending from the nose pad 220B. The receiving portion 230B generally defines a square shape with a slot therein for receipt of the tab or flange. There insert portion 240B snaps into the receiving portion 230B at a single point of attachment to secure the nose pad 220B to the nose support 210B.

Figure 14:
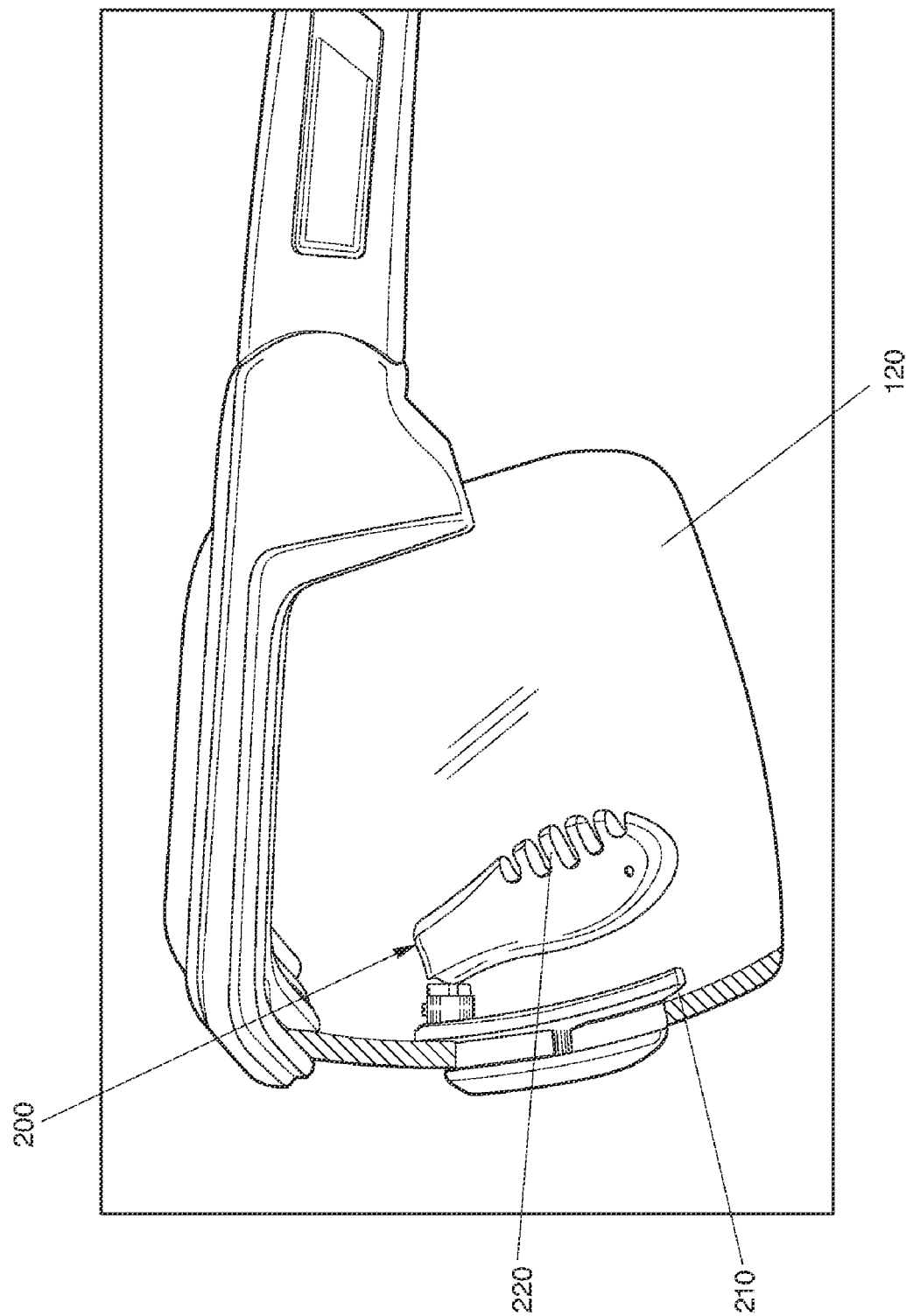
FIG. 14 is a side view of the nose piece structure of FIG. 7A attached to the safety eyewear.
Figure 16:
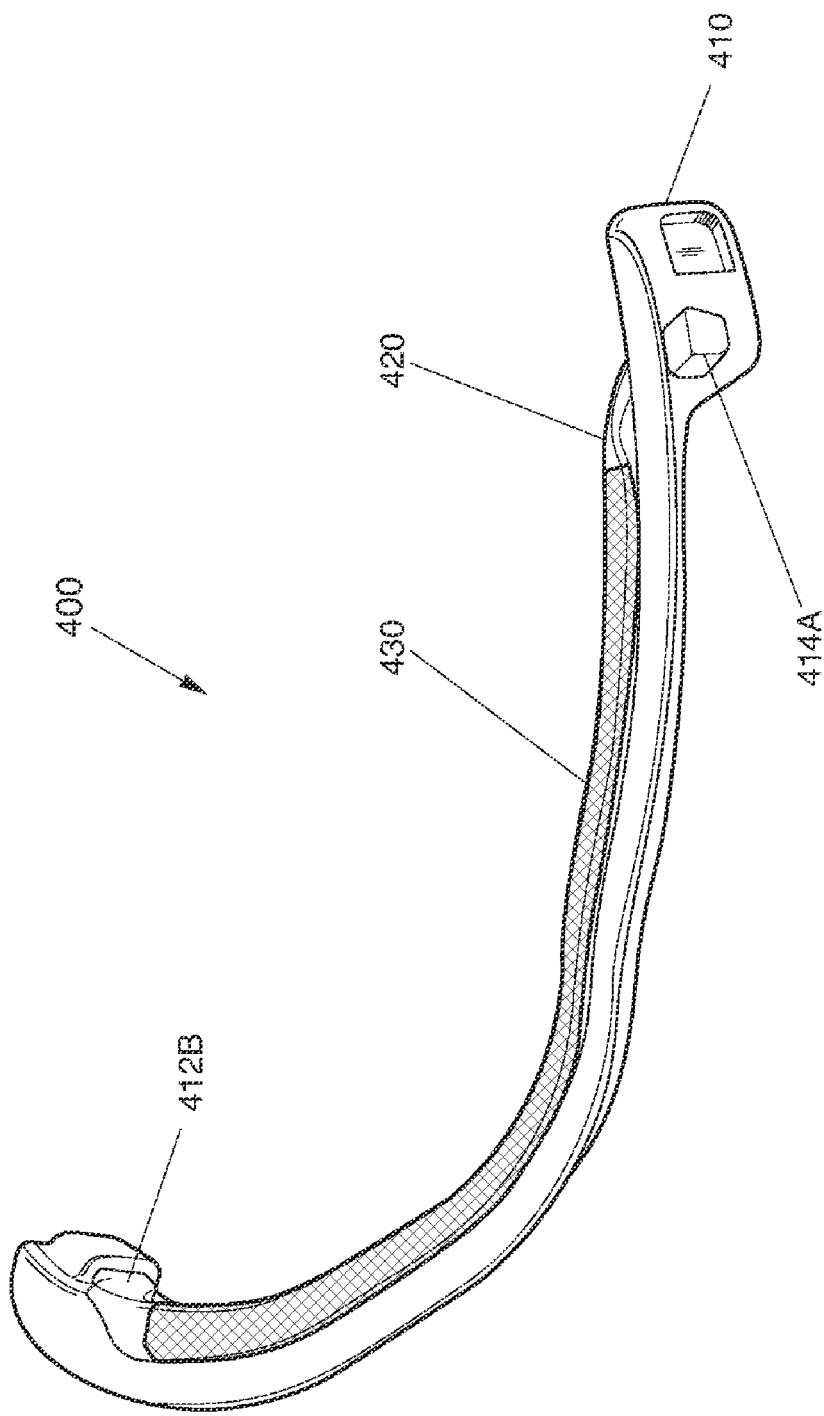
FIG. 16 is a front perspective view of the wicking device of the safety eyewear.
Figure 17:
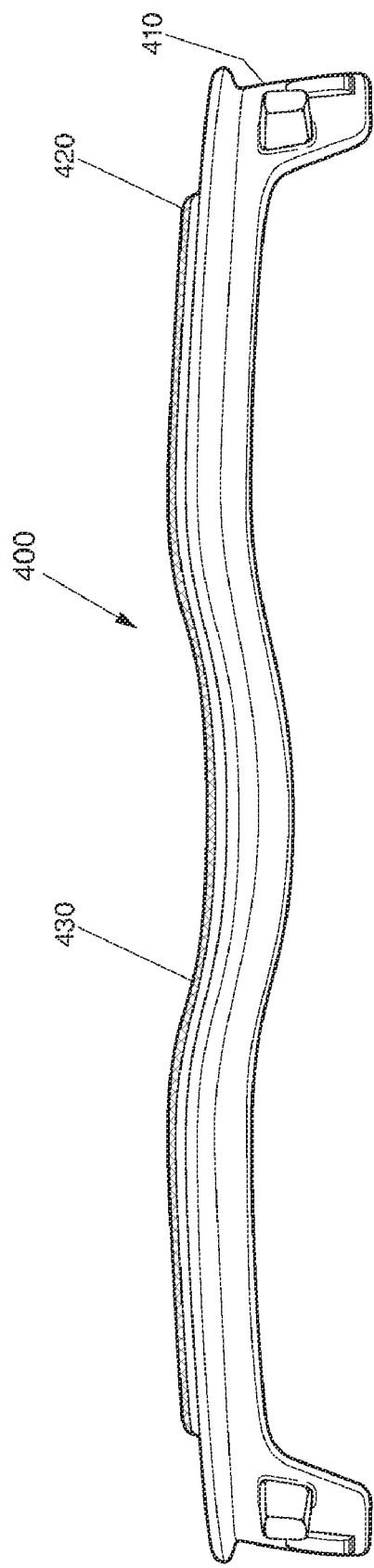
FIG. 17 is a front view thereof.
Figure 18:
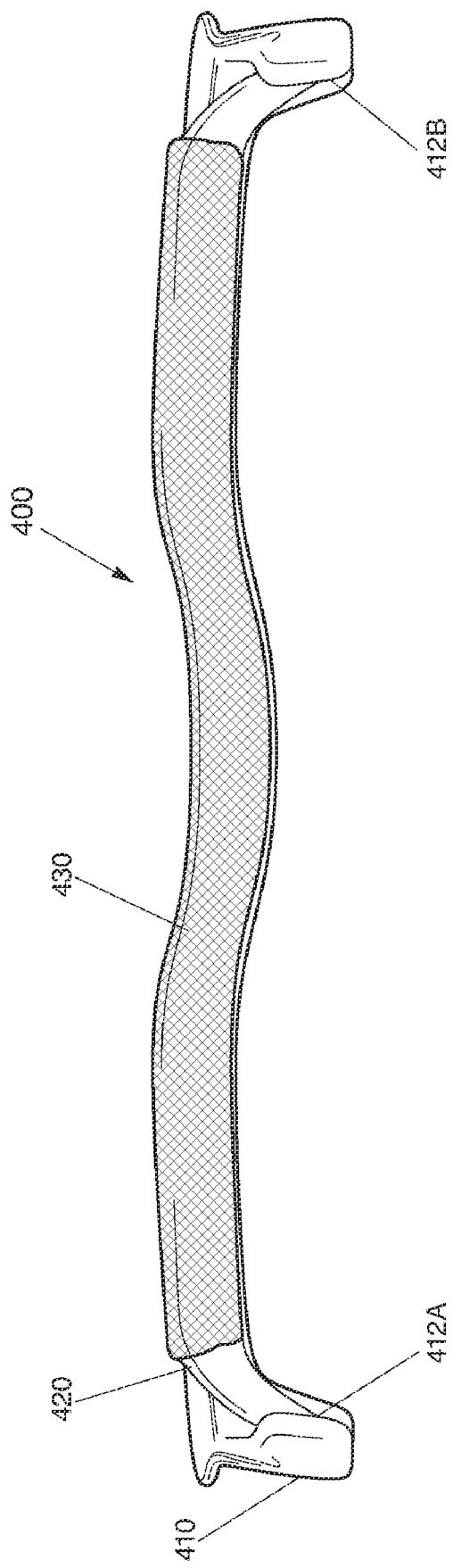
FIG. 18 is a rear view thereof.
Figure 19:
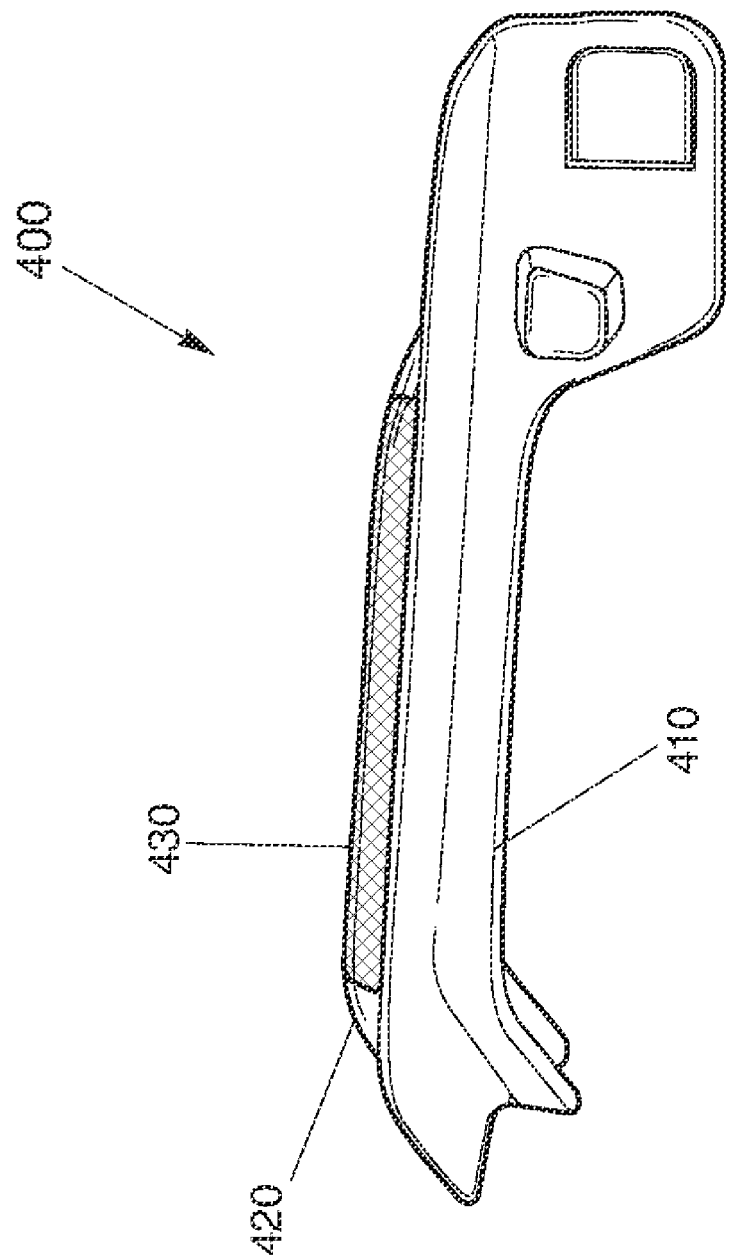
FIG. 19 is a left view thereof, the right view is a mirror image thereof.
Figure 20:
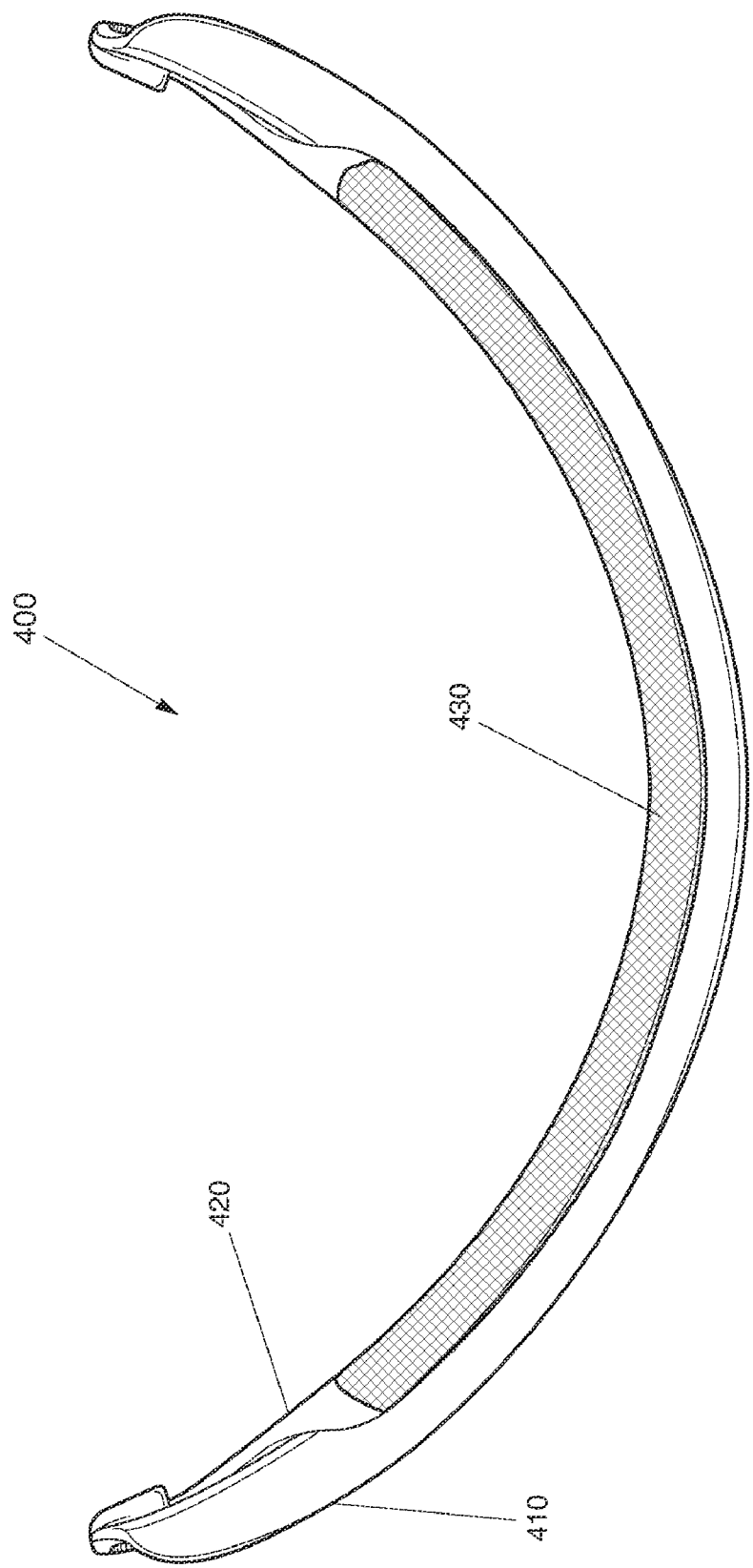
FIG. 20 is a top view thereof.
Figure 21:
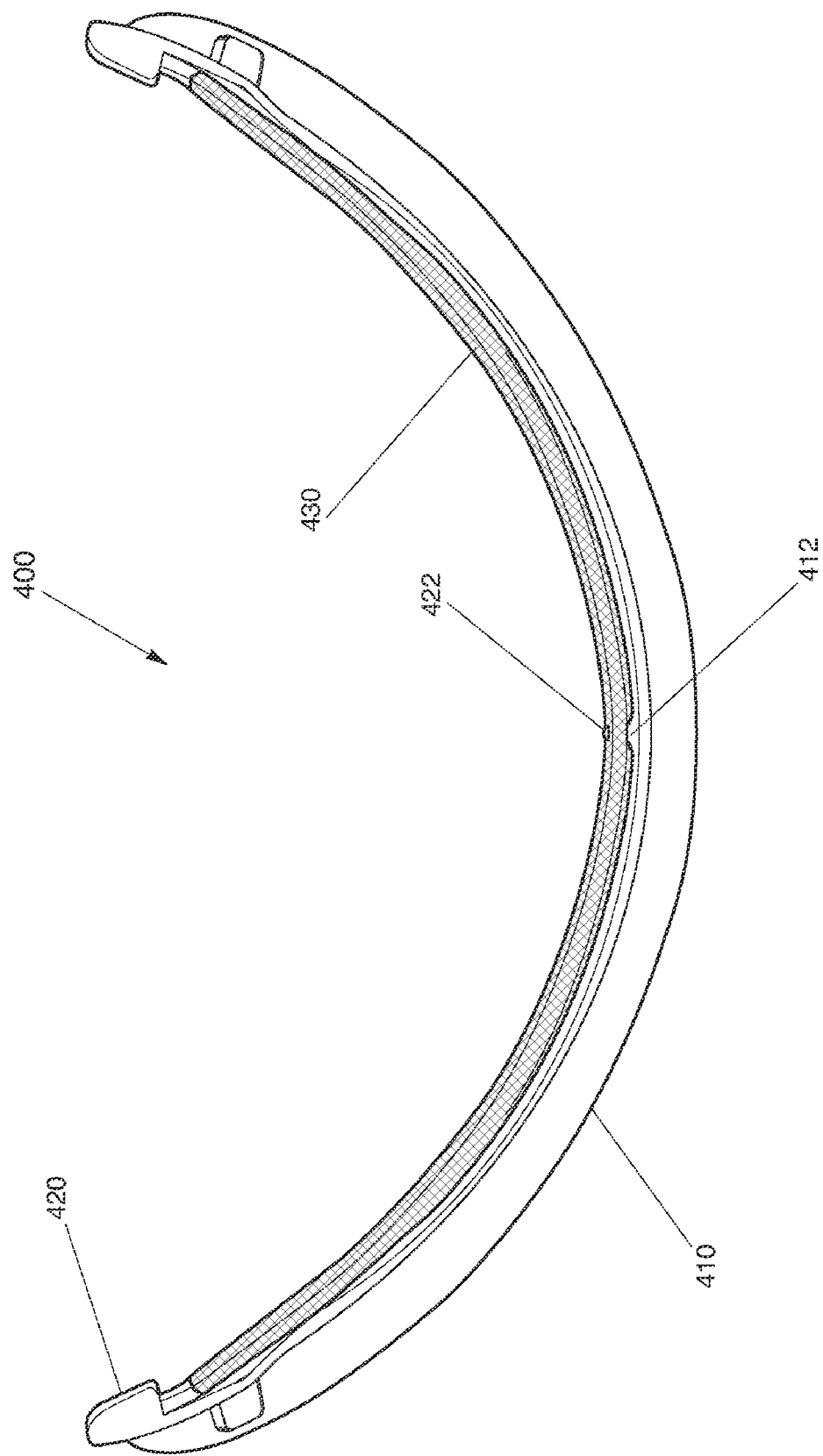
FIG. 21 is bottom view thereof.
Figure 22:
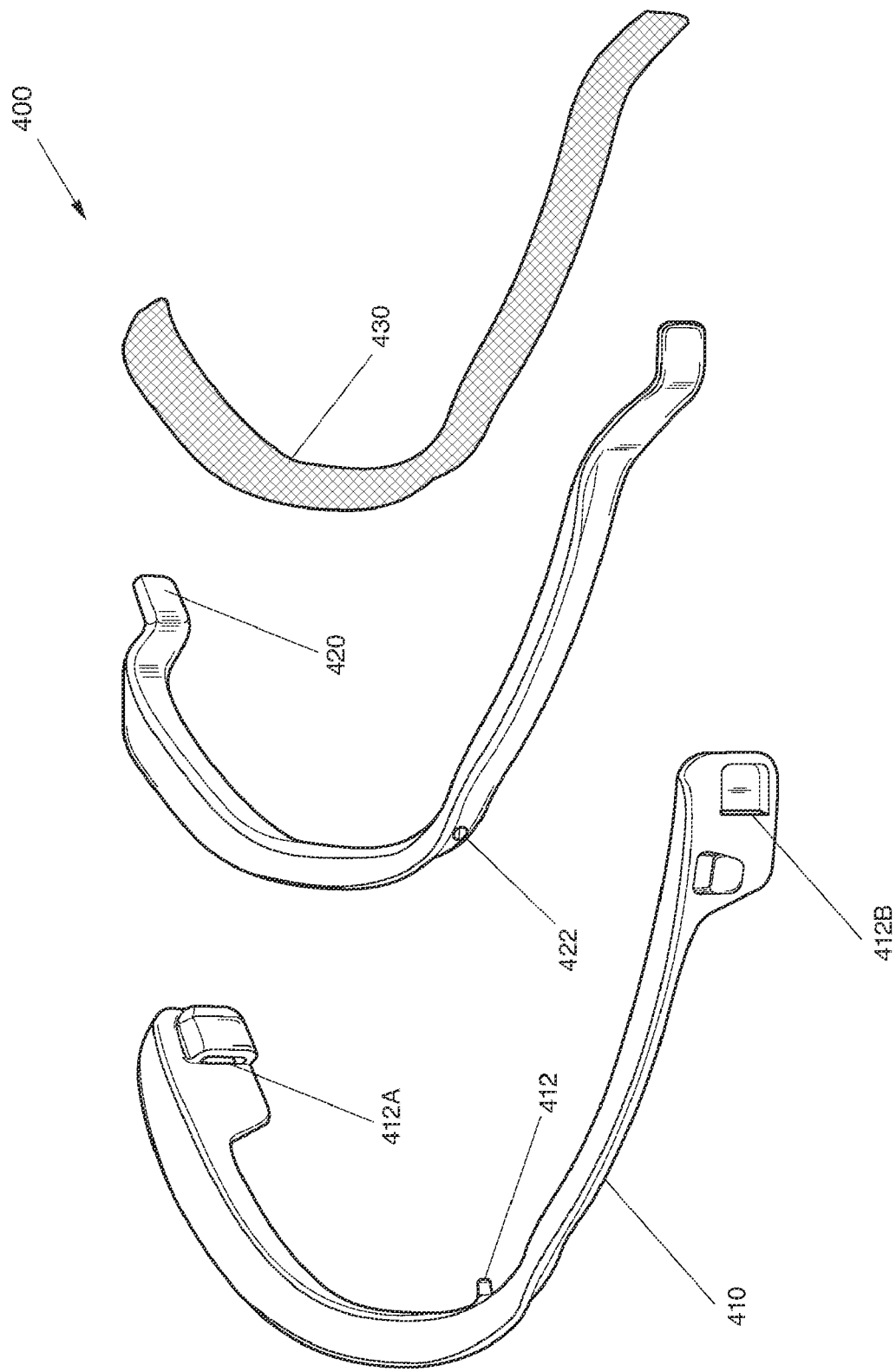
FIG. 22 is an exploded view of the wicking device of FIG. 16.
Figure 25B:
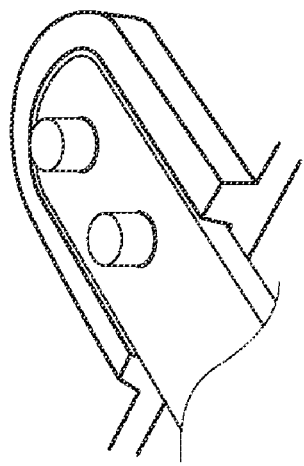
FIG. 25B is a perspective view of another example of a snap mechanism for connecting the wicking bar to the wicking sub-frame.
Figure 25C:
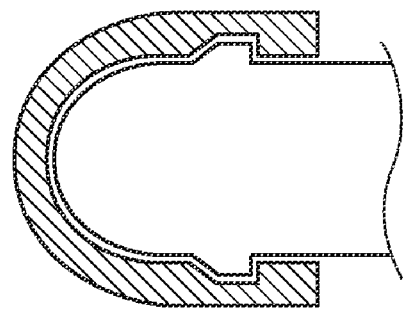
FIG. 25C is a perspective view of another example of a snap mechanism for connecting the wicking bar to the wicking sub-frame.
Figure 25A:
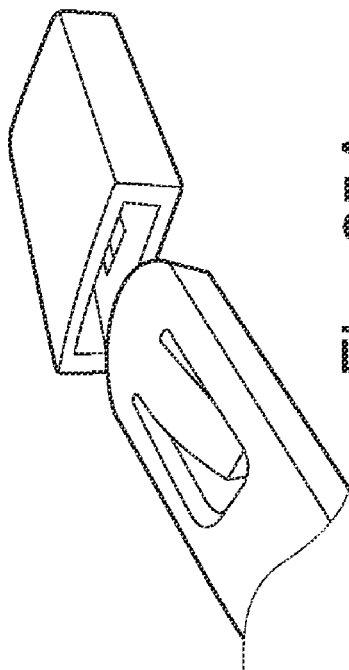
FIG. 25A is a perspective view of an example of a snap mechanism for connecting the wicking bar to the wicking sub-frame.
Figure 28:
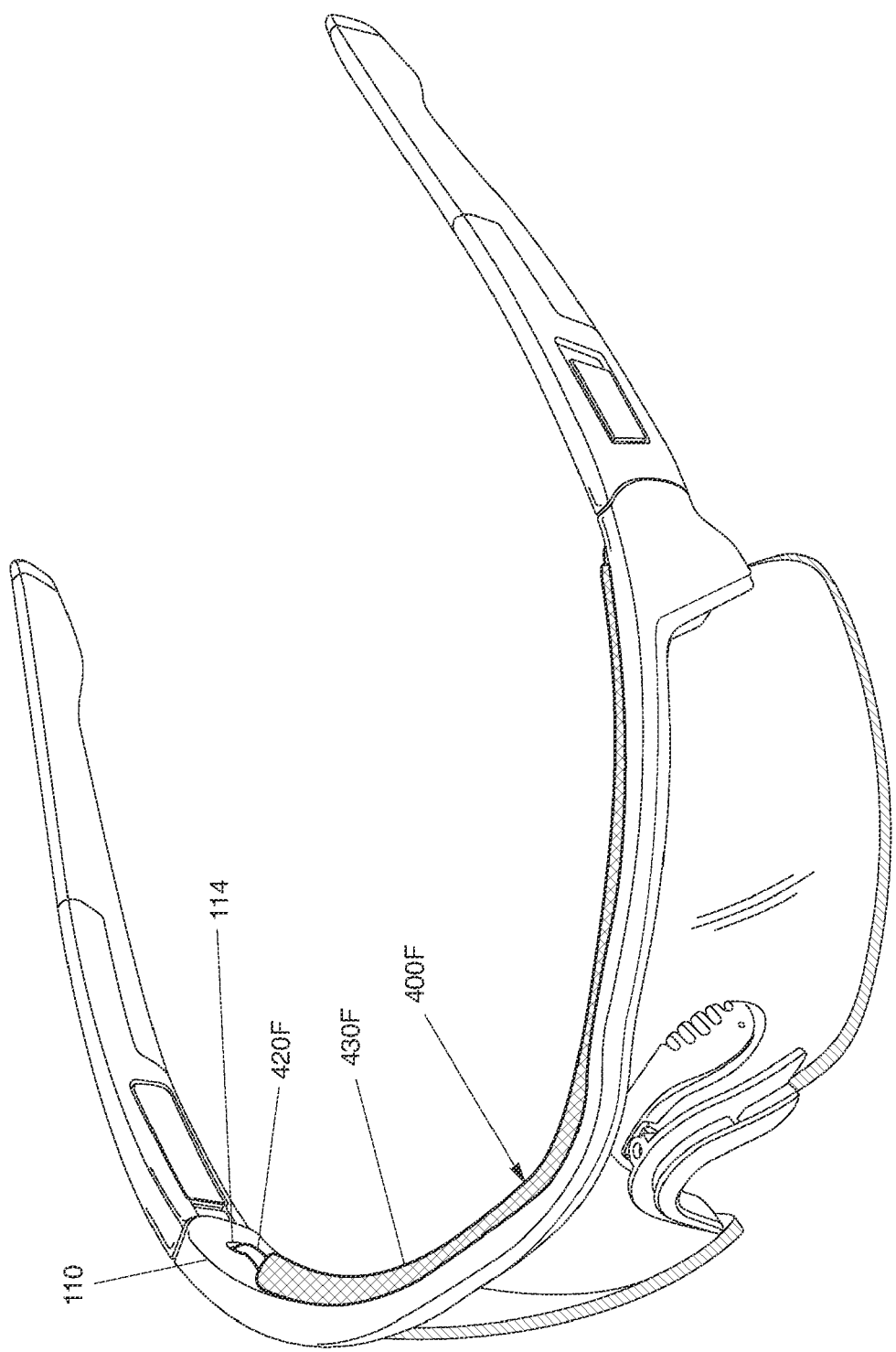
FIG. 28 is a perspective view of another embodiment of the wicking device.
Figure 29:
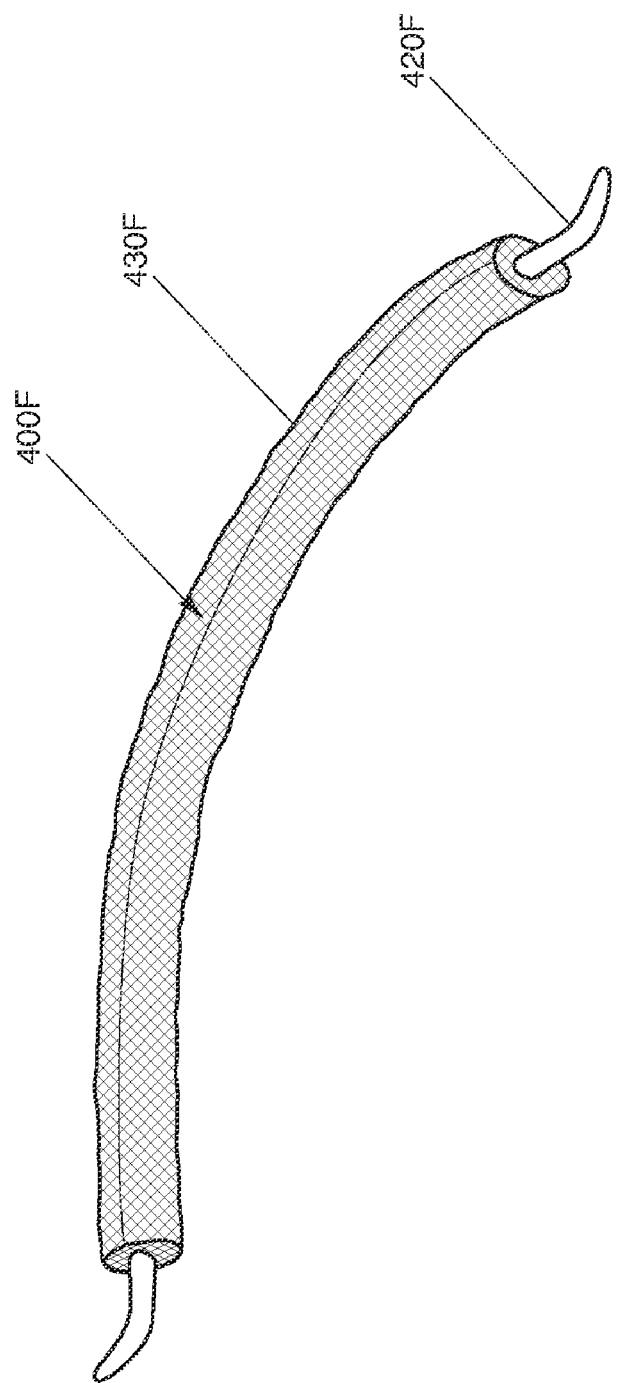
FIG. 29 is a perspective view of the wicking bar and wicking material of FIG. 28.
Figure 30:
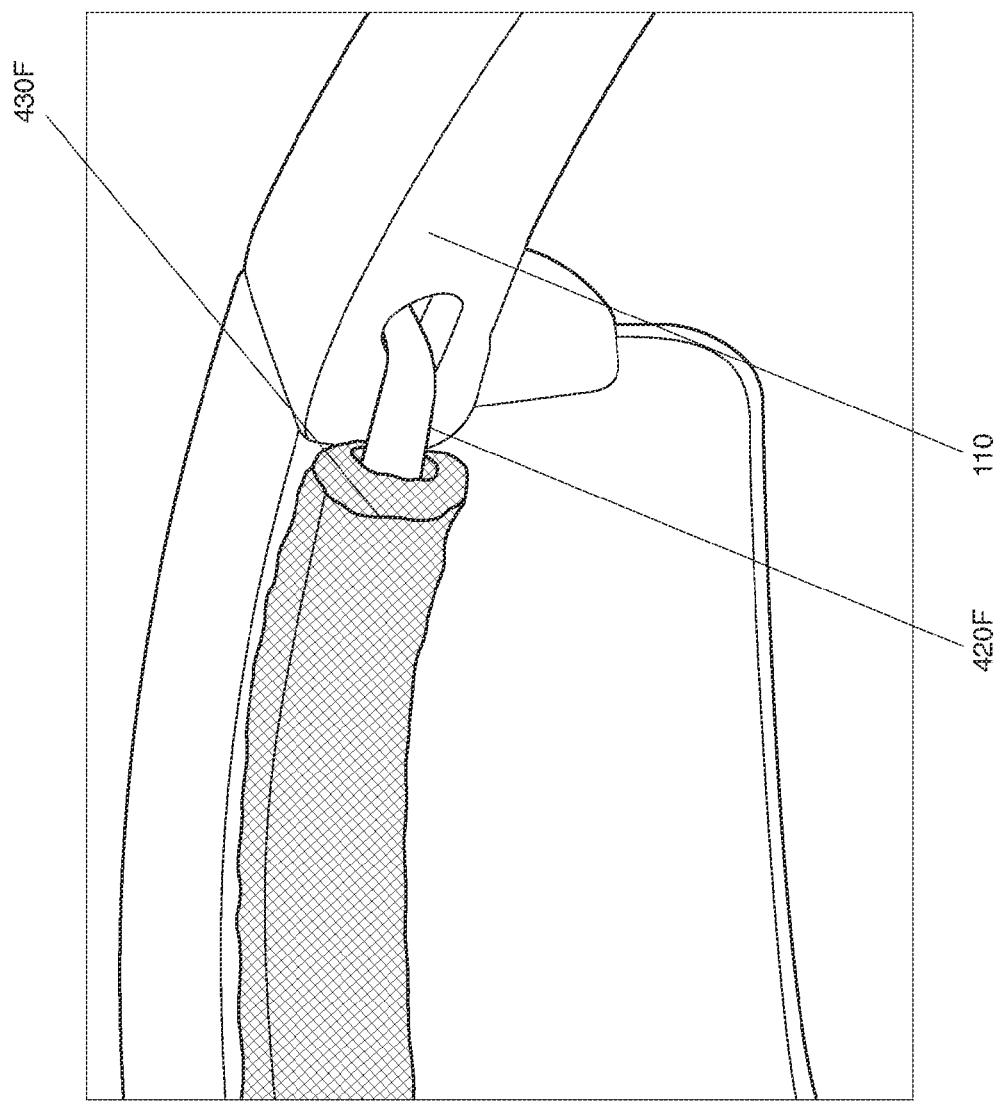
FIG. 30 is a partial view of the wicking bar of FIG. 29 directly attached to the frame.
Figure 31:
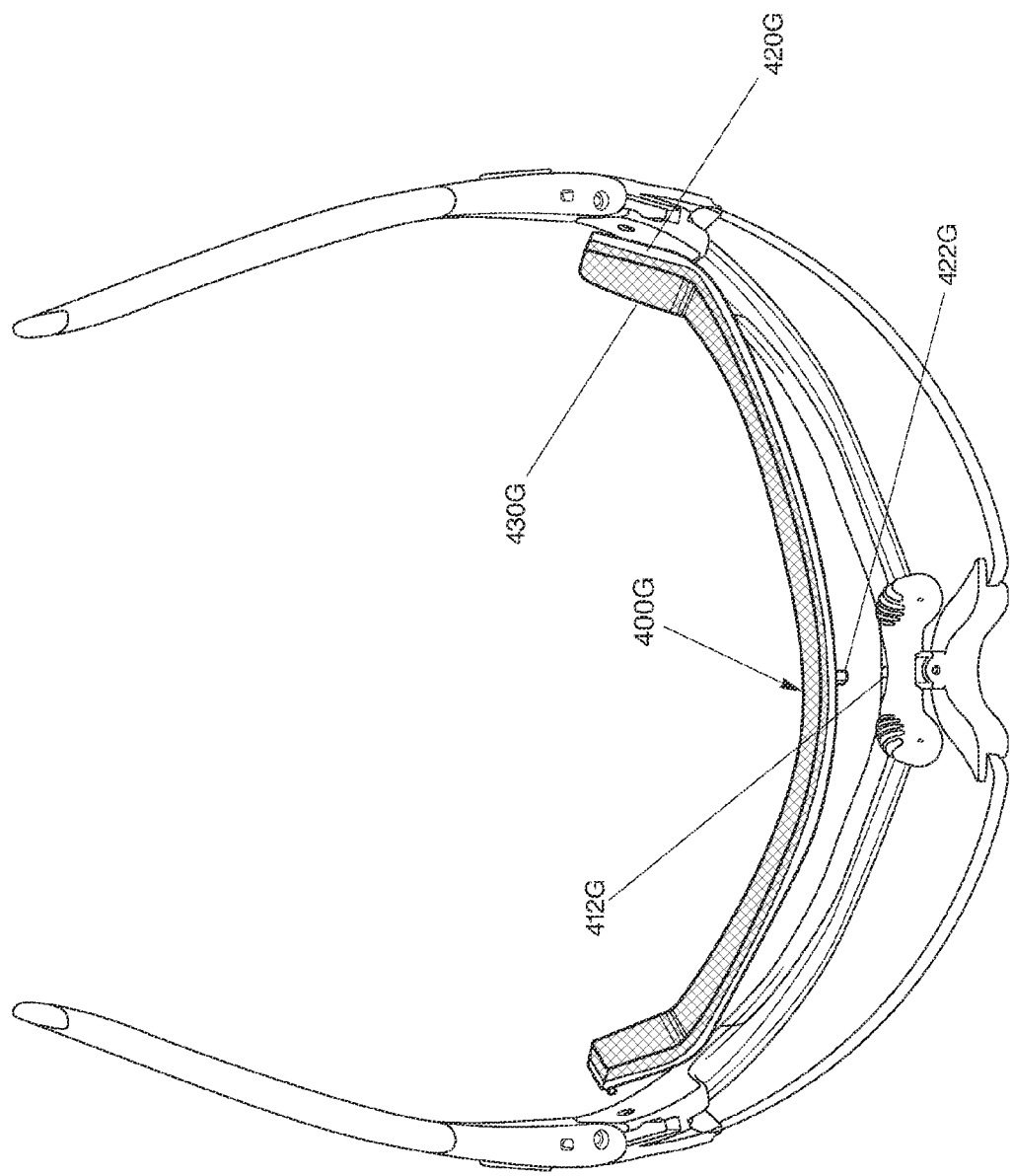
FIG. 31 is a perspective view of another embodiment of the wicking device.

Referring to FIG. 14, in operation, the nose piece structure 200 is attached to the central portion of the lens 120 of the safety eyewear 100. The central portion of the safety eyewear 100 being inserted in and between the inner 210A and the outer wall 210B of the nose support 210 until the horizontal ledge protrusions 312, 313 defined within the lens 120 engages the ledge indents 212, 213 defined within the channel 211 of the nose support 210. Once the nose piece structure 200 is attached to the central portion of the lens 120, the nose piece structure 200 can be adjusted along more than one axis. For example, an axis of adjustment is the movement of the two sides 220A, 220B of the nose pad 220 relative to one another. Another axis of adjustment is the movement of the fins 222 defined within the nose pad 220. Also, another axis of adjustment is the movement of the nose pad 220 relative to the nose support 210. Overall, the nose piece structure 200 allows for multiple axis of adjustment in at least a vertical or horizontal plane. It should be noted that the nose pad 220, the fins 222, and the two sides 220A, 220B, may be moved along any axis, any angle from 0 to 360 degrees, or in any direction relative to the nose support 210 to provide comfortable fit to a user.

Referring to FIGS. 15A and 15B, the safety eyewear 100 of the present invention includes a lens 120 having at least one horizontal ledge 300, 302 for securing the lens 120 to the nose piece structure 200. The safety eyewear 100 includes a frame 110, the lens 120, and at least one temple bar 600, 620 hingedly connected to the frame 110. The nose-piece structure 200 includes a nose pad 210 and a nose support 220. The nose piece structure 200 is configured for permanent or releasable attachment to a central portion of the lens 120.

The horizontal ledge 300, in one embodiment, defines horizontal ledge protrusions 312, 313 or bumps on the lens 120 for mating engagement with ledge indents 212, 213 defined within the channel 211 of the nose piece structure 200. The central portion, or preferably the lower central portion of the lens 120, defines horizontal ledge protrusions 312, 313 for engagement within the ledge indents 212, 213 when the nose piece structure 200 and the lens 120 are attached or snapped together.

In one embodiment, the central portion of the lens 120 has a recessed area 314 that includes two horizontal ledges 300, 302. The recessed area 314 of the lens defines an inverted V-shape or U-shape and is formed in the lower central portion of the lens 120. The recessed area 314 includes a perimetral edge 316 or outermost edge. At least one more opposing, horizontal ledge protrusions 312, 313 extend inwardly from the perimetral edge 316. Each protrusion 312, 313 defines a first horizontal ledge 300 and a second horizontal ledge 302. The first horizontal ledge 300 and the second horizontal ledge 302 including a substantially horizontal projection 300A, 302, forming a narrow shelf on the lens 120 for engaging with the ledge indents 212, 213 of the nose-piece structure 200. A ledge support area 300B, 302B for both the first and second horizontal ledges 300, 302 extends along a downward slope towards a bottom end of the recessed area 314. Each ledge support area 300B, 302B defines a gradual declining portion and a less gradual or steeper declining portion. The first horizontal ledge 300 and the second horizontal ledge 300 substantially aligned along a common, horizontal ledge axis S.

A top portion 314A of the recessed area 314 extends above the common, horizontal ledge axis S. In one embodiment, the top portion 314A of the recessed area 314 has a mushroom-shape. More importantly, the top portion 314A of the recessed area 314 provides a sufficient clearance area to allow for ledge indents 212, 213 within the channel 211 of the nose support 210 to clear a corner of the horizontal ledge 300, 302. The nose support 210 has ledge indents 212, 213 which are proportionally sized to snap over the horizontal ledges 300, 302.

A bottom portion 314B of the recessed area 314 extends below said common, horizontal ledge axis S. The bottom portion 314B includes a height fifty percent or more than the height of the top portion 314A of the recessed area 314. The width of the bottom portion 314B increases from the common horizontal ledge axis S to a bottom end of the recessed area 314. The width of the bottom end of the recessed area 314 is fifty percent or more than the height of the bottom portion 314A or the top portion 314B.

When the ledge indents 212, 213 of the nose piece structure 200 engages the horizontal ledge protrusions 312, 313 of the lens 120, the nose piece structure 200 has a more secure connection to the lens 120. Of course, the configuration may be reversed with the channel 211 defining one or more ledge protrusions (not shown) for mating engagement with one or more horizontal ledge indents (not shown) defined within the central portion of the eyewear 100.

Referring to FIGS. 16-32D, the safety eyewear 100 of the present invention includes a wicking device 400 or assembly for releasable attachment to the eyewear frame 110 for removing moisture or sweat from or near the eyewear 100.

The wicking device 400 includes one or more of the following: a wicking sub-frame 410, a wicking bar 420, and an absorbent or wicking material 430 attached to either the wicking bar 420 or the wicking sub-frame 410. In one embodiment, the wicking sub-frame 410 is attached to the eyewear 110, the wicking bar 420 is attached to the wicking sub-frame 410, and the wicking material 430 is attached to the wicking or brow bar 420. The sub-frame 410 and brow bar 420 define mating shapes for interlocking into one another which secures the sub-frame 410 to the brow bar 420. Note, there are numerous configurations of the wicking device 400 which will be further discussed below.

The wicking sub-frame 410 has a proximal and a distal end and is removably or permanently attached to the eyewear frame 110. In a preferred embodiment, the wicking sub-frame 410 or wicking bar 420 is removably attached at the end pieces 110A, 110B of the frame 110. In one embodiment, the wicking sub-frame 410 is a single piece plastic bar defining an "L shape which follows the contour of the top and inner periphery of the brow area of the frame 110. A portion of the wicking sub-frame 410 contacts or engages the frame 110 along an inner periphery or top of the brow area of the frame 110. In particular, the wicking sub-frame 410 has a length sufficient to accommodate the length of the brow bar 420.

The wicking sub-frame 410 may define apertures, recesses, slots, or other receiving portions 412A, 412B at a distal and proximal ends of the sub-frame 410 to allow the brow bar 420 to be inserted therein for securing purposes. Of course, the sub-frame 410 may also include protrusions, extensions, hooks, or other insert portions 412 for engaging a receiving portion 422 of the brow or wicking bar 420 for securing the sub-frame 410 to the frame 110.

The sub-frame 410 may also include recesses, slot, apertures, or other receiving portions at the proximal and distal ends for receiving an insert portion of the frame 110 for securing the sub-frame 410 to the frame 110. Of course, the sub-frame 410 may also include protrusions, extensions, hooks, or other inserts portions 414A, 414B at the proximal and distal ends for engaging a receiving portion of the frame 110 for securing the sub-frame 410 to the frame 110. In one embodiment, the sub-frame 410 may snap into the inner frame 110 of the eyewear 100 or by other methods known in the art.

Referring to FIGS. 23A-32D, there are a variety of methods for removably attaching or releasably securing the proximal and distal ends of the sub-frame 410 to the wicking bar 420. In one embodiment, the wicking sub-frame 400B includes injection molded plastic end pieces 410B with a locking or snap mechanism 411B therein. The injection molded end pieces 410B provide a locking or snap mechanism 411B for inserting the wicking bar 420. The locking mechanism may include a Tinnerman (FIG. 25A), S-wedge post (FIG. 25B), or a snap mechanism (FIG. 25C) as illustrated. Once the wicking bar 420B is inserted into the locking mechanism 411B, a lock releasably or permanently secures the wicking bar 420B into the wicking sub-frame 410B. The proximal and distal end of the wicking bar 420B then snaps into or attaches to the proximal and distal ends of the plastic end pieces 410B. Thereafter, the sub-frame 410B is attached to the frame 110 of the eyewear 100.

In one embodiment, the wicking sub-frame 410B includes a snap hook detail 411C, mechanism snaps, protrusion, or insert portion 411D which engages a mating cut-out or receiving portion 112 on the eyewear frame 110. In another embodiment, illustrated in FIG. 29D, a sub-frame 410K may be attached to the brow area of the frame 110 using a holding mechanism 460 as shown.

The wicking or brow bar 420 is a flexible bar made of plastic or spring steel which provides a platform for the wicking material 430 attached to the brow bar 420. In one embodiment, the wicking bar 420 is configured for receiving the wicking material which is shaped into a tubular sleeve. Preferably, the wicking bar 420 has a cylindrical or rounded shape for slipping or inserting the tubular wicking material 430. The surface of the wicking bar 420 is sufficiently smooth to allow the tubular wicking material 430 to pass over the length of the brow bar 420 without tearing or stacking up. The wicking bar 420 has a circular shape which follows along the inner outline of the frame 110 of the eyewear 100. The wicking bar 420 is releasably or permanently attached to the sub-frame 410 or directly to the frame 110 of the eyewear 100 itself. In one embodiment, the wicking bar 420 is snap fit into the sub-frame 410. In another embodiment, the shape of the wicking bar 420 may be L shaped, oval, or rectangular, or other shapes suitable for resting upon a user's brow area.

The wicking material 430 attached to the wicking bar 420 is used for removing or absorbing sweat or moisture from the brow or face of a user. It is contemplated that the wicking material 430 may have a tubular shape of mesh fabric or other types of stitching. Note, the wicking material may have a shape other than tubular for attachment to the wicking bar 420. The wicking material 430 may be permanently or removably attached to the wicking bar 420. The wicking material 430 may include a moisture absorbent fabric or other wicking material for removing moisture. Some examples of other wicking material may include Sorbtek® or other absorbent fabric or sponge material, such as a foam pad or foam material, for absorbing or removing moisture or perspiration for the face of a user.

The absorbent material or wicking material 430 may be attached and end-sealed by a variety of methods known in the art including the following: heat shrink, burning, welding, dipping, overmolding, melting, applying adhesive, overlaying, snapping into, and coating similar to a shoelace tip. The configuration of the wicking material 430 and the brow bar 420 may determine how the wicking material 430 and the brow bar 420 are attached and how the end-seal of the wicking material 430 is achieved. These are merely examples of possible methods for attaching the wicking material 430 to the brow bar 420 or the sub-frame 410. Most importantly, any method of attaching the wicking material 430 should prevent fraying of yarn ends and stack up of material.

In one embodiment, the wicking material 430 may be a combination of both a closed cell material and stitched fabric material. First, a foam material is die cut and attached to the brow bar 420 with low initial tack adhesive. Next, a wicking material 430 is slid over the brow bar 430 with attached foam to provide further pressure, conformance to head, and comfort to the user. It should be noted that the tubular wicking material 430 or sleeve may be subdivided into more than one piece to facilitate pulling over the wicking bar 420, sub-frame 410, or attachment to the frame 110 of the eyewear 100 directly.

Referring to FIGS. 26A-C, there are a number of other possible embodiments for the wicking device 400. As illustrated in FIG. 26A, an L shaped sub-frame 410C having a mesh wicking material 430 covering the sub-frame 410C is attached to the existing frame 110 of the eyewear 100. Of course, the wicking bar or a combination of the sub-frame and wicking bar may be substituted with the wicking sub-frame 420C. As illustrated FIG. 26B, a wicking sub-frame 410D made of a mixture of TPU 440B (thermoplastic polyurethane) and rigid or structural plastic 440A has a mesh wicking material 430D over the wicking sub-frame 410D which is attached to the existing frame 110 of the eyewear 100. Of course, the wicking bar or a combination of the sub-frame and wicking bar may be substituted for the wicking sub-frame 410D. As illustrated in FIG. 26C, a wicking sub-frame 410E includes a mixture of foam 450A and plastic material 450B with a mesh wicking material 430E over the wicking sub-frame which is attached to the existing frame 110 of the eyewear 100. Of course, the wicking bar or a combination of the sub-frame and wicking bar may be substituted for the wicking sub-frame 410E.

Referring to FIGS. 27-32D, the wicking device 400F includes the wicking bar 420F and absorbent or wicking material 430F without a sub-frame. The wicking bar 420F may contain a connection mechanism at its distal and proximal ends for being secured to the inside of the eyewear frame 110. In one embodiment, the wicking bar 420F has a hook at a proximal and distal end for snapping into a recess or aperture defined with the frame 110. Another method of attachment of the brow bar 420G directly to the inner frame 110 includes a snap mechanism 422G located on a middle portion of the wicking bar 420F which engages the aperture 412G located on the frame 110.

In another embodiment, the wicking device 400 includes a sub-frame 410 and absorbent material or wicking material 430 without a brow or wicking bar 420. The sub-frame 410 has a proximal and distal end which is removably attached to the brow area of the eyewear frame 110. In one embodiment, the sub-frame 410 defines an "L" shape and travels along an inner periphery of the brow bar area of the frame 110. The proximal and distal ends of the sub-frame 410 including raised protrusions which interfittingly engage recess areas defined with end pieces of the eyewear. It is contemplated that additional methods known in the art for joining the sub-frame and the eyewear may be done also such as adhesives, fasteners, etc.

The wicking material 430 is pulled over the sub-frame 410 and then the sub-frame 410 and the frame 110 of the eyewear are snapped or attached together. Referring to FIGS. 32A-D, in one embodiment, the sub-frame is a series of one or more pieces 410H (one piece), 410I (two pieces-A, B), 410J (three pieces—A, B, C) joined together by a variety of attachment mechanisms, such as illustrated in FIG. 32B. For example, the sub-frame 410J is divided into a main band and two end pieces for engagement to the frame 110 of the eyewear. The band of the sub-frame 410J snappingly engages the two end pieces for either permanent or releasable attachment. In this case, one of the end pieces may be integrally or permanently attached to the band, while the opposite end is detachable in order to allow the wicking material 430 to be easily slid over the band and sealed in place before securing it in its final assembled position. Of course, the sub-frame 410 and the wicking bar 420 may be divided into less than or greater than three pieces.

In one embodiment, the wicking material is mesh fabric stitched into a sleeve and pulled along the brow bar to cover it. In another embodiment, the sub-frame is interlocked with thermoplastic polyurethane and surrounded by the wicking material which is mesh fabric. In another embodiment, the sub-frame is attached to foam material and surrounded by the wicking material which is mesh fabric. To strengthen the connection, the sub-frame may also include a holding mechanism for securing the sub-frame to the brow area of the eyewear. In another embodiment, the sub-frame includes two or more pieces which are snapped together and each piece has wicking material situated over the sub-frame.

In one embodiment, the wicking sub-frame 410 is a single piece that includes an insert portion 414A, 414B at each end. Each insert portion 414A, 414B of the sub-frame 410 is engaged within a corresponding receiving portion defined within the end pieces of the eyewear frame. The sub-frame further includes receiving portions at each end to allow insert portions of the brow bar to be inserted therein. The brow bar matingly engages a contour of the subframe along a substantial portion of its length, the brow bar slightly raised above an upper surface of the sub-frame. To further secure the sub-frame to the eyewear, a central protrusion extends from the sub-frame near a central portion of the upper eyeframe area. The central protrusion engages a receiving aperture within the brow bar to secure the brow bar the sub-frame. It is also contemplated that the wicking material 430 may be attached directly to the frame of the eyewear without a brow bar of sub-frame to absorb or remove moisture or perspiration from a persons' face.

In operation, the wicking bar device 400 is removably or permanently attached to the frame 110 of the eyewear. While a user sweats, the perspiration is absorbed or removed by the wicking material 430 on the wicking bar device 400. After usage of the wicking bar 400, the wicking bar 400 may be replaced or cleaned by removing the wicking bar 400, or its individual components, and replacing or cleaning it. Also, the wicking material 430 may be removed from the brow bar 420, sub-frame 410, or the frame 110 of the eyewear for cleaning or replacing after usage. Overall, the wicking bar 400 may be removable, replaceable, washable, and have easy mounting and detachment for a user.

Figure 35:
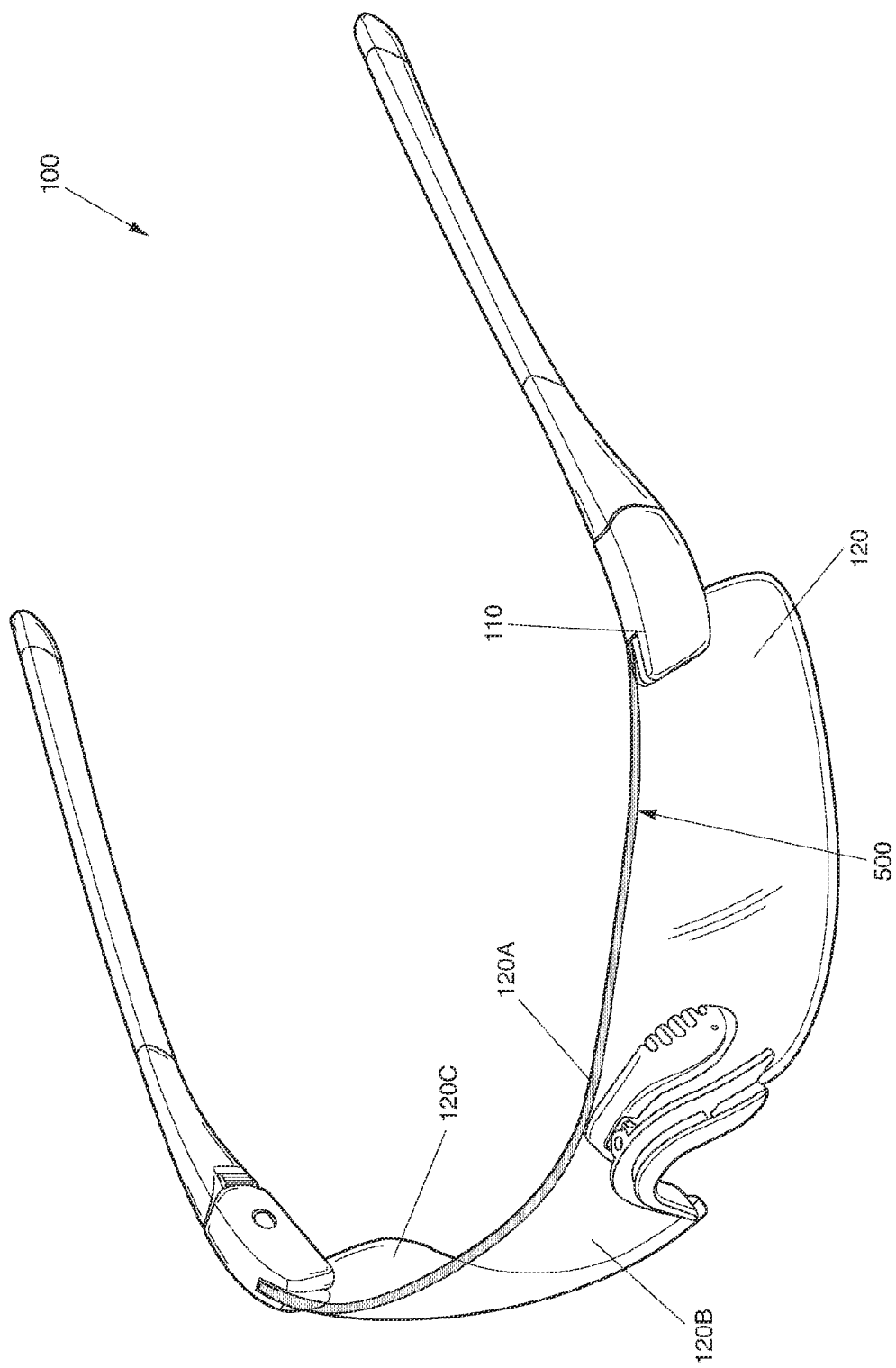
FIG. 35 is a perspective view of another embodiment of the colored tinting along the outer peripheral edge of the lens.

Referring to FIGS. 33-35, the safety eyewear 100 of the present invention includes a coloration or tinting 500 of an outer peripheral edge 120A of the lens 120 for indicating a performance characteristic of the safety eyewear 100 or the lens 120 and/or selected absorption of visible wavelengths of light. The VLT (Visible Light Transmission) rated lens 120 has a light dye or tint 500 to provide ornamental color and/or selected absorption of visible wavelengths of light. The VLT is the percentage of available light allowed to reach the eye. In a preferred embodiment, the VLT rating is not less than 85%, such VLT allowing the transmission of ample light for use in most indoor settings A range of 74% to 90% or higher than 90% may also be used in the present invention. The lens 120 having a roughened or textured cut along an outer peripheral edge 120A to facilitate diffraction of light and bring out the tint of the lens 120. Other than the outer peripheral textured edge 120A, the tint is not clearly shown, or instantly perceivable in the lens 120. The lens 120 having a light visible tint 500, or mist, along said roughened or textured cut edge to provide ornamental coloration of the outer peripheral edge 120A. The outer peripheral edge 120A of the lens 120 may be color coded according to a coating provided on the lens 120, indicating the function of the coating. Most importantly, a user can see the color 500 of the outer peripheral edge 120A of the lens 120 while still meeting industry VLT requirements for a substantially clear lens. By having the color or mist tint 500 occur on the outer peripheral edge 120A, it provides the user with the entire front and back surface area of the lens 120 for viewing without interference from coloration.

Figure 36:
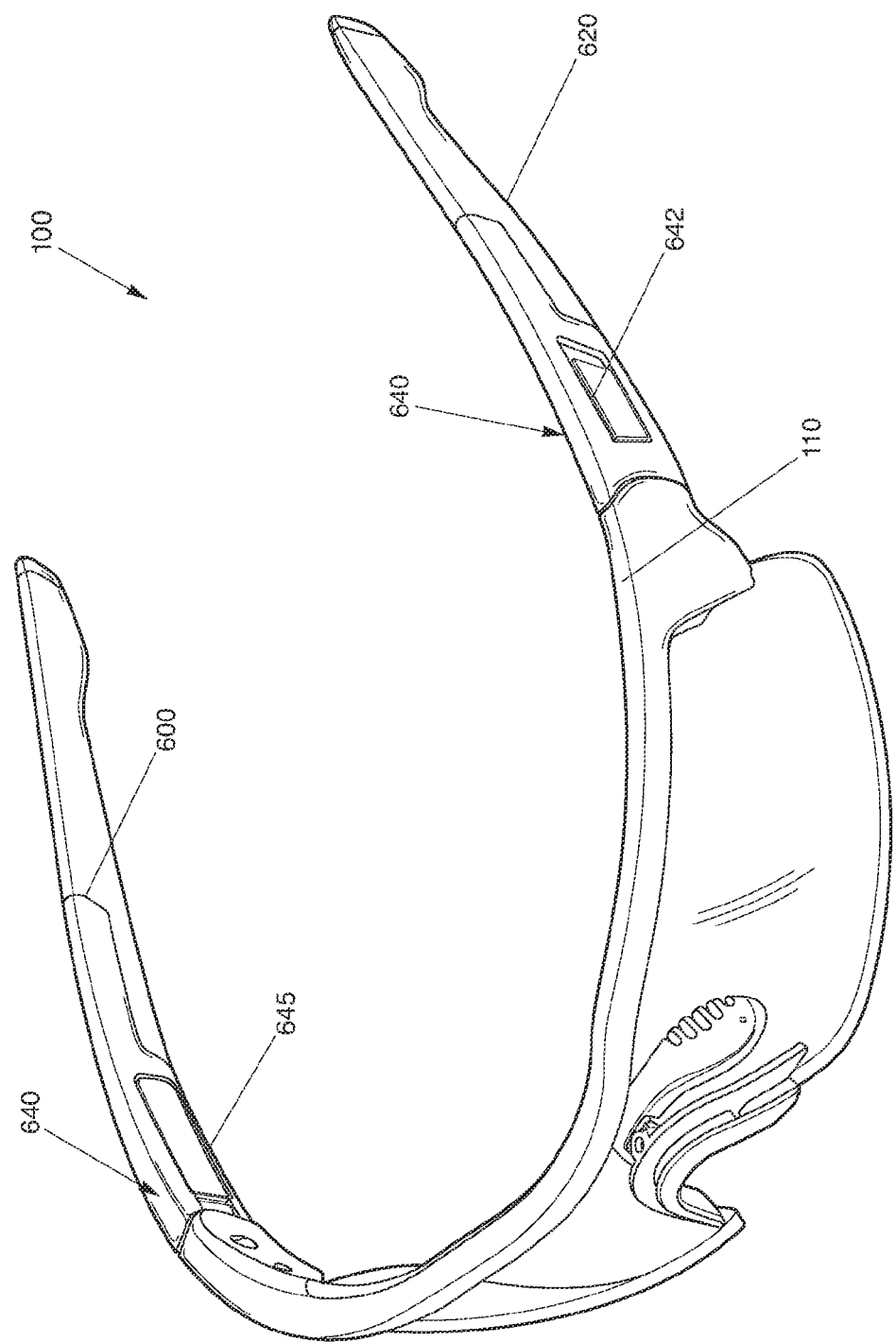
FIG. 36 is a perspective view of the safety eyewear of the present invention having temples with width adjustment.
Figure 37:
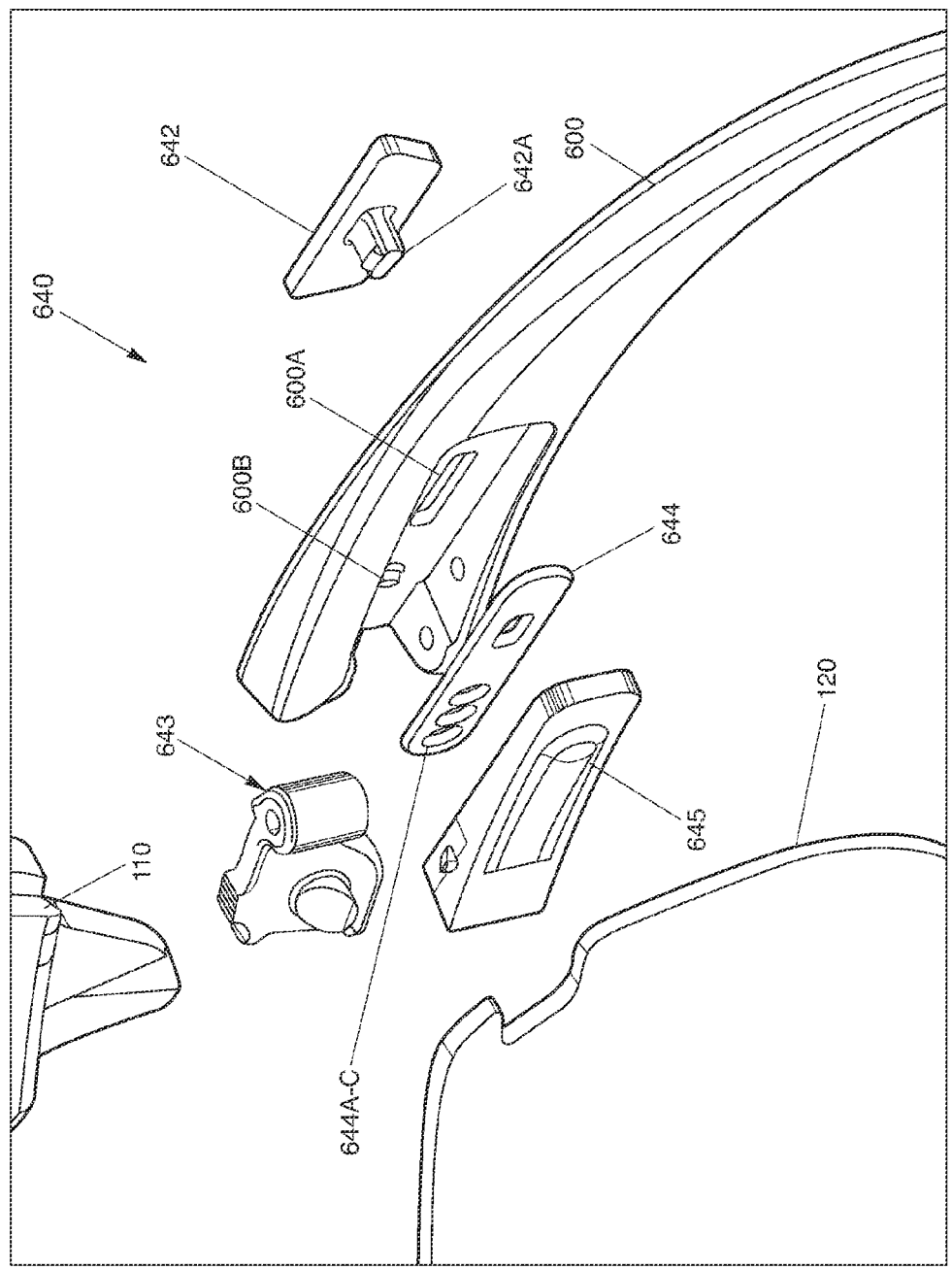
FIG. 37 is an exploded view of the hinge assembly providing the adjustment of the temple width.
Figure 38:
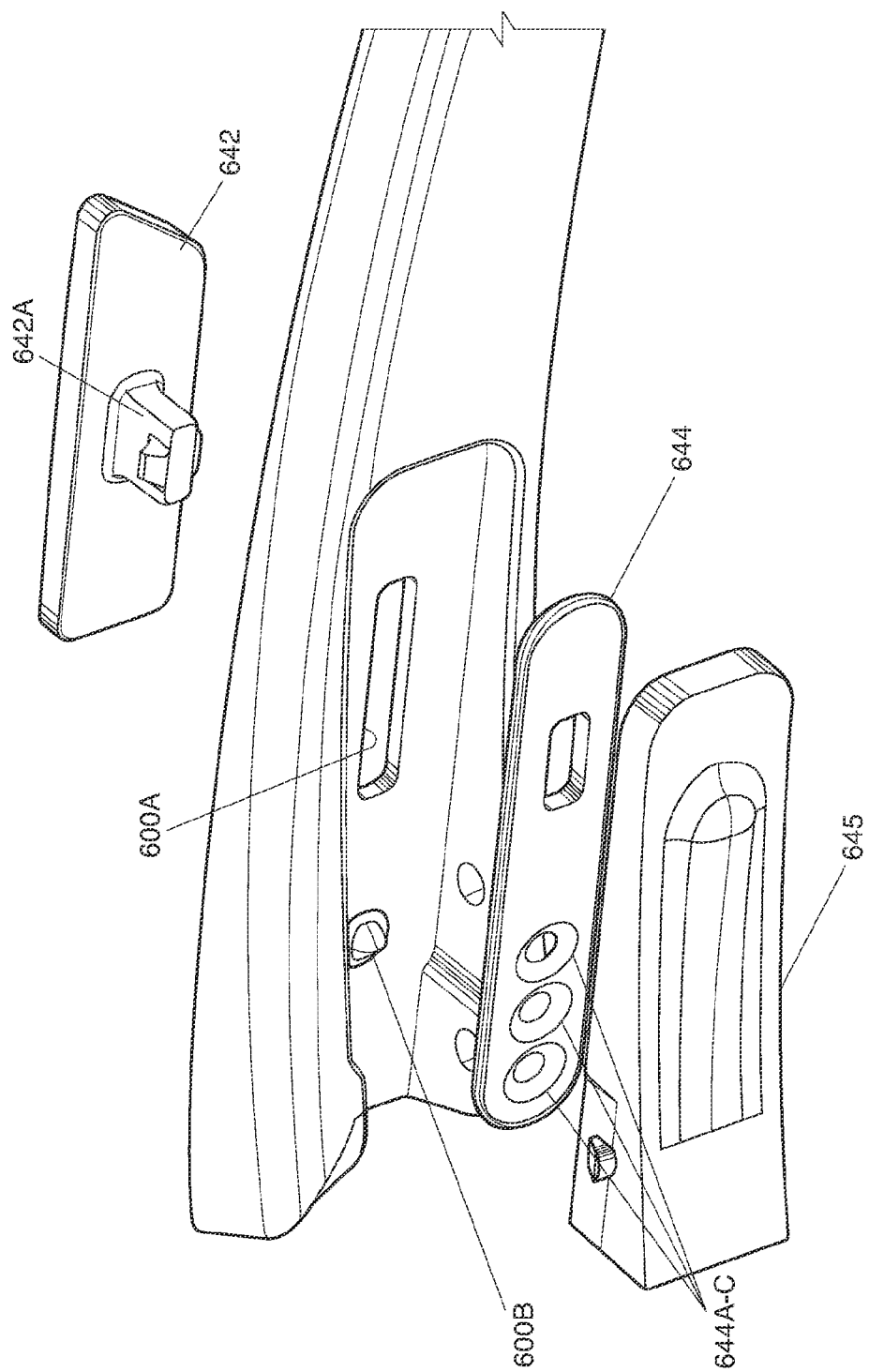
FIG. 38 is an exploded view of the hinge assembly providing the adjustment of the temple width.
Figure 39A:
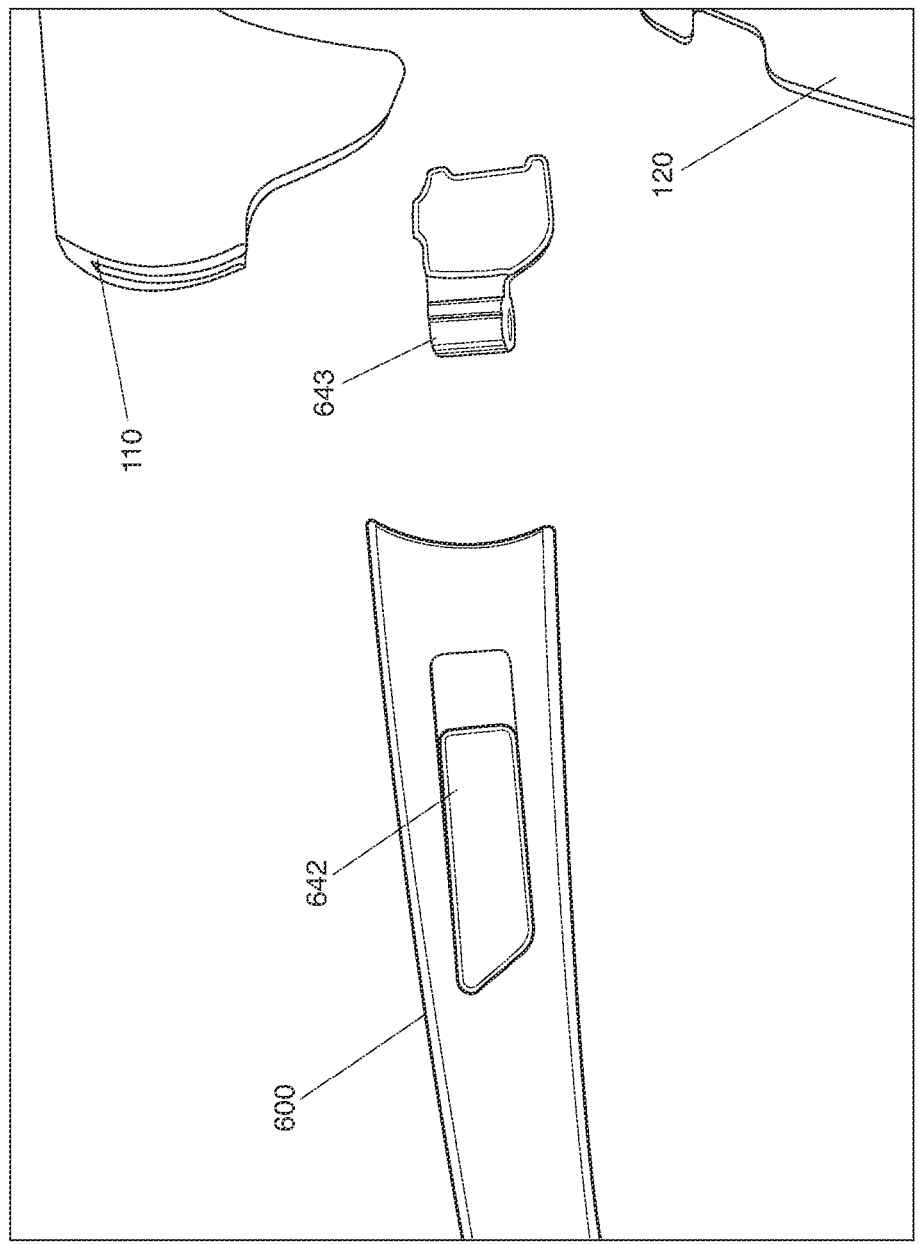
FIG. 39A is a side view of the temple bar of the present invention with the adjustment badge in the rearward position.
Figure 39B:
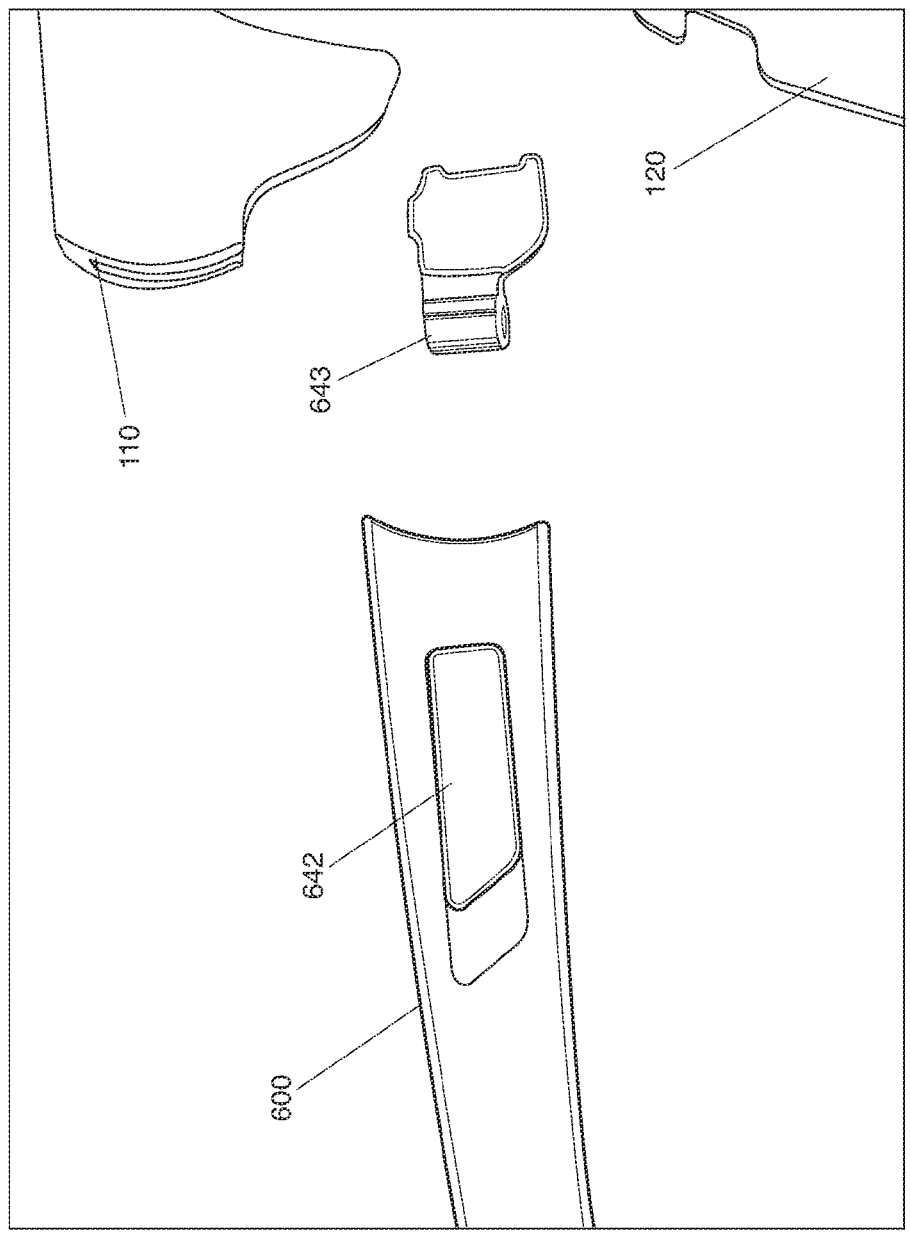
FIG. 39B is a side view of the temple bar of the present invention with the adjustment badge in the forward position.
Figure 43:
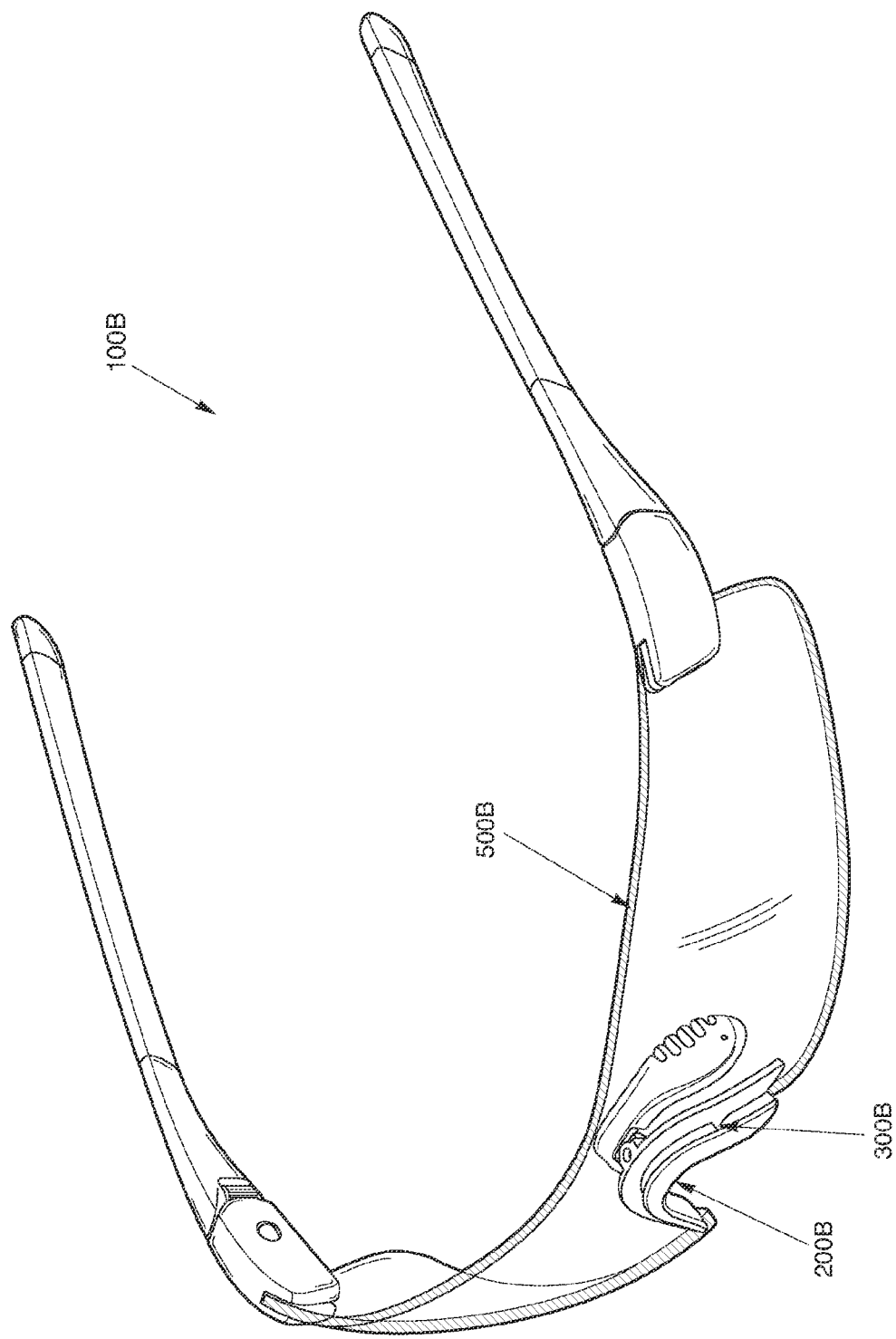
FIG. 43 is a front perspective view of an another embodiment of the safety eyewear.
Figure 44:
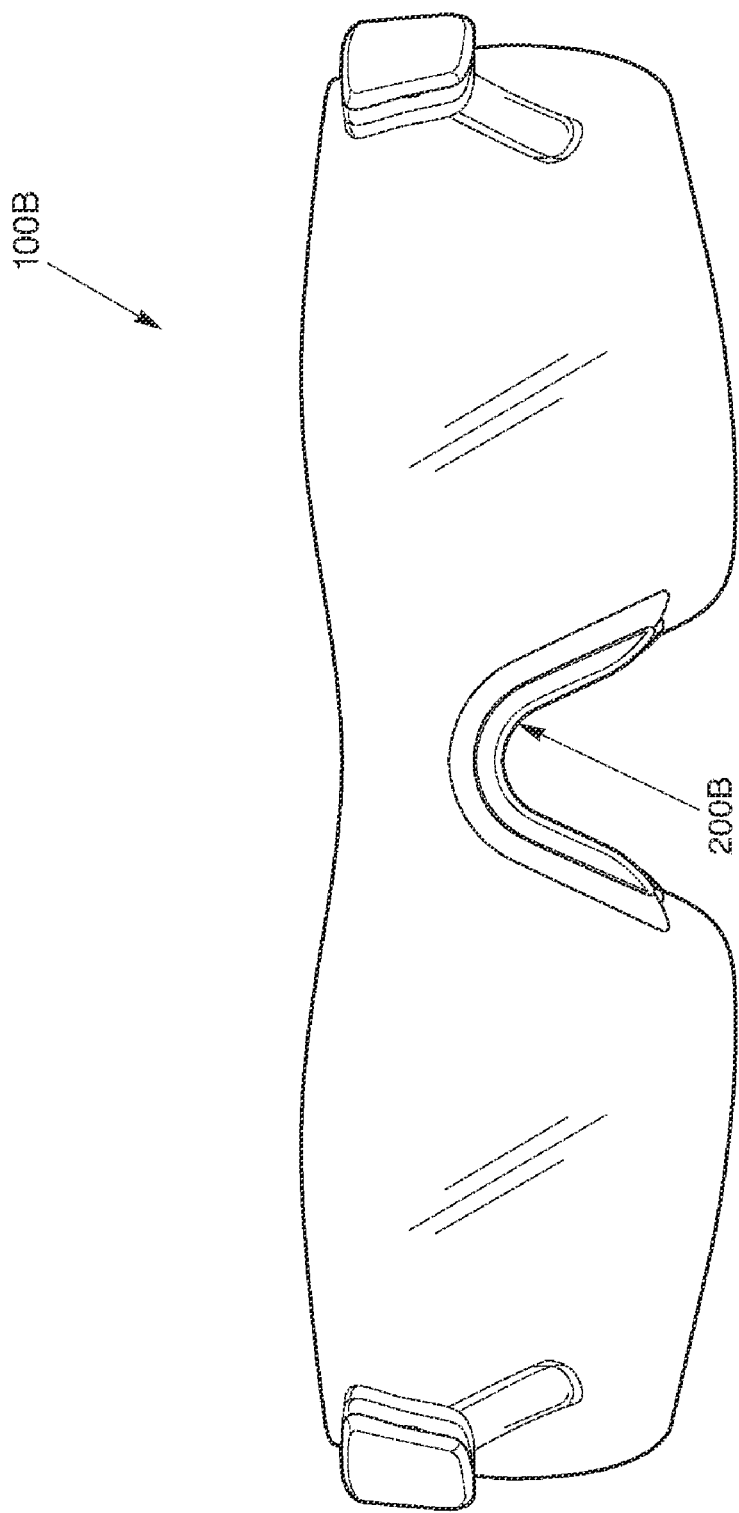
FIG. 44 is a front view thereof.
Figure 45:
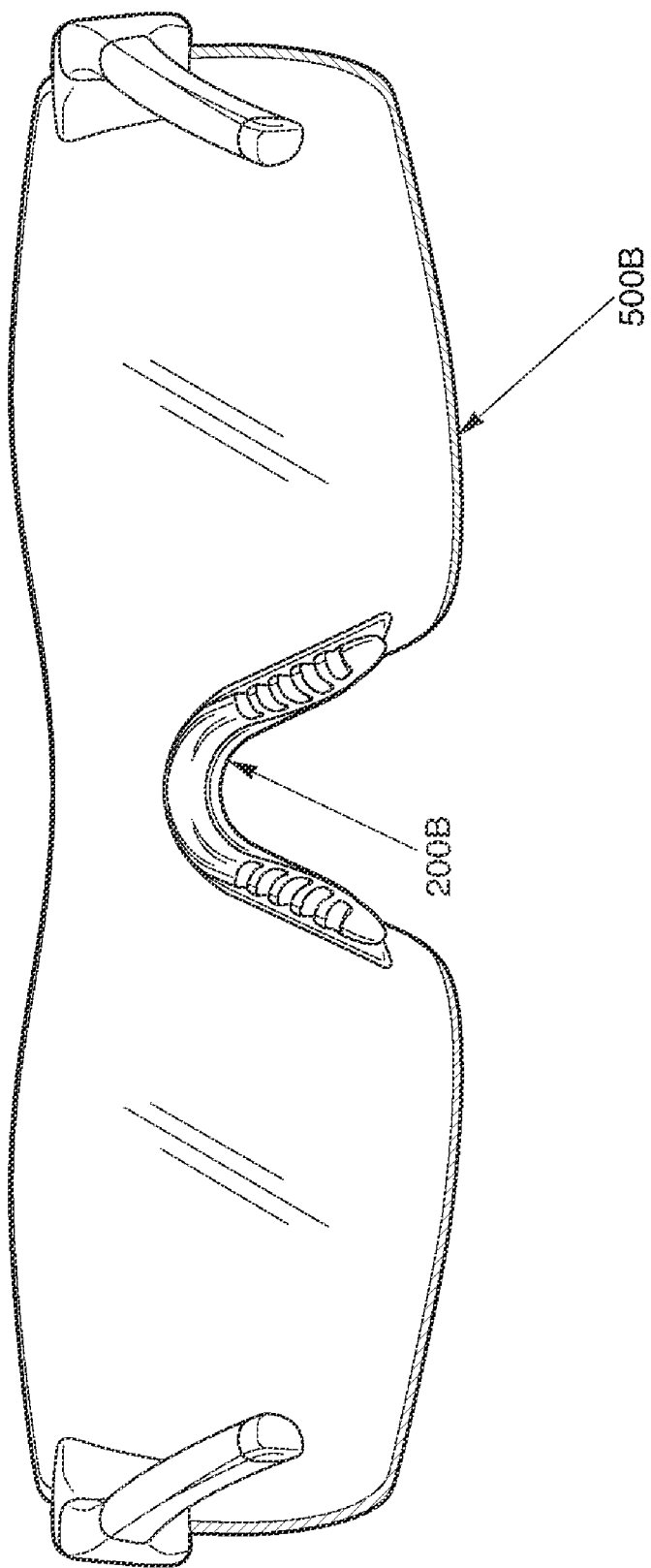
FIG. 45 is a rear view thereof.
Figure 46:
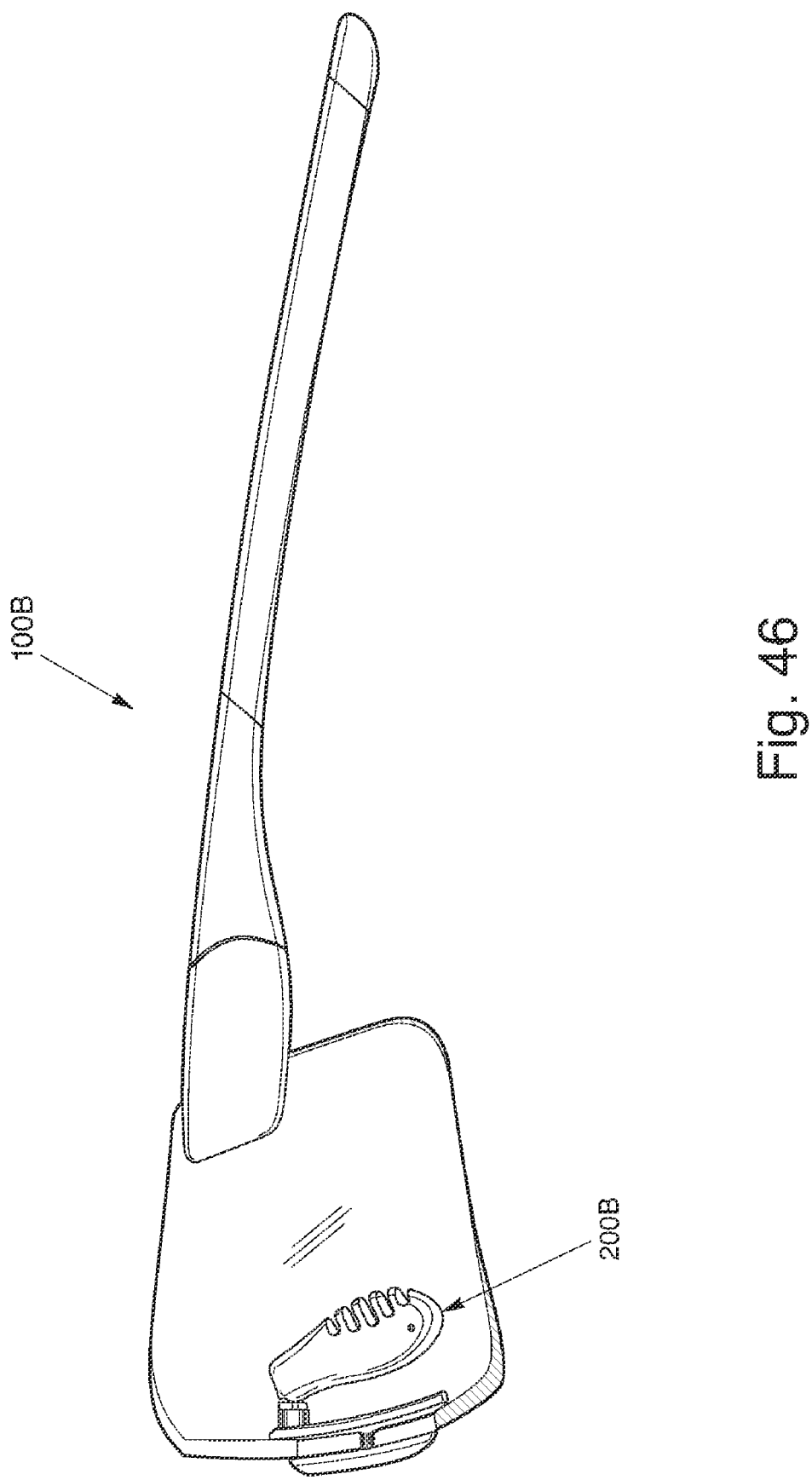
FIG. 46 is a fight view thereof.
Figure 47:
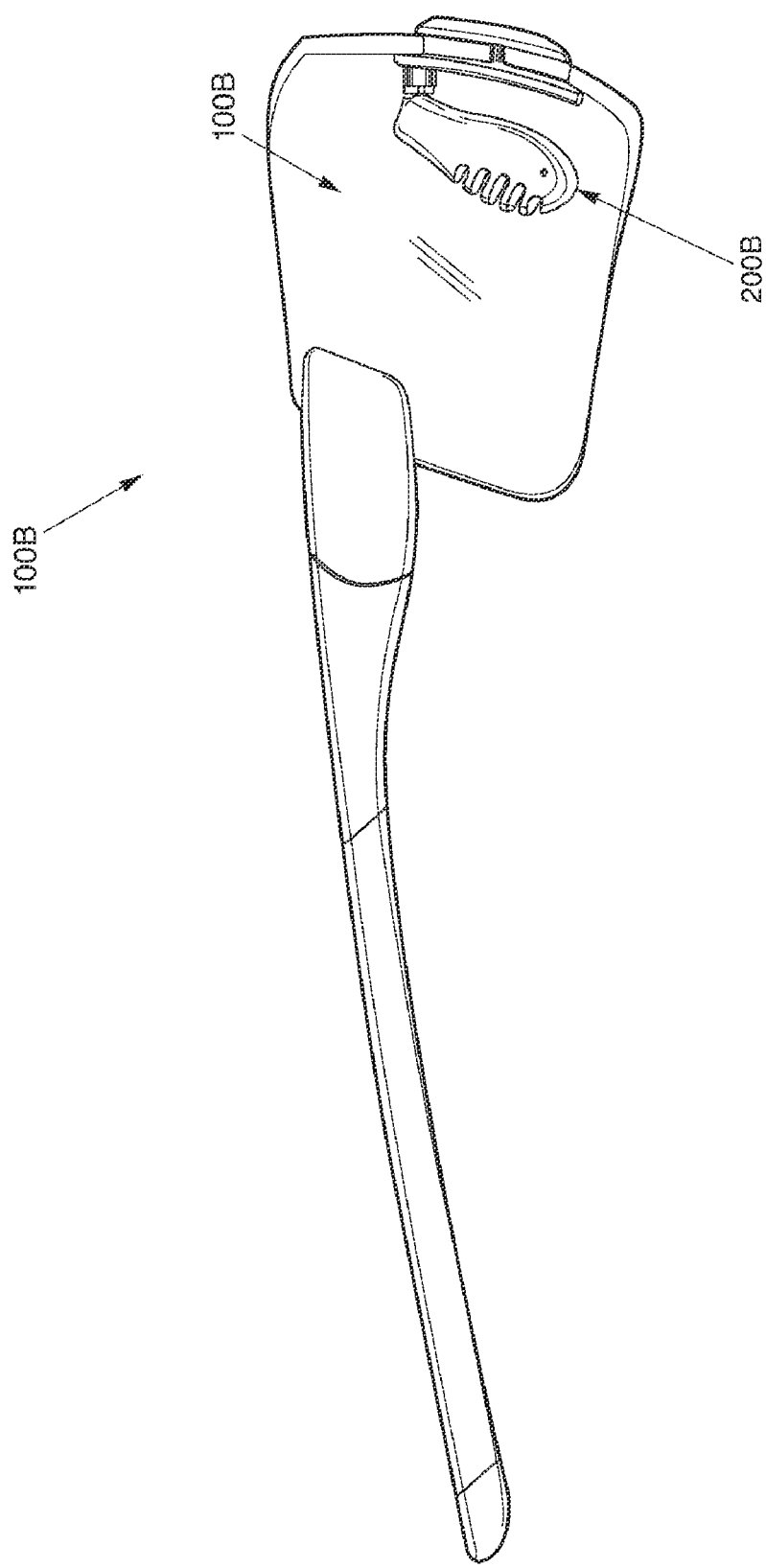
FIG. 47 is a left view thereof.
Figure 48:
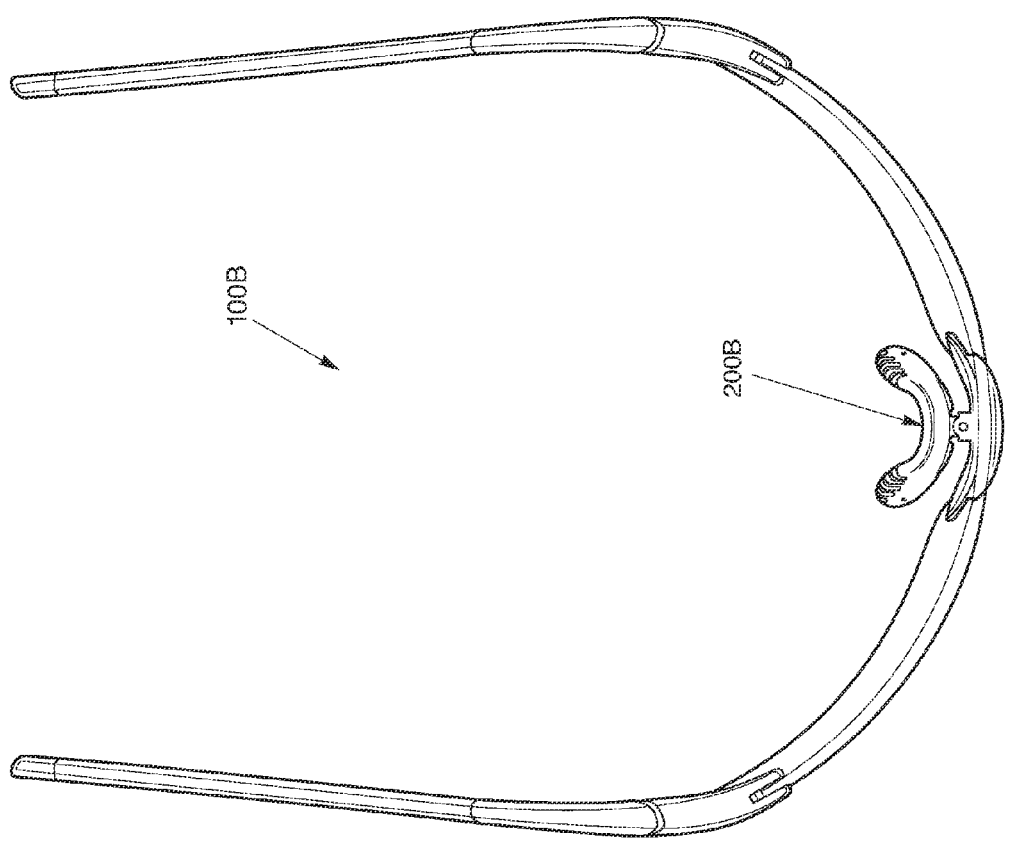
FIG. 48 is a top view thereof.
Figure 49:
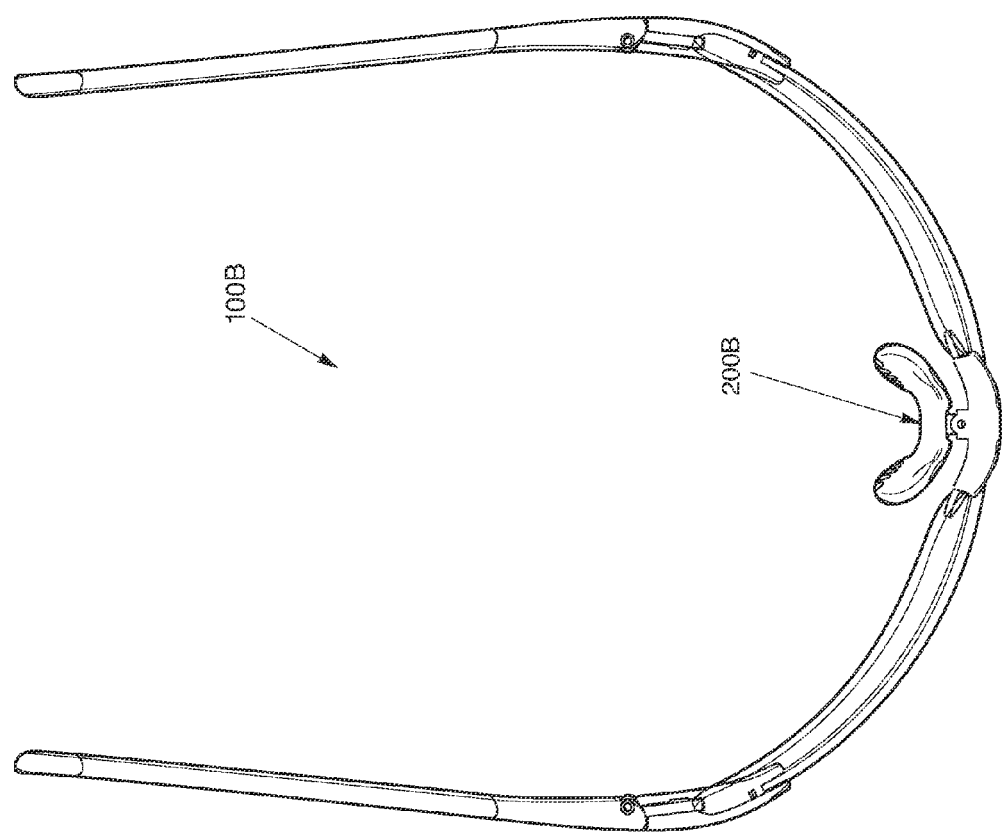
FIG. 49 is a bottom view thereof.
Figure 50:
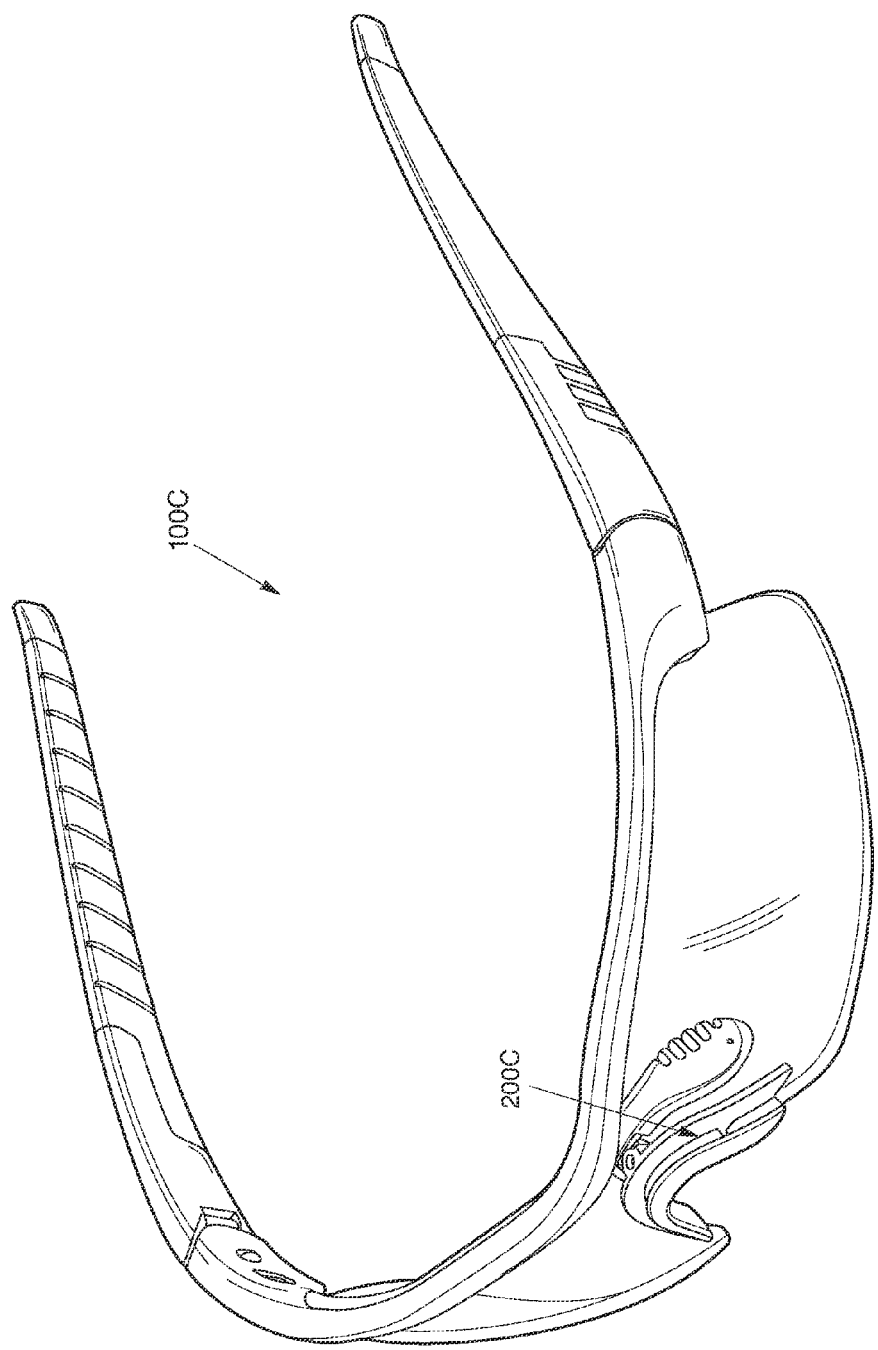
FIG. 50 is a from perspective view of another embodiment of the safety eyewear.
Figure 51:
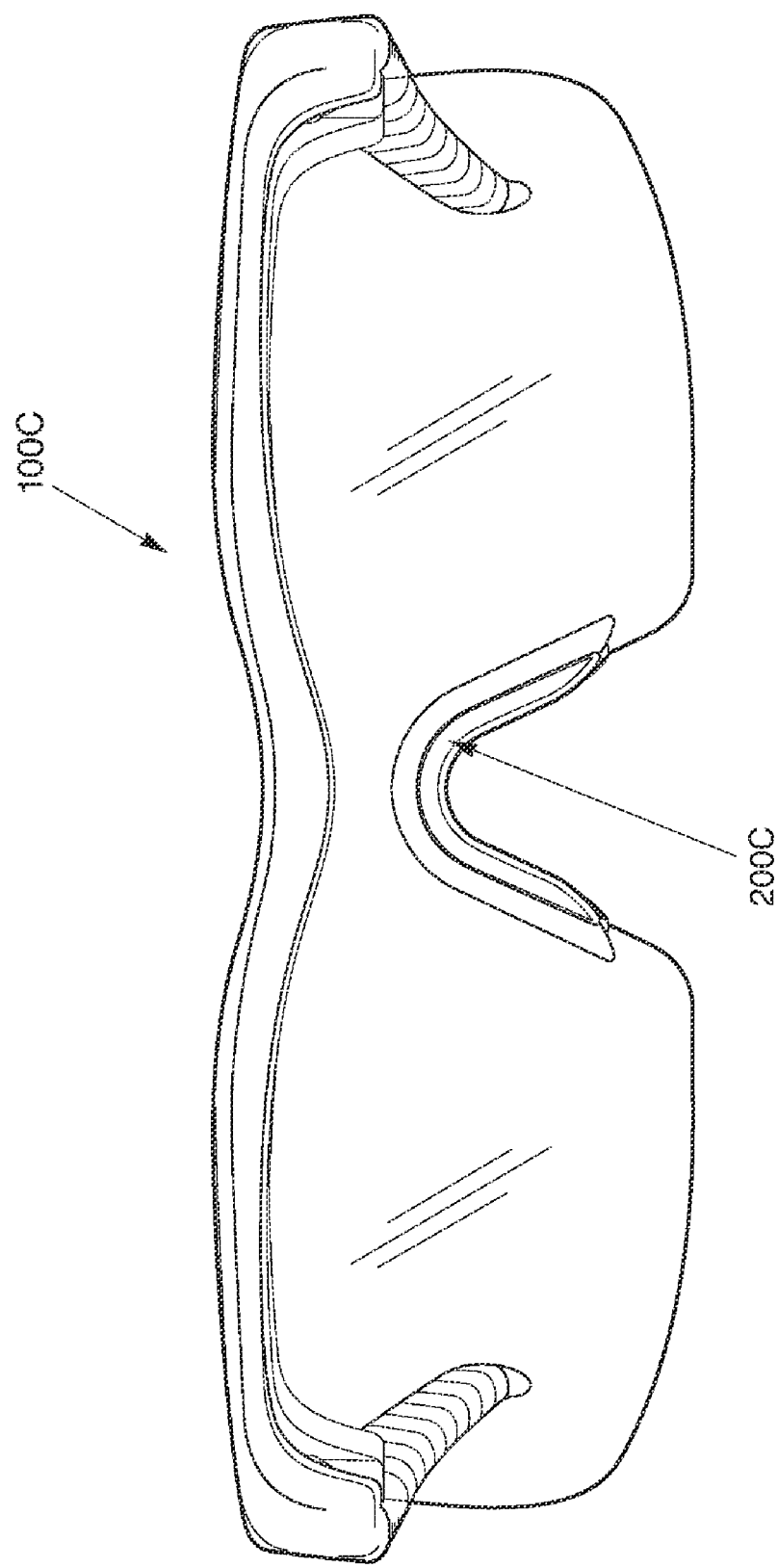
FIG. 51 is a front view thereof.
Figure 52:
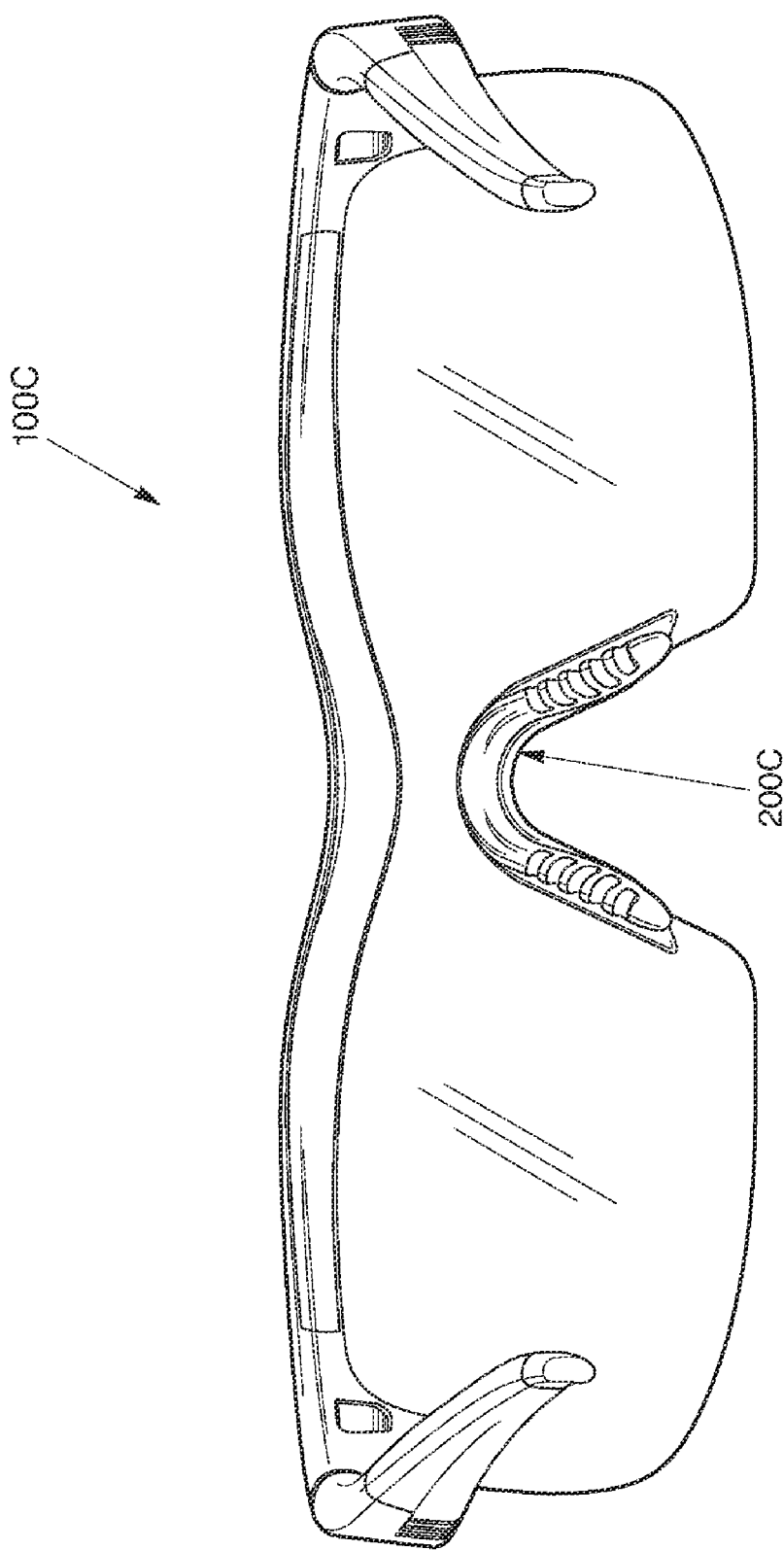
FIG. 52 is a rear view thereof.
Figure 53:
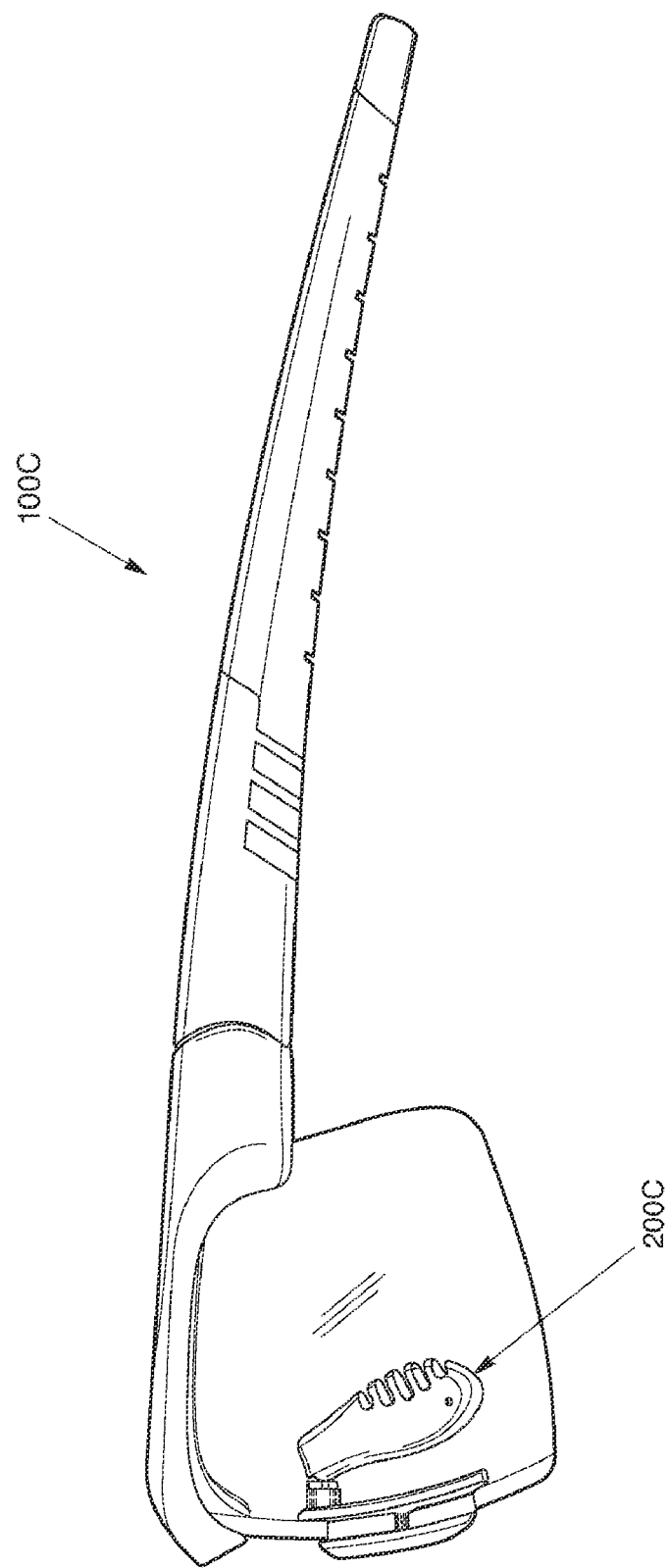
FIG. 53 is a fight view thereof.
Figure 54:
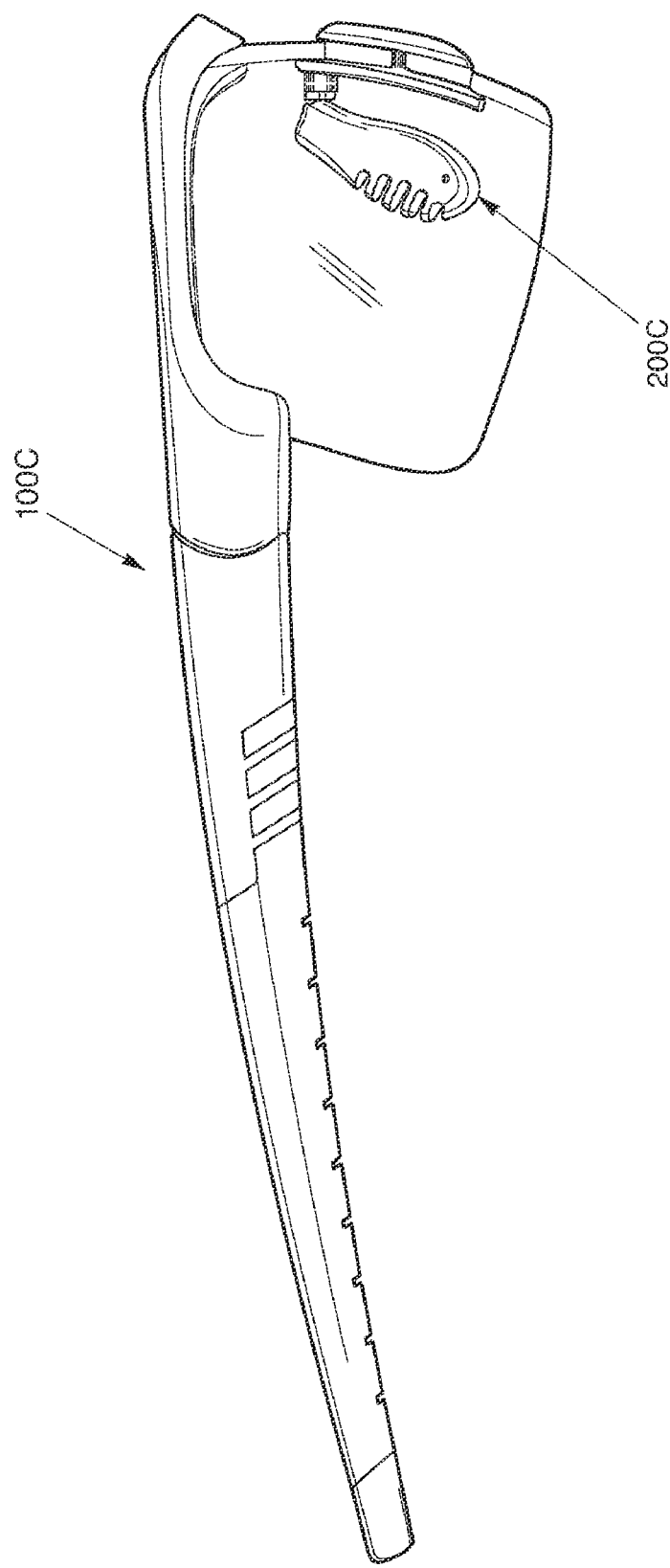
FIG. 54 is a left view thereof.
Figure 55:
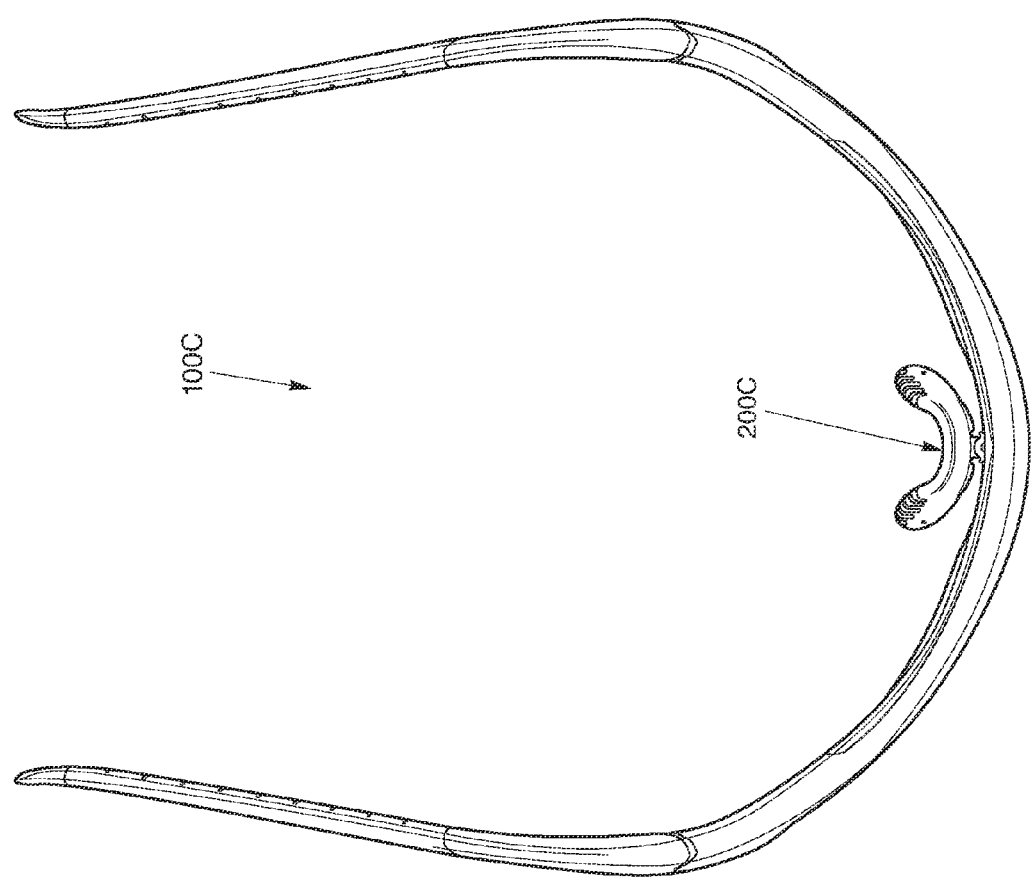
FIG. 55 is a top view thereof.
Figure 56:
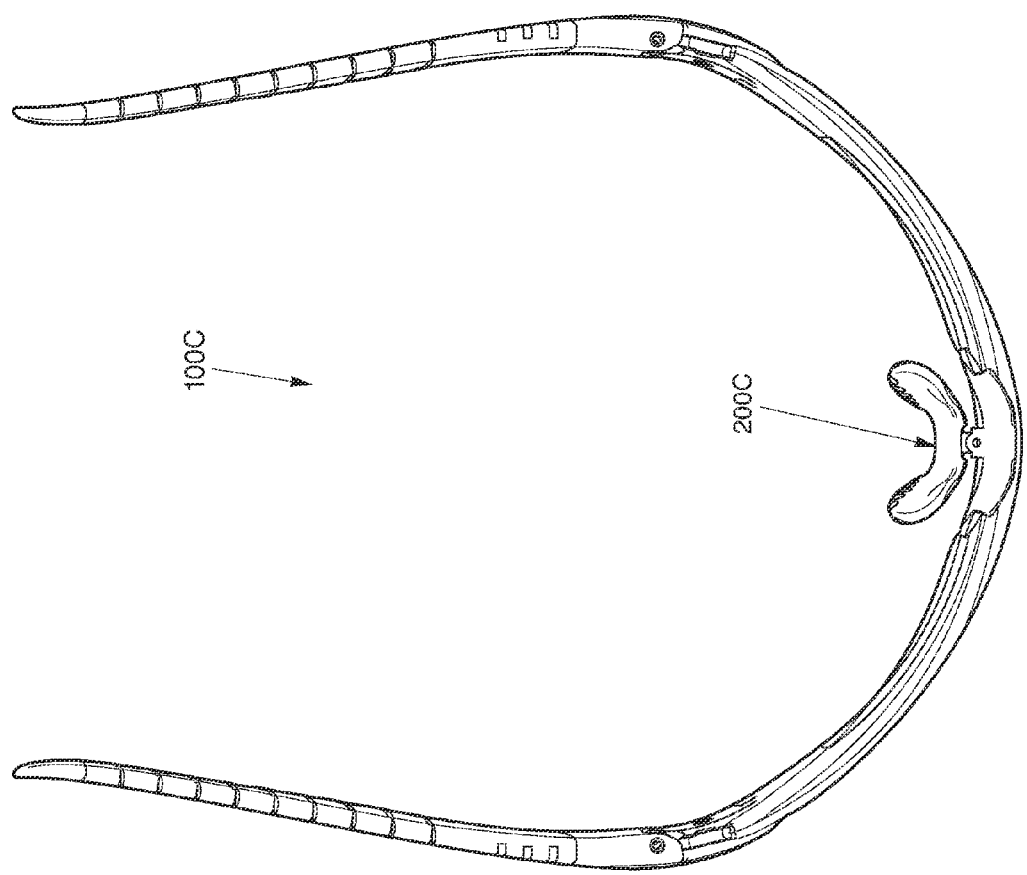
FIG. 56 is a bottom view thereof.
Figure 57:
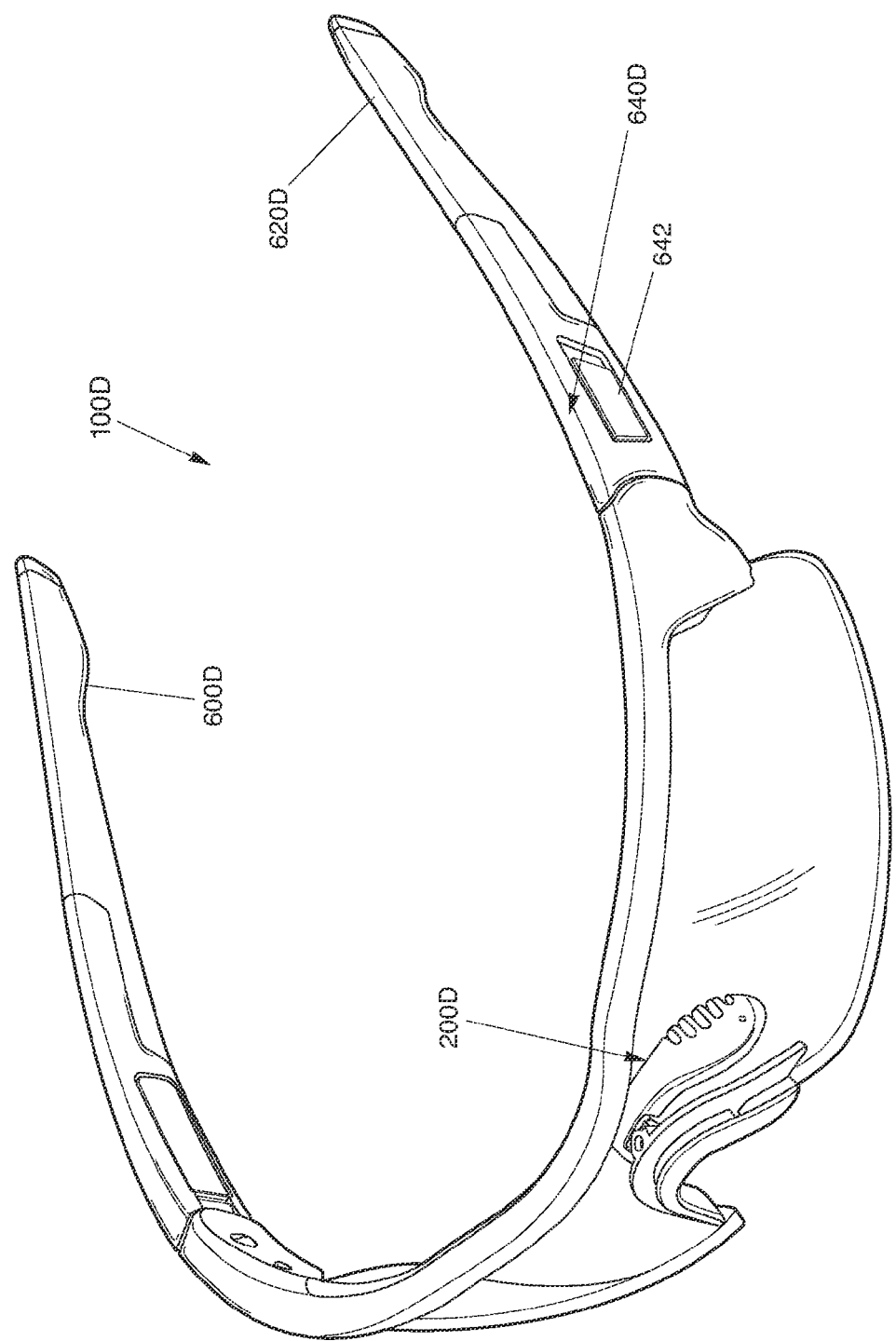
FIG. 57 is a front perspective view of another embodiment of the safety eyewear.
Figure 58:
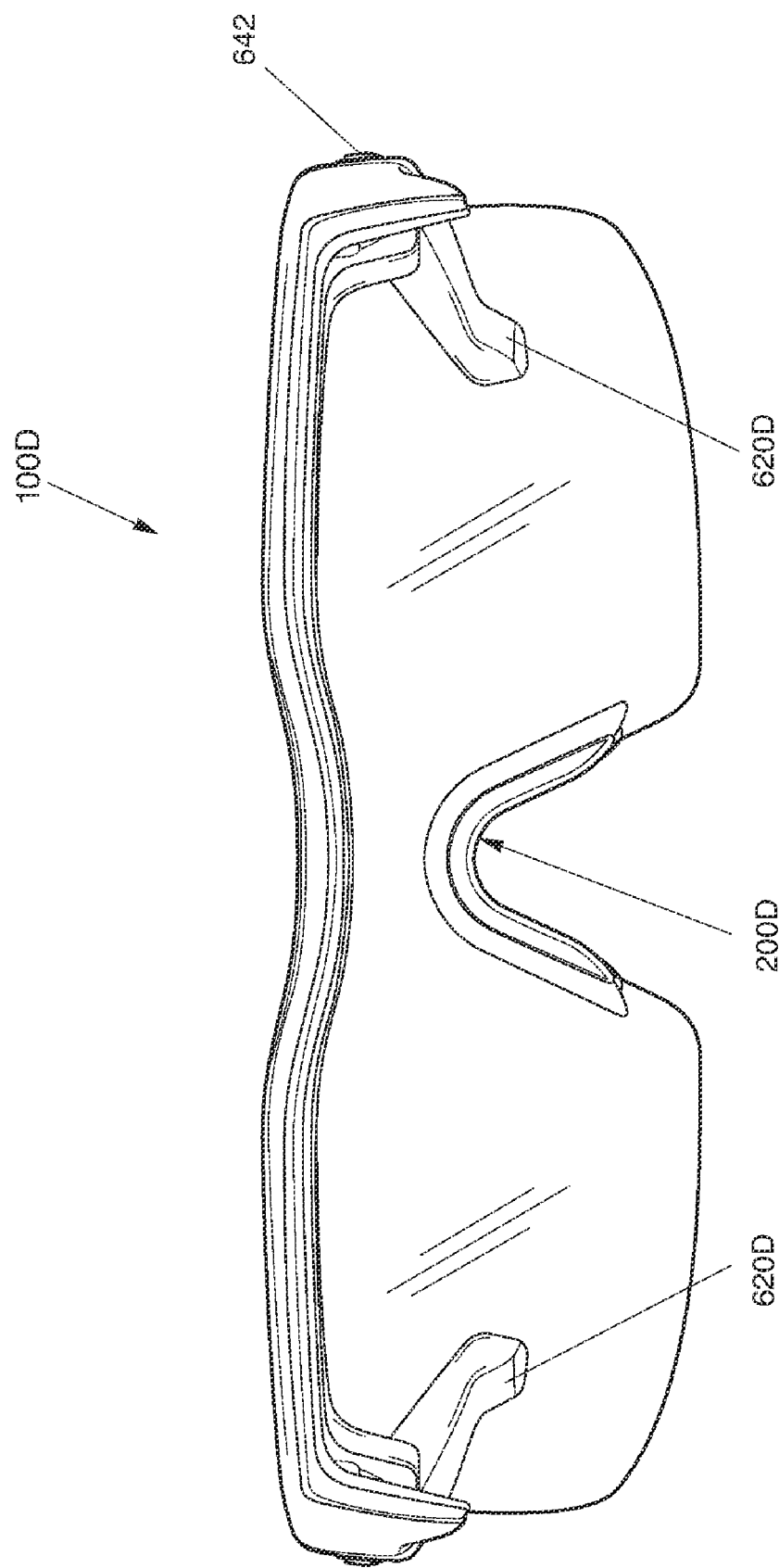
FIG. 58 is a front view thereof.
Figure 59:
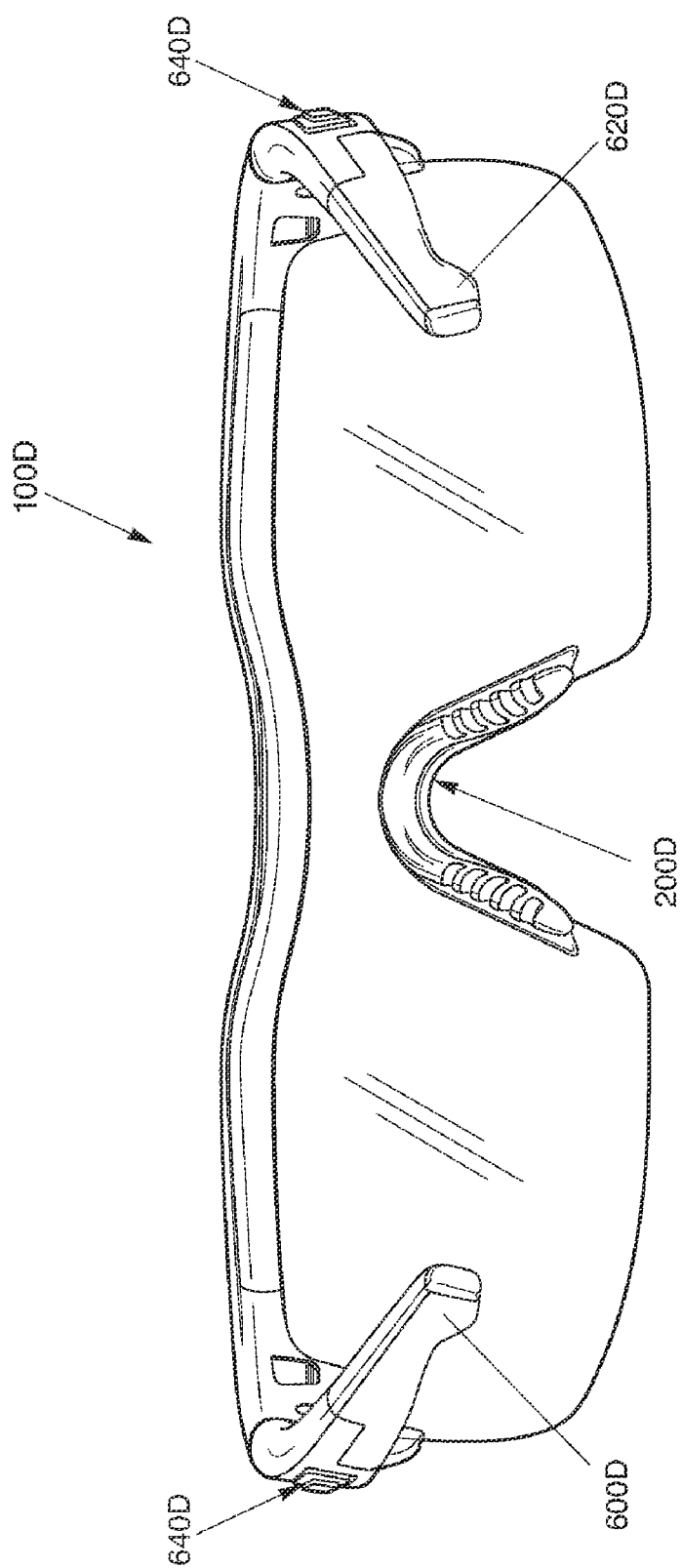
FIG. 59 is a rear view thereof.
Figure 60:
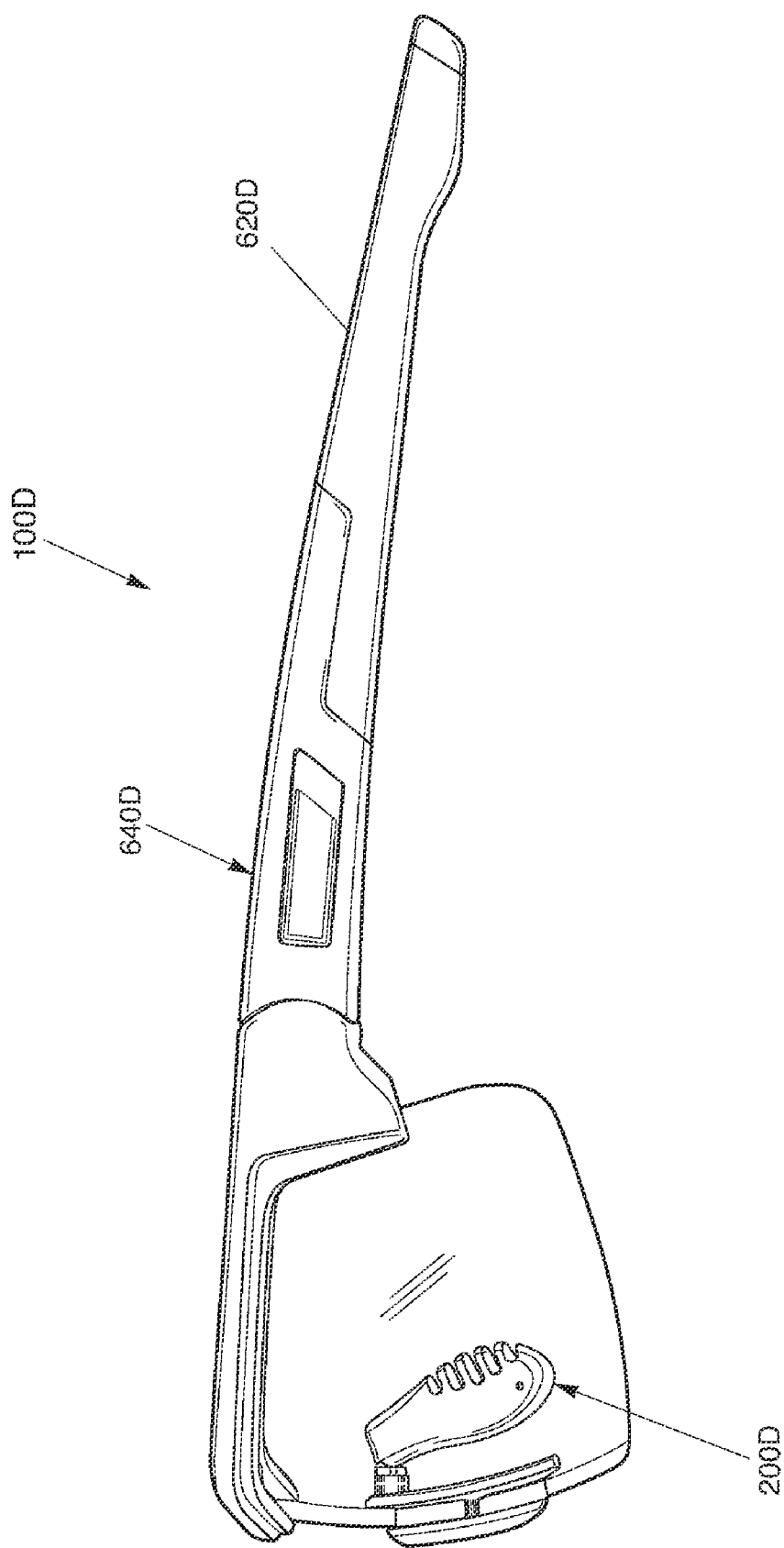
FIG. 60 is a right view thereof.
Figure 61:
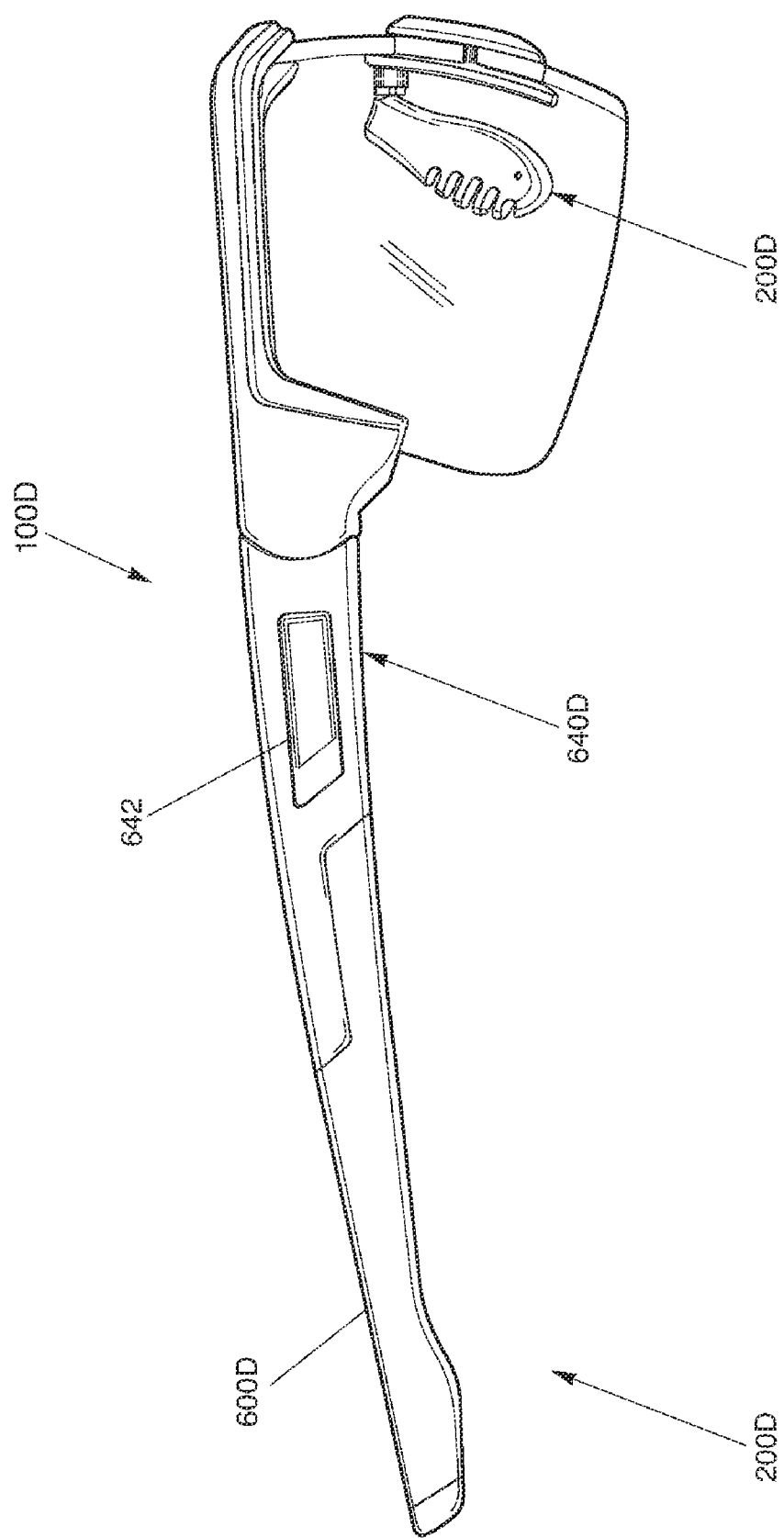
FIG. 61 is a left view thereof.
Figure 62:
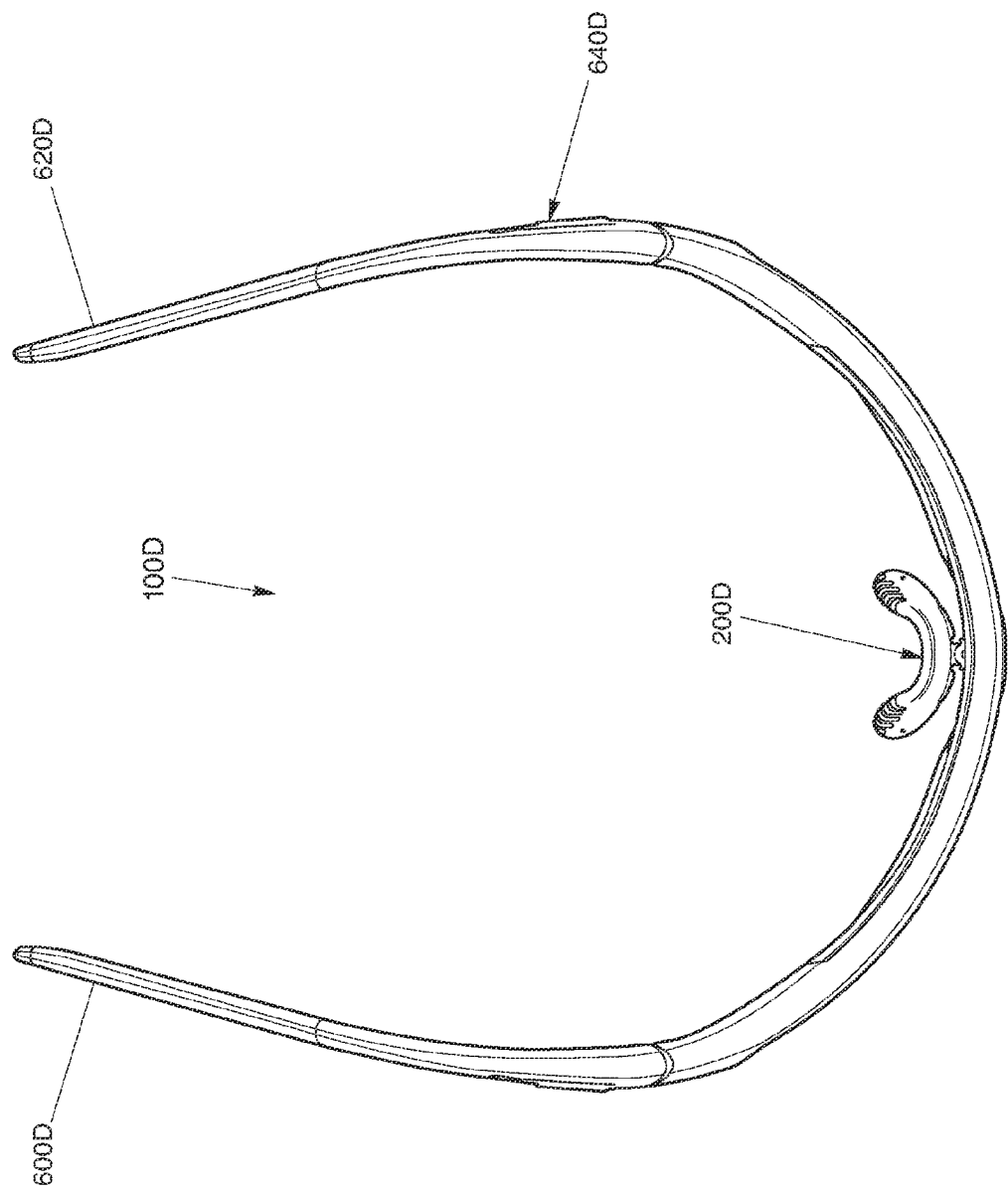
FIG. 62 is a top view thereof.

For example, a blue mist tint 500 may be provided which is shown when light diffracts along the outer peripheral edge 120A having the textured surface. The blue mist tint, in one embodiment, may indicate the general purpose, a characteristic of the lens (i.e. coating), quality, or a specific targeted purpose of the eyewear 100. A blue mist tint 500 may indicate a particular type of coating on the lens 120, such as anti-fogging, anti-glare, hard coating, or nuisance reduction. Of course, many tint colors may be used other than blue to indicate the performance characteristics or other features of a particular lens or eyewear. For example, FIGS. 35 and 36 show the possibility of different color orientations depending upon the tint 500 and textured cut along the outer peripheral edge 120A of the lens 120. Of course, it is possible that the textured cut along the outer peripheral edge 120A may extend the entire surface of the outer peripheral edge 120A or less than the entire surface of the outer peripheral edge 120A.

It is further contemplated that there may be more than one color used for a series of eyewear 100 depending upon the environment in which the lens or eyewear is being used. For example, a lens may display a tint color 500 of red along the outer peripheral edge 120A of the lens 120 if the eyewear 100 is not suitable for the particular environment. Conversely, a lens 120 may display a tint color 500 of green along the outer peripheral edge 120A if the lens or the eyewear 100 is suitable for the particular environment based on prevailing lighting conditions.

Another benefit of the color coding 500 of the outer peripheral edge 120A of the lens 120 is color therapy and color filtration. Color therapy is known to affect a person's mood or demeanor depending upon the desired affect by using color. By using different color coded lenses, the colors used may actually affect the work or job performance of the user. Color filtration, in special lighting conditions, is also a known effect of tinting the lens. By selecting the proper tint and lens material, certain wavelengths of light may be filtered in order to attenuate certain wavelengths for task specific situations even in indoor settings where overall VLT should be maximized.

In one embodiment, the eyewear 100 includes a frame 110 and a lens 120 having a mist or slight tint embedded or integrated within the material of the lens 120 during the manufacturing process of the lens. The lens 120 has a front surface 120B and a back surface 120C. In one embodiment, the entire front surface and back surface of the lens 120 has a VLT rating greater than or equal to 85%. The lens 120 includes a mist tint or slight tint in the lens material to provide ornamental color and selected absorption of visible wavelengths of light along the outer peripheral edge 120A of the lens 120. The outer peripheral edge 120A of the lens 120 has a roughened or textured cut edge to diffract light. In one embodiment, the outer peripheral edge 120A of the lens 120 has a VLT rating greater than 50%. The lens 120 has the slight or mist tint 500 along said roughly cut outer peripheral edge 120A to provide ornamental coloration of the lens edge. The lens edge color coded according to a performance characteristic of the lens 120 or the eyewear 100. In operation, the ornamental color of the lens is activated upon the diffraction of light along the outer peripheral edge 120A of the lens 120 while still meeting industry VLT requirements for a substantially clear front and back surface of the lens 120.

Now referring to the FIGS. 36-42, an embodiment of the safety eyewear 100 of the instant invention having temple bars 600, 620 with adjustable width is illustrated and generally indicated. As will hereinafter be more fully described, the eyewear 100 includes a frame 110 and temple bars 600, 620 hingedly connected to the frame 110 using a novel and unique hinge assembly 640 for adjusting the width of the temple bars 600, 620. The hinge assembly 640 provides for a ratcheting adjustment for the inward angle of the temple bars 600, 620 in the folded out position. By providing for ratchet adjustment of the width of the temple bars 600, 620, the temple bars 600, 620 can properly be fitted to securely and comfortably accommodate a head of a user.

Turning now to FIGS. 36-42, one of the unique features of the safety eyewear 100 of the present invention is the ability of the temple bars 600, 620 to be ratchedly adjusted for various widths. To allow for ratcheting adjustment, the hinge assembly 640 hingedly or pivotally connects the temple bar 600, 620 to the frame 110. The hinge assembly 640 includes a hinge barrel 643, an adjustment badge 642, and a setting interlock 644. In a preferred embodiment, the hinge assembly 640 is hingedly connected to a side edge of the frame 110. However, it is contemplated that the hinge assembly 640 can be hingedly connected to any part of the frame 110 suitable for allowing for ratcheting adjustment of at least one temple bar 600, 620.

The hinge barrel 643 is hingedly connected to a proximal end of the at least one temple bar 600. The hinge barrel 643 is received within a pivot area defined within an inner surface of the proximal end of the temple bar 600, 602. The hinge barrel 643 is integrally formed with a frame connection portion which is configured to attach to the frame 110. Once the hinge barrel 643 is fixedly attached to the frame 110, preferably a side edge of the frame 110, the temple bar 600, 602 will pivot about the hinge barrel 643 to provide inward movement of the temple bar 600, 620. The hinge barrel 643 also defines a stop for preventing outward movement of the temple bar 600, 620 beyond a certain angle relative to the frame 110.

An adjustment badge 642, shown with a logo, defines a generally rectangular shape and includes an inward flange 642A configured for positioning within an adjustment badge area defined within an outer surface of the proximal end of the temple bar 600, 620. The inner surface of the temple bar 600, 620 defines an aperture 600A to accommodate the slidable movement of the inward flange 642A forward and rearward. The inward flange 642A is also configured for attachment to the setting interlock 644 positioned on the inner surface area of the proximal end of the temple bar 600, 620. The inward flange 64A, in one embodiment, has opposed raised areas on its outer end to facilitate a snap-fit with the distal end of the setting interlock 644. The setting interlock 644 is configured to move forward or rearward in correlation with movement of the adjustment badge 642 by a user.

The proximal end of the setting interlock 644 defines a series of snap adjustment apertures 644A-C for a snap-fit with a snap protrusion 600B defined within the inner surface of the temple bar 600, 620. Each snap adjustment aperture 644 A-C defines at least one setting of range of inward pivotal movement of the temple bar 600, 620 about the hinge barrel 643. Each setting or position of the setting interlock 644 provides an inward angular adjustment of the temple bar approximately 5.5 degrees. Of course, the setting interlock 644 may be configured for a different angular adjustment per snap-fit with a snap protrusion by more than or less than 5.5 degrees. In a preferred embodiment, there are three snap adjustment apertures for three different settings or positions, but it should be understood that more than or less then three different settings may be used. By ratcheting the snap adjustment apertures 644A-C over the snap protrusion 600B at different settings, the distal end of the setting interlock 644 moves between the hinge barrel 643 and the inner surface of the temple bar 600, 620 which increases or decreases the range of inward movement of the temple bar 600, 620 about the hinge barrel 643.

The invention utilizes multi-shot molding techniques. In one embodiment, the temple bar 600, 620 is made by a dual shot with a wire core insert for hingedly connected to a side edge of the frame. Also, a back cover 645 may be attached to the inner surface of the temple bar 600, 620 to retain and protect the hinge assembly 640.

In operation, when the adjustment badge 642 moves forward, it decreases the range of inward pivotal movement of the at least one temple bar 600, 620. When the adjustment badge moves forward, it moves the setting interlock 644 forward, which in turn ratchets the snap adjustment apertures 644A-C over the snap protrusion 600B forward. The setting interlock 644, by moving forward, further positions itself between the hinge barrel 643 and the inner surface of the temple bar 600, 620 to reduce or decrease the range of inward pivotal movement of the temple bar 600, 620. For example, for a small head adjustment, the adjustment badge 642 moves forward to decrease the range of inward pivotal movement of the at least one temple bar 600, 620.

When the adjustment badge 642 moves rearward, it increases the range of inward pivotal movement of said at least one temple bar 600, 620. When the adjustment badge 642 moves rearward, it moves the setting interlock 644 rearward, which in turn ratchets the snap adjustment apertures 644A-C over the snap protrusion 600B rearward. The setting interlock 644, by moving rearward, removes itself from between the hinge barrel 43 and the inner surface of the temple bar 600, 620 to increase the range of inward pivotal movement of the temple bar 600, 620. In another example, for a large head adjustment, the adjustment badge 642 moves rearward to increase the range of inward pivotal movement of the at least one temple bar.

Therefore, it can be seen that the present invention provides a unique solution to the problem of providing eyewear 100 which includes a hinge assembly 640 to provides for ratcheting adjustment of the width between temple bars 600, 620. By providing for ratcheting adjustment of the width, the temple bars 600, 620 can properly be fitted to accommodate a head of user with various widths.

Referring to FIGS. 43-63, the eyewear 100 of the present invention may also include one or more of the following elements: a nose piece structure with multiple axes of adjustment, a horizontal ledge defined within a lens of the safety eyewear for attaching a nose piece structure, a wicking device attached to the safety eyewear to remove or absorb perspiration, a coloration or tinting of an outer peripheral edge of a lens for indicating a performance characteristic of safety eyewear or a lens and selected absorption of visible wavelengths of light, temple bars of the safety eyewear having adjustable width, alone or in combination thereof. The illustrations in FIGS. 43-63 generally show some of the elements listed above but it should be noted that a single element or a combination of the elements above may be within the eyewear 100.

For example, the eyewear may include wire or metal core temples, soft pliable temple tips, and a ratchet mechanism for inclination of the eyewear to accommodate facial fit. It should be noted that the utility features referred to above can be employed on any type of eyewear. In a preferred embodiment, the eyewear is safety eyewear. The eyewear may be made of all plastic, selected metals, a combination of metal and plastic, or other relevant materials.

In summary, the safety eyewear of the present invention includes a nose piece structure with multiple axes of adjustment, a horizontal ledge defined within a lens of the safety eyewear for attaching a nose piece structure, a wicking device attached to the safety eyewear to remove or absorb perspiration, a coloration or tinting of an outer peripheral edge of a lens for indicating a performance characteristic of safety eyewear or a lens and selected absorption of visible wavelengths of light, temple bars of the safety eyewear having adjustable width, alone or in combination thereof.

It would be appreciated by those skilled in the art that various changes and modifications can be made to the illustrated embodiments without departing from the spirit of the present invention. All such modifications and changes are intended to be within the scope of the present invention.

What is claimed is:

1. A wicking device for eyewear, comprising:
   a sub-frame having a proximal and distal end, said sub-frame removably attached using a means for attachment to said eyewear frame at said proximal and distal end;
   a brow bar removably attached using means for attachment to said sub-frame; and
   a wicking material removably attached using means for attachment to said brow bar.

2. The wicking device of claim 1, wherein the sub-frame is a single piece that includes an insert portion at each end, each insert portion of the sub-frame is engaged within a corresponding receiving portion defined within the end pieces of the eyewear frame.

3. The wicking device of claim 1, wherein the sub-frame includes receiving portions at each end to allow insert portions of the brow bar to be inserted therein.

4. The wicking device of claim 1, wherein the brow bar matingly engages a contour of the sub-frame along a substantial portion of its length, the brow bar slightly raised above an upper surface of the sub-frame.

5. The wicking device of claim 1, further comprising:
   a central protrusion extending from the sub-frame near a central portion of the upper eyeframe area, said central protrusion engages a receiving aperture within said brow bar to secure the brow bar the sub-frame.

6. The wicking device of claim 1, wherein the sub-frame includes two pieces, a first piece and second piece attached to corresponding end pieces of said eyewear.

7. The wicking device of claim 1, wherein the brow bar is attached to the wicking sub-frame using snap options selected from a group consisting of:
   Tinnerman, S-wedge post, and snap.

8. An eyewear comprising:
   an eyewear frame;
   a sub-frame having a first end and a second end removably attached to said eyewear frame at said first and second ends, said first and second ends of said sub-frame and said eyewear frame including mating attachment formations;
   a brow bar removably attached to said sub-frame, said brow bar and said sub-frame including mating attachment formations; and
   a wicking material removably attached to said brow bar.

9. The eyewear of claim 8 wherein said sub-frame is a single piece including an insert portion at each end, each insert portion of said sub-frame being engaged within a corresponding receiving portion defined within end pieces of the eyewear frame.

10. The eyewear of claim 8, wherein said sub-frame includes receiving portions at each end to allow insert portions of the brow bar to be inserted therein.

11. The eyewear of claim 8, wherein said brow bar matingly engages a contour of said sub-frame along a substantial portion of its length, said brow bar being slightly raised above an upper surface of said sub-frame.

12. The eyewear of claim 8 wherein said mating attachment formations on said sub-frame and said brow bar comprise a central protrusion extending from said sub-frame near a central portion of an upper eyewear frame area, and a receiving aperture within said brow bar, said central protrusion engaging said receiving aperture to secure said brow bar to said sub-frame.

13. The eyewear of claim 8, wherein said sub-frame comprises a first piece and second piece attached to corresponding end pieces of said eyewear frame.

14. The eyewear of claim 8, wherein said mating attachment formations on said sub-frame and said brow bar are snap formations selected from the group consisting of: Tinnerman, S-wedge post, and snap.

15. A wicking device for an eyewear comprising:
   a sub-frame having a first end and a second end removably attached to an eyewear frame at said first and second ends, said first and second ends of said sub-frame and said eyewear frame including mating attachment formations;
   a brow bar removably attached to said sub-frame, said brow bar and said sub-frame including mating attachment formations; and
   a wicking material removably attached to said brow bar.

16. The wicking device of claim 15 wherein said sub-frame is a single piece including an insert portion at each end, each insert portion of said sub-frame being engaged within a corresponding receiving portion defined within end pieces of the eyewear frame.

17. The wicking device of claim 15, wherein said sub-frame includes receiving portions at each end to allow insert portions of the brow bar to be inserted therein.

18. The wicking device of claim 15, wherein said brow bar matingly engages a contour of said sub-frame along a substantial portion of its length, said brow bar being slightly raised above an upper surface of said sub-frame.

19. The wicking device of claim 15 wherein said mating attachment formations on said sub-frame and said brow bar comprise a central protrusion extending from said sub-frame near a central portion of an upper eyewear frame area, and a receiving aperture within said brow bar, said central protrusion engaging said receiving aperture to secure said brow bar to said sub-frame.

20. The wicking device of claim 15, wherein said sub-frame comprises a first piece and second piece attached to corresponding end pieces of said eyewear frame.

21. The wicking device of claim 15, wherein said mating attachment formations on said sub-frame and said brow bar are snap formations selected from the group consisting of: Tinnerman, S-wedge post, and snap.

* * * * *